US011406699B2

(12) United States Patent
Kehn-Hall et al.

(10) Patent No.: US 11,406,699 B2
(45) Date of Patent: Aug. 9, 2022

(54) ALPHAVIRUS AND COMPOSITIONS, METHODS, AND KITS RELATED THERETO

(71) Applicant: George Mason University, Fairfax, VA (US)

(72) Inventors: Kylene Wesley Kehn-Hall, Fredericksburg, VA (US); Brian D. Carey, Manassas Park, VA (US); Ivan V. Akhrymuk, Gainesville, VA (US); Caitlin W. Lehman, Manassas, VA (US)

(73) Assignee: George Mason University, Fairfax, VA (US)

( * ) Notice: Subject to any disclaimer, the term of this patent is extended or adjusted under 35 U.S.C. 154(b) by 71 days.

(21) Appl. No.: 16/820,462

(22) Filed: Mar. 16, 2020

(65) Prior Publication Data

US 2020/0297834 A1 Sep. 24, 2020

Related U.S. Application Data

(60) Provisional application No. 62/822,498, filed on Mar. 22, 2019.

(51) Int. Cl.
*A61K 39/12* (2006.01)
*C12N 15/86* (2006.01)
*A61K 39/00* (2006.01)

(52) U.S. Cl.
CPC ............... *A61K 39/12* (2013.01); *C12N 15/86* (2013.01); *A61K 2039/5254* (2013.01); *C12N 2770/36134* (2013.01); *C12N 2770/36141* (2013.01)

(58) Field of Classification Search
None
See application file for complete search history.

(56) References Cited

PUBLICATIONS

Carey et al., J. Virology, Aug. 2018, 92(15):e02068-17, 18 pages. (Year: 2018).*
Carey et al., PLoS Pathogens, Mar. 2020, 16(3):e1008282, 25 pages. (Year: 2020).*
Agnihothram et al., "Development of a Broadly Accessible Venezuelan Equine Encephalitis Virus Replicon Particle Vaccine Platform", Journal of Virology, Jun. 2018, vol. 92, Issue 11, pp. 1-14.
Carey et al., "Protein Phosphatase 1alpha Interacts with Venezuelan Equine Encephalitis Virus Capsid Protein and Regulates Viral Replication through Modulation of Capsid Phosphorylation", Journal of Virology, Aug. 2018, vol. 92, Issue 15, pp. 1-18.
Garmashova et al., "The Old World and New World Alphaviruses Use Different Virus-Specific Proteins for Induction of Transcriptional Shutoff", Journal of Virology, Mar. 2007, vol. 81, No. 5, pp. 2472-2484.
NCBI, "Structural polyprotein precursor [Venezuelan equine encephalitis virus]", GenBank: AAB02517.1, 2004, 3 pages. URL: https://www.ncbi.nlm.nih.gov/protein/AAB02517.1?report=genbank&log$=protalign&blast_rank=1 &RID=7UMWXXV1014.
NCBI, "Venezuelan equine encephalitis virus strain TC-83, complete genome", GenBank: L01443.1, 2004, 4 pages. URL: https://www.ncbi.nlm.nih.gov/nuccore/L01443.1?from=7562&to=11329.

* cited by examiner

*Primary Examiner* — Stacy B Chen
(74) *Attorney, Agent, or Firm* — Jordan IP Law, LLC; Todd A. Vaughn

(57) ABSTRACT

The present invention provides modified alphaviruses and compositions, methods, and kits for preparing and using them to elicit an immune response to an alphavirus in a subject.

10 Claims, 10 Drawing Sheets

Specification includes a Sequence Listing.

FIG. 2A

Mock — Merge | PKCδ | Capsid
VEEV — Merge | PKCδ | Capsid

FIG. 2B

Mock — Merge | PKCδ | E2
VEEV — Merge | PKCδ | E2

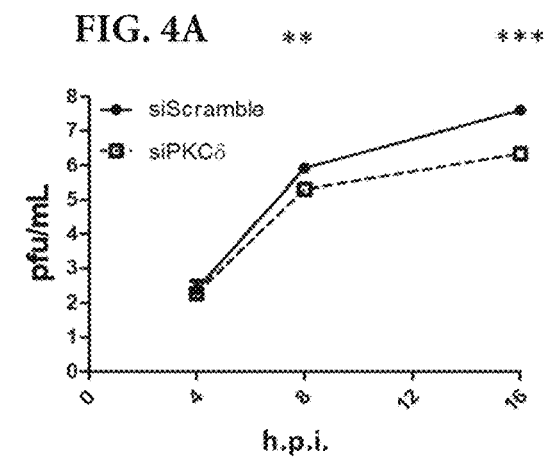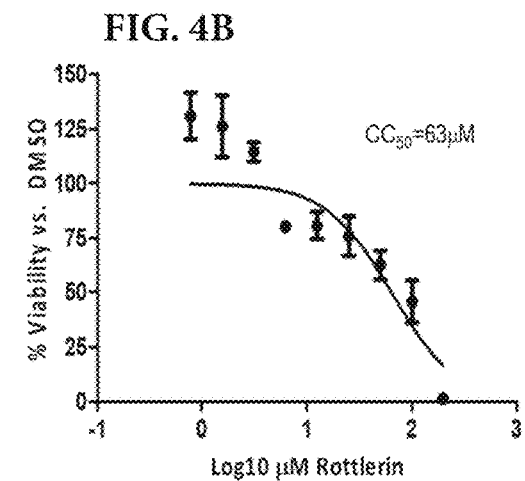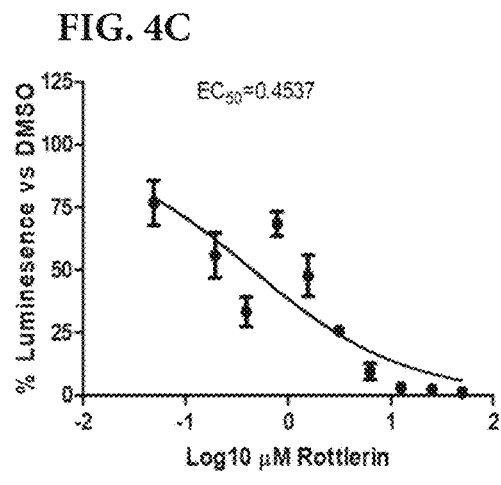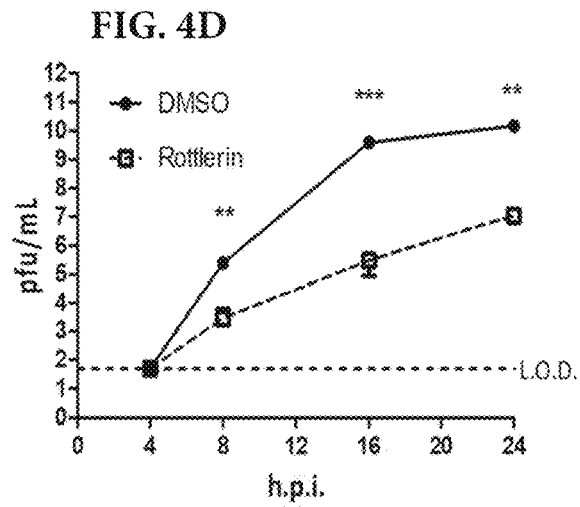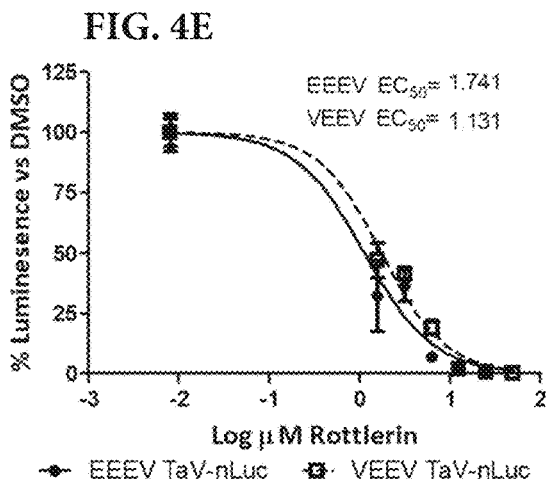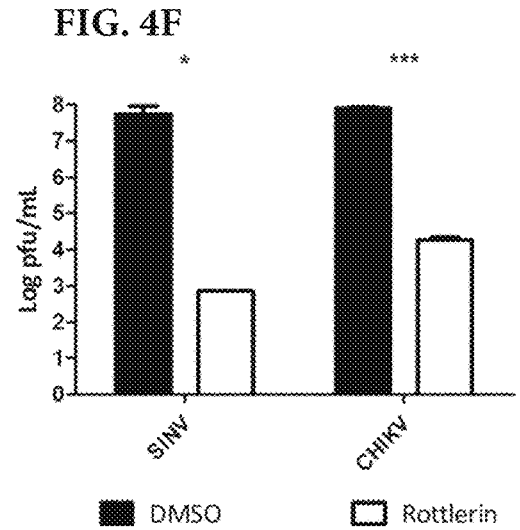

*Body Temperatures*

FIG. 10B

*Average Body Weights by Group*

ALPHAVIRUS AND COMPOSITIONS, METHODS, AND KITS RELATED THERETO

CROSS-REFERENCE TO RELATED APPLICATIONS

This non-provisional application claims the benefit under 35 U.S.C. § 119(e) to U.S. Provisional Application No. 62/822,498, filed on Mar. 22, 2019, which is hereby expressly incorporated by reference into the present application.

REFERENCE TO SEQUENCE LISTING

The Sequence Listing concurrently submitted herewith as a text file named "7074_0102PUS1_Sequence_Listing_ST25.txt," created on Feb. 12, 2020, and having a size of 178,156 bytes is herein incorporated by reference pursuant to 37 C.F.R. § 1.52(e)(5).

FIELD OF THE INVENTION

The present invention relates to alphaviruses and their use in eliciting an immune response to an alphavirus in a subject.

BACKGROUND

Members of the Togaviridae family, genera alphaviruses pose a serious health threat. For example, Venezuelan equine encephalitis virus (VEEV) is an alphavirus that causes significant disease and sometimes death in humans and equines (horses, donkeys). In humans, VEEV causes a febrile illness typified by fever, malaise, and vomiting. In some cases, infection progresses to the brain and encephalitis occurs. Neurological cases have a mortality rate as high as 35% in children and 10% in adults, with long-term neurological deficits often seen in survivors. Currently, there are no Food & Drug Administration (FDA) approved therapeutics or vaccines for human use available to treat or prevent this infection. There are also related viruses, such as eastern equine encephalitis virus (EEEV), western equine encephalitis virus (WEEV), and chikungunya virus (CHIKV) that are lacking in vaccines and therapeutics.

There remains a need for new and effective alphavirus vaccines, and compositions, methods, and kits related thereto.

SUMMARY OF THE INVENTION

In one aspect, the present invention provides an alphavirus having a capsid protein comprising a modification to decrease phosphorylation of the capsid protein compared to a nonmodified capsid.

In another aspect, the present invention provides a composition comprising an alphavirus; and a pharmaceutically acceptable carrier. The alphavirus has a capsid protein comprising a modification to decrease phosphorylation of the capsid protein compared to a nonmodified capsid.

In some aspects, the present invention provides a host cell comprising an alphavirus. The alphavirus has a capsid protein comprising a modification to decrease phosphorylation of the capsid protein compared to a nonmodified capsid.

In other aspects, the present invention provides a kit comprising an alphavirus. The alphavirus has a capsid protein comprising a modification to decrease phosphorylation of the capsid protein compared to a nonmodified capsid.

In still other aspects, the present invention provides a polynucleotide encoding the amino acid sequence of any one of SEQ ID NOs:6-17.

In one aspect, the present invention provides a method for eliciting an immune response in a subject against alphavirus. The method comprises administering to the subject a prophylactically or therapeutically effective amount of an alphavirus. The alphavirus has a capsid protein comprising a modification to decrease phosphorylation of the capsid protein compared to a nonmodified capsid.

In another aspect, the present invention provides a method for preventing a subject from becoming afflicted with an alphavirus-associated disease. The method comprises administering to the subject a prophylactically or therapeutically effective amount of an alphavirus. The alphavirus has a capsid protein comprising a modification to decrease phosphorylation of the capsid protein compared to a nonmodified capsid.

In some aspects, the present invention provides a method for delaying the onset, or slowing the rate of progression, of an alphavirus-associated disease in an alphavirus-infected subject. The method comprises administering to the subject a prophylactically or therapeutically effective amount of an alphavirus. The alphavirus has a capsid protein comprising a modification to decrease phosphorylation of the capsid protein compared to a nonmodified capsid.

In other aspects, the present invention provides a method for preparing an attenuated alphavirus. The method comprises providing a modified alphavirus having a genome capable of expressing a modified capsid protein comprising a modification relative to a nonmodified capsid of a wild-type alphavirus genome. The modification decreases phosphorylation of the modified capsid protein compared to the nonmodified capsid.

BRIEF DESCRIPTION OF THE DRAWINGS

FIGS. 2A-2D are confocal microscopy images. A) Representative fluorescence confocal microscopy images of either mock infected cells or cells infected with VEEV TC-83 (MOI 1.0) for 16 hours. Left Image—Merge of Capsid and PKCδ Middle Image—PKCδ Right Image—Capsid Arrowheads denote co-localization; B) Representative fluorescence confocal microscopy images of either mock infected cells or cells infected with VEEV TC-83 (MOI 1.0) for 16 hours. Left Image—Merge of Capsid and PKC Middle Image—PKCδ Right Image—Capsid; C) Line scan of z-stack analysis from confocal microscopy. Pearson's correlation=0.771±0.053. D) C) Line scan of z-stack analysis from confocal microscopy. Pearson's correlation=0.581±0.043. p<0.0001.

Figure 1A:
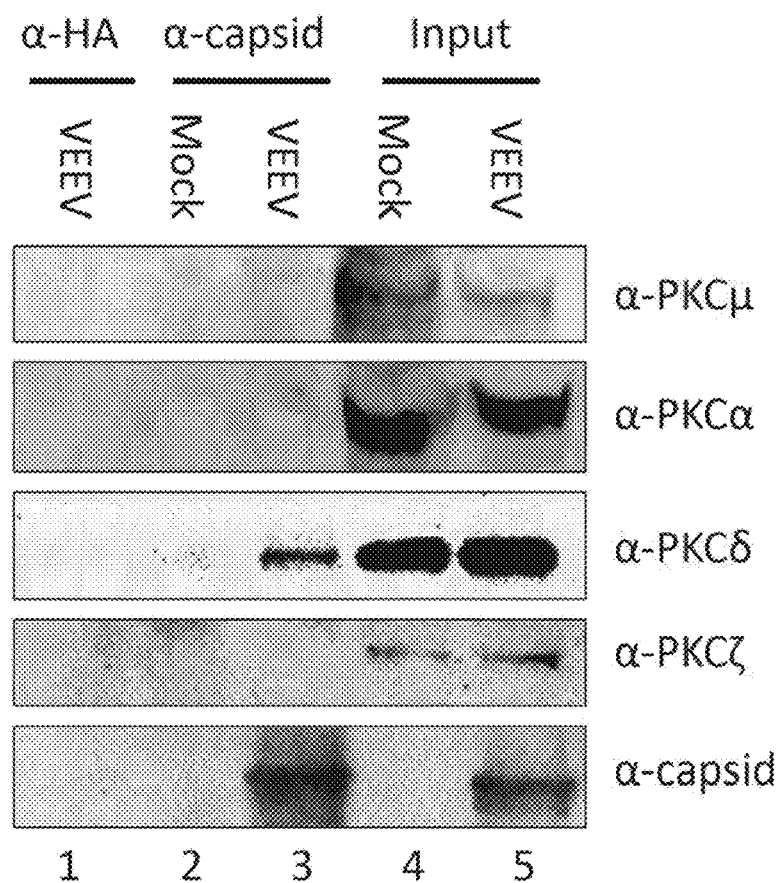
FIGS. 1A-1B are sodium dodecyl sulfate polyacrylamide gel electrophoresis (SDS-PAGE) followed by western blot analysis showing VEEV capsid co-immunoprecipitates with PKCδ. A) Vero cells mock-infected or infected with VEEV TC-83 (MOI of 1.0) for 24 hours. Images are representative of 3 biological replicates; and B) Vero cells mock-infected or infected with VEEV TC-83 (MOI of 1.0) and collected at the indicated time points. Images are representative of 3 biological replicates.

FIGS. 4A-4F are graphs showing inhibition of PKCδ causes a decrease in viral replication. A) U87MG cells were transfected with 50 nM scramble control or PKCδ siRNAs. Seventy two hours post-transfection, cells were infected with VEEV TC-83 (MOI 0.1) and viral supernatants collected at 4, 8, & 16 hpi for viral titer determination via plaque assay. Data is the average of 3 biological replicates±standard deviation =p<0.005, *=p<0.0005. B) Vero cells were treated with increasing concentrations of Rottlerin for 24 hours and cell viability was measured using Cell Titer-Glo assay from Promega. Luminescence was measured and normalized to DMSO. Values are average of 8 biological replicates. C) Vero cells were pretreated with increasing concentrations of Rottlerin for 1 hour and then infected with VEEV TC-83luc. Viral inoculum was removed after 1 hour and media with increasing concentrations of Rottlerin was added back to the cells. After 24 hours of infection, luciferase expression was measured using Promega Bright-Glo Luciferase assay. Values are average of 3 biological replicates±standard deviation. D) Vero cells were pretreated with DMSO or 10 μM Rottlerin and infected with VEEV TC-83 (MOI 0.1) for one hour. Cells were washed and post-treated with DMSO or 10 μM Rottlerin for the indicated time points. Viral supernatants were collected, and titer was determined via plaque assay. Values are average of 3 biological replicates±standard deviation. E) Vero cells were pretreated with indicated concentrations of Rottlerin and infected with VEEV TaV-nLuc or EEEV TaV-nLuc (MOI 0.1) for one hour. Cells were washed and post-treated with indicated concentrations of Rottlerin for 24 hours. Percent luminescence is displayed as compared to DMSO treated cells. Values are average of 3 biological replicates±standard deviation. F). Vero cells were pretreated with DMSO or 10 μM Rottlerin for one hour and then infected with the indicated virus (MOI 0.1). Cells were washed and post-treated with 10 μM Rottlerin or DMSO for 24 hours. Viral supernatants were collected and titers were assessed via plaque assay. Values are average of 3 biological replicates±standard deviation. *=p<0.1, =p<0.005, *=p<0.0005.

FIGS. 5A-5E are graphs and western blots showing VEEV CPD shows decreased phosphorylation of capsid. A) Schematic of the VEEV genome indicating the alanine substitutions made at T93, T108, S124, and T127. B) Vero cells were infected with either VEEV TC-83 or VEEV CPD (MOI 1.0). Cells were collected at 16 hpi, lysed, and immunoprecipitated with α-HA or α-VEEV capsid antibodies. Protein complexes were bound to Protein G Dynabeads, samples were run on SDS-PAGE, and western blot analysis was performed for phospho-Ser or phospho-Thr residues. Images are representative of 3 biological replicates. C) Western blot band density was analyzed on BioRad Quantity One software and normalized to capsid. Normalized values were calculated relative to TC-83 infected cells. Quantitation was performed for 3 biological replicates. *=p<0.05 D) Vero cells were infected with either VEEV TC-83 or VEEV CPD (MOI 1.0). Cells were collected at the indicated time points, lysed, samples were run on SDS-PAGE, and western blot analysis was performed for capsid and actin. E) Western blot band density was analyzed on BioRad Quantity One software and normalized to actin. Normalized values were calculated relative to TC-83 infected cells. Quantitation was performed for 3 biological replicates.

FIGS. 6A-6D are graphs showing VEEV CPD is more infectious than VEEV TC-83 and has increased vRNA: capsid binding. Vero cells or human primary astrocytes were infected with either VEEV TC-83 or VEEV CPD (MOI 0.1) and viral supernatants collected at the indicated time points for viral titer determination via A) plaque assay or B) RT-qPCR. C). Particle:PFU ratio was calculated at the indicated time points by converting RT-qPCR genomic copy per reaction data to genomic copies per milliliter. Genomic copies per milliliter were then divided by pfu/mL of the respective time point to obtain the particle to pfu ratio. Values are an average of 3 biological replicates±standard deviation. *=p<0.05, =p<0.005, *=p<0.0005, **=p<0.0001. D) Vero cells were infected with VEEV TC-83 or VEEV CPD (MOI 1.0). Cells were collected at the indicated time points, cross-linked, and cell lysates were immunoprecipitated with either α-HA or α-VEEV capsid antibodies. RT-qPCR against the VEEV packaging signal was performed on RNA isolated from immunocomplexes and normalized relative to a VEEV RNA standard curve generated during the same reaction. Genomic copies per reaction from α-HA immunoprecipitated samples were subtracted from the associated genomic copies from α-capsid immunoprecipitated samples to remove background and then the % RNA bound to capsid was determined by dividing the genomic copies from the input RNA by the normalized immunoprecipitated RNA. RNA:capsid binding of VEEV CPD was normalized relative to VEEV TC-83 samples. Data is average of 3 biological replicates. =p<0.005 ***=p<0.0005.

FIGS. 7A-7B are graphs showing VEEV CPD is attenuated in mice. A) Kaplan-Meier survival plot of mice intranasally infected with $2\times10^7$ pfu/mouse of either VEEV TC-83 or VEEV CPD. N=10 per group. *=p<0.05. B) Mice were monitored at least daily for clinical symptoms of disease over 21 days. Data are plotted per animal per day. Gray lines indicate a score of 1-3 (primarily reduced activity and weight loss); Light gray lines indicate a score of 4 or higher (primarily scruffy and hunched appearance, lethargy, severe weight loss); and dark gray indicates the animal was moribund and euthanized or found dead upon observation.

FIG. 8 is a schematic showing that capsid phosphorylation is a mechanism important for regulating capsid:viral RNA binding. Capsid is dephosphorylated by PP1α to allow for viral RNA to bind to capsid and assemble with E1/E2 at the cell membrane. Then after cell entry, PKCδ binds capsid after endosome escape which causes the release of viral RNA for translation and transcription.

Figure 9:
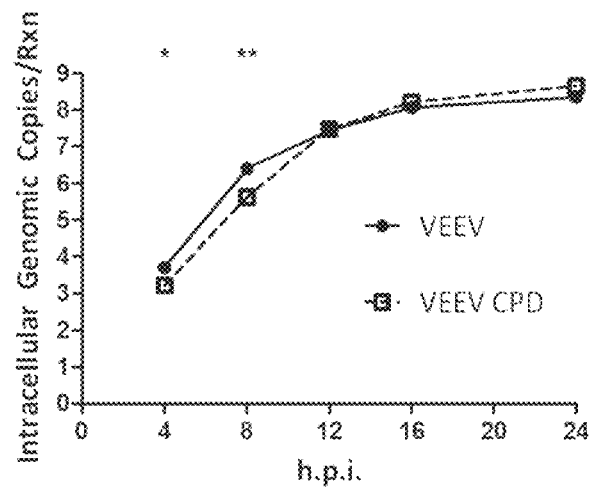

FIG. 9 is a graph showing intracellular VEEV RNA is decreased at early time points in cells infected with VEEV CPD vs. VEEV TC-83. Vero cells were infected with VEEV TC-83 or VEEV CPD at an MOI of 0.1. RNA was extracted from cells at the indicated time points and RT-qPCR was performed. Values are an average of 3 biological replicates. *=p<0.05, **=p<0.01.

FIGS. 10A-10B are graphs showing average body temperature and weights of mice infected with VEEV TC-83 or VEEV CPD. A) Daily average body temperature readings from mice infected with VEEV TC-83 or VEEV CPD. B) Daily average body weights from mice infected with VEEV TC-83 or VEEV CPD.

DETAILED DESCRIPTION OF THE INVENTION

In one aspect, the present invention provides an alphavirus having a capsid protein comprising a modification to decrease phosphorylation of the capsid protein compared to a nonmodified capsid.

In one embodiment, the nonmodified capsid is the capsid of a prototype or parent strain.

Accordingly, in some embodiments, the invention provides for attenuated alphaviruses having one or more modifications relative to a wild-type alphavirus.

In one embodiment, the modification prevents phosphorylation of one or more amino acid residues of the capsid protein by a serine/threonine kinase.

As used herein, the term "serine/threonine kinase" refers to an enzyme capable of phosphorylating a serine or threonine residue.

In one embodiment, the serine/threonine kinase is a protein kinase C (PKC), a DNA-dependent protein kinase (DNAPK), a protein kinase A (PKA), extracellular signal-regulated protein kinases 1 and 2 (ERK1/2), a glycogen synthase kinase 3 (GSK3) or a Us3 kinase.

In another embodiment, the serine/threonine kinase is a PKC. In some embodiment, the PKC is isoform α, δ, μ, or ζ.

In other embodiments, the PKC is PKCδ.

In some embodiments, the modification prevents phosphorylation of the one or more amino acid positions in any combination, resulting in a capsid protein in which serine and/or threonine phosphorylation has been sufficiently altered to result in an alphavirus having a capsid protein in which phosphorylation is diminished (e.g., decreased by at least about: 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more reduction in phosphorylation of the capsid relative to nonmodified capsid protein (e.g., relative to parental virus capsid) or eliminated (100% reduction in phosphorylation relative to nonmodified capsid protein (e.g., relative to parental virus capsid)).

In some embodiments, the modification prevents phosphorylation of the one or more amino acid positions in any combination, resulting in a capsid protein in which serine and/or threonine phosphorylation has been sufficiently altered to result in an alphavirus displaying an increase in particle to pfu ratio relative to nonmodified virus (e.g., relative to parental virus) (e.g., at least about: 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100 or more fold increase in particle to pfu ratio relative to nonmodified virus (e.g., relative to parental virus).

In some embodiments, the modification prevents phosphorylation of the one or more amino acid positions in any combination, resulting in a capsid protein in which serine and/or threonine phosphorylation has been sufficiently altered to result in an alphavirus displaying an increase in RNA:capsid binding relative to nonmodified virus (e.g., relative to parental virus).

In some embodiments, the modification prevents phosphorylation of the one or more amino acid positions in any combination, resulting in a capsid protein in which serine and/or threonine phosphorylation has been sufficiently altered to result in an alphavirus that is attenuated (e.g., live, attenuated), for example as determined in a mouse model of infection, with mice infected with the alphavirus showing increased survival and/or decreased clinical signs as compared to mice infected with a non-modified virus (e.g., parental virus).

In some embodiments, the alphavirus of the invention is an attenuated virus. In some embodiments, the attenuated virus is a live, attenuated virus. In another embodiment, the attenuated virus is a killed virus incapable of replication.

In other embodiments, the virulence of the alphavirus of the invention has been reduced by at least about: 2 fold, 3 fold, 4 fold, 5 fold, 6 fold, 7 fold, 8 fold, 9 fold, 10 fold, 20 fold, 30 fold, 40 fold, 50 fold, 60 fold, 70 fold, 80 fold, 90 fold, 100 fold or even greater. Viral attenuation can be confirmed using methods known to one of ordinary skill in the art. Non-limiting examples include plaque assays, growth measurements, and reduced lethality in test animals.

In some embodiments, the alphavirus of the present invention is an attenuated virus capable of replication, wherein pathogenicity of the virus has been reduced, and wherein administration of the virus to a subject will initiate an immune response without causing disease.

The alphavirus of this invention can be any alphavirus in the family Togaviridae, preferably any alphavirus against which it is desirable to elicit an immune response in a subject. Nonlimiting examples of an alphavirus of this invention include Venezuelan equine encephalitis virus (VEEV), Eastern equine encephalitis virus (EEEV), Western equine encephalitis virus (WEEV), Sindbis virus (SINV), Chikungunya virus (CHIKV), O'Nyong-Nyong virus (ONNV), Ross River virus (RRV), Mayaro virus (MAYV), Semliki Forest virus (SFV), Barmah Forest virus, Everglades, Mucambo, Pixuna, Middelburg, Getah, Bebaru, Una, Okelbo, Babanki, Fort Morgan, Ndumu and subgroups and strains thereof.

Examples of viruses classified as New World alphaviruses include, but are not limited to, VEEV, EEEV, and WEEV; and examples of viruses classified as Old World alphaviruses include, but are not limited to, SINV, CHIKV, ONNV, RRV, MAYV, and SFV.

In one embodiment, the alphavirus is a VEEV, an EEEV, a WEEV, a SINV, a CHIKV, a ONNV, a RRV, a MAYV, or a SFV.

In another embodiment, the alphavirus is a VEEV, a EEEV, or a WEEV. In other embodiments, the alphavirus is a SINV or a CHIKV.

In some embodiment, the alphavirus is a VEEV.

In one embodiment, the modification comprises one or more substitutions, deletions, or insertions at the one or more amino acid residues of the capsid protein or an alteration to a moiety chemically linked to the capsid protein.

In some embodiments, the modification can be replacement of one or more amino acids at particular positions in the capsid sequence with a different amino acid that is not naturally occurring at the particular position.

In other embodiments, the modification can be e.g., an altered carbohydrate or PEG structure attached/coupled to the capsid to decrease phosphorylation (e.g., prevents phosphorylation at one or more amino acids) of the capsid protein compared to a nonmodified capsid.

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine.

Other examples of amino acids and amino acids analogs are listed in Gross and Meienhofer, The Peptides: Analysis, Synthesis, Biology, Academic Press, Inc., New York (1983).

The stereochemistry of a protein can be described in terms of the topochemical arrangement of the side chains of the amino acid residues about the polypeptide backbone, which is defined by the peptide bonds between the amino acid residues and the I-carbon atoms of the bonded residues. In addition, polypeptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced peptides are largely comprised of L-amino acids. D-amino acids are the enantiomers of L-amino acids.

In another embodiment, the modification comprises one or more substitutions at the one or more amino acids of the capsid protein.

In one embodiment, the one or more substitutions comprise a substituted amino acid at the one or more amino acids, wherein the substituted amino acid is not a substrate for the serine/threonine kinase.

In some embodiments, the substituted amino acid is not a serine or threonine.

In other embodiments, the substituted amino acid is alanine, arginine, asparagine, aspartic acid, cysteine, glutamine, glutamic acid, glycine, histidine, isoleucine, leucine, lysine, methionine, phenylalanine, proline, tryptophan, tyrosine, valine, hydroxyproline, selenomethionine, norleucine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, or pipecolic acid.

Generally, the alphavirus virion is enveloped with viral glycoproteins, E1 & E2, incorporated into the membrane. The genome is approximately 11.4 kb and is positive sense single stranded RNA encoding two open reading frames. Four non-structural proteins (nsP1-4) are encoded by the first reading frame which begins at the 5' end of the genome. The subgenomic reading frame encodes for the structural proteins including capsid and three envelope proteins (E2, 6K, and E1). A small E3 protein is also encoded but not incorporated in the virion. Amino acid sequences of non-limiting exemplary capsid proteins are shown in Table 1.

TABLE 1

Amino acid sequences (single-letter code) of
non-limiting exemplary capsid proteins VEEV capsid (SEQ ID NO: 1)
```
  1 MFPFQPMYPMQPMPYRNPFAAPRRPWFPRTDPFLAMQVQELTRSMANLTFKQRRDAPPEG  60
 61 PSAKKPKKEASQKQKGGGQGKKKKNQGKKKAKTGPPNPKAQNGNKKKTNKKPGKRQRMVM 120
121 KLESDKTFPIMLEGKINGYQCVVGGKLFRPMHVEGKIDNDVLAALKTKKASKYDLEYADV 180
181 PQNMRADTFKYTHEKPQGYYSWHHGAVQYENGRFTVPKGVGAKGDSGRPILDNQGRVVAI 240
241 VLGGVNEGSRTALSVVMWNEKGVTVKYTPENCEQW
```

VEEV capsid (SEQ ID NO: 2)
```
  1 MFPFQPMYPMQPMPYRNPFAAPRRPWFPRTDPFLAMQVQELTRSMANLTFKQRRDAPPEG  60
 61 PPAKKPKREAPQKQKGGGQGKKKKNQGKKKAKTGPPNPKAQSGNKKKTNKKPGKRQRMVM 120
121 KLESDKTFPIMLEGKINGYACVVGGKLFRPMHVEGKIDNDVLAALKTKKASKYDLEYADV 180
181 PQNMRADTFKYTHEKPQGYYSWHHGAVQYENGRFTVPKGVGAKGDSGRPILDNQGRVVAI 240
241 VLGGVNEGSRTALSVVMWNEKGVTVKYTPENCEQW
```

TABLE 1-continued

Amino acid sequences (single-letter code) of
non-limiting exemplary capsid proteins

```
                     EEEV capsid (SEQ ID NO: 3)
  1 MFPYPTLNYPPMAPINPMAYRDPNPPRRRWRPFRPPLAAQIEDLRRSIANLTLKQRAPNP  60
 61 PAGPPAKRKKPAPKPKPAQAKKKRPPPPAKKQKRKPKPGKRQRMCMKLESDKTFPIMLNG 120
121 QVNGYACVVGGRVFKPLHVEGRIDNEQLAAIKLKKASIYDLEYGDVPQCMKSDTLQYTSD 180
181 KPPGFYNWHHGAVQYENNRFTVPRGVGGEGDSGRPILDNKGRVVAIVLGGVNEGSRTALS 240
241 VVTWDQKGVTVKDTPEGSEPWS WEEV capsid (SEQ ID NO: 4)
  1 MFPYPQLNFPPVYPTNPMAYRDPNPPRCRWRPFRPPLAAQIEDLRRSIANLTFKQRSPNP  60
 61 PPGPPPKKKKSAPKPKPTQPKKKKQQAKKTKRKPKPGKRQRMCMKLESDKTFPIMLNGQV 120
121 NGYACVVGGRLMKPLHVEGKIDNEQLAAVKLKKASMYDLEYGDVPQNMKSDTLQYTSDKP 180
181 PGFYNWHHGAVQYENGRFTVPRGVGGKGDSGRPILDNRGRVVAIVLGGANEGTRTALSVV 240
241 TWNQKGVTIKDTPEGSEPWS CHIKV capsid (SEQ ID NO: 5)
  1 MEFIPTQTFYNRRYQPRPWTPRSTIQIIRPRPRPQRQAGQLAQLISAVNKLTMRAVPQQK  60
 61 PRRNRKNKKQKQKQQAPQNNTNQKKQPPKKKPAQKKKKPGRRERMCMKIENDCIFEVKHE 120
121 GKVTGYACLVGDKVMKPAHVKGTIDNADLAKLAFKRSSKYDLECAQIPVHMKSDASKFTH 180
181 EKPEGYYNWHHGAVQYSGGRFTIPTGAGKPGDSGRPIFDNKGRVVAIVLGGANEGARTAL 240
241 SVVTWNKDIVTKITPEGAEEW
```

In some embodiments, the modification comprises one or more substitutions at amino acid residues corresponding to positions 44, 49, 62, 71, 93, 108, 124, 127, 167, 171, 188, 192, 201, 215, 226, and/or 264, or equivalent position, of SEQ ID NO:1.

As used herein, the term "equivalent position" refers to the position of the "equivalent" residue as it is positioned with respect to the amino acid sequence of its respective protein. For example, position 124 of SEQ ID NO:1 is serine (S124), and the "equivalent position" for SEQ ID NO:3 is position 110, also a serine; and the "equivalent position" for SEQ ID NO:4 is position 108, also a serine.

One of ordinary skill in the art knows that alignment methods can be used to identify which residues and/or positions are "equivalent" given the amino acid sequences of two or more proteins to be compared, whereby e.g., the alignment can display the residues for each protein on a single line, with gaps inserted such that "equivalent" residues appear in the same column even though their respective positions may be numbered differently depending on the sequence. In some embodiments, the equivalent position is a position that is within the same conserved region as the referenced or exemplified amino acid position.

In another embodiment, the modification comprises one or more substitutions at amino acid residues corresponding to positions 93, 108, 124, and/or 127, or equivalent position, of SEQ ID NO:1.

For amino acid substitutions, the following nomenclature may be used herein: original amino acid, position, substituted amino acid. For example, the substitution of threonine at position 98 with alanine may be designated as e.g., "Thr93Ala", "93Ala", "T93A", or "93A"; and multiple substitutions may be designated as e.g., "T93A/T108A/S124A/T127A" or "93A/108A/124A/127A", representing substitutions at positions 93, 108, 124, and 127 with alanine, respectively.

In one embodiment, the modification comprises one or more substitutions at amino acid residues corresponding to positions 93, 108, 124, and/or 127, or equivalent position, of SEQ ID NO:1, wherein the one or more substitutions are selected from the group consisting of 93$X_{aa1}$, 108$X_{aa2}$, 124$X_{aa3}$, 127$X_{aa4}$, and combinations thereof, wherein $X_{aa1}$, $X_{aa2}$, $X_{aa3}$, and $X_{aa4}$ each independently is not a substrate for phosphorylation by the serine/threonine kinase.

In another embodiment, $X_{aa1}$, $X_{aa2}$, $X_{aa3}$, and $X_{aa4}$ each independently is not a serine or threonine.

In some embodiments, $X_{aa1}$, $X_{aa2}$, $X_{aa3}$, and $X_{aa4}$ each independently is alanine, arginine, asparagine, aspartic acid, cysteine, glutamine, glutamic acid, glycine, histidine, isoleucine, leucine, lysine, methionine, phenylalanine, proline, tryptophan, tyrosine, valine, hydroxyproline, selenomethionine, norleucine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, or pipecolic acid.

In other embodiments, $X_{aa1}$, $X_{aa2}$, $X_{aa3}$, and $X_{aa4}$ each is independently is alanine.

In some embodiments, $X_{aa1}$, $X_{aa2}$, $X_{aa3}$, and $X_{aa4}$ each is alanine.

In one embodiment, the modification comprises a substitution at amino acid residue corresponding to position 93, or equivalent position, of SEQ ID NO:1.

In another embodiment, the modification comprises:
a first substitution at a first amino acid residue corresponding to position 93, or equivalent position, of SEQ ID NO:1; and
a second substitution at a second amino acid residue corresponding to position 108, or equivalent position, of SEQ ID NO:1.

In some embodiments, the modification comprises:
a first substitution at a first amino acid residue corresponding to position 93, or equivalent position, of SEQ ID NO:1;
a second substitution at a second amino acid residue corresponding to position 108, or equivalent position, of SEQ ID NO:1; and
a third substitution at a third amino acid residue corresponding to position 124, or equivalent position, of SEQ ID NO:1.

In other embodiments, the modification comprises:
a first substitution at a first amino acid residue corresponding to position 93, or equivalent position, of SEQ ID NO:1;
a second substitution at a second amino acid residue corresponding to position 108, or equivalent position, of SEQ ID NO:1;
a third substitution at a third amino acid residue corresponding to position 124, or equivalent position, of SEQ ID NO:1; and
a fourth substitution at a fourth amino acid residue corresponding to position 127, or equivalent position, of SEQ ID NO:1.

In one embodiment, the modification comprises:
a first substitution at a first amino acid residue corresponding to position 93, or equivalent position, of SEQ ID NO:1; and
a second substitution at a second amino acid residue corresponding to position 124, or equivalent position, of SEQ ID NO:1.

In another embodiment, the modification comprises:
a first substitution at a first amino acid residue corresponding to position 93, or equivalent position, of SEQ ID NO:1; and
a second substitution at a second amino acid residue corresponding to position 127, or equivalent position, of SEQ ID NO:1.

In some embodiments, the modification comprises:
a first substitution at a first amino acid residue corresponding to position 93, or equivalent position, of SEQ ID NO:1;
a second substitution at a second amino acid residue corresponding to position 124, or equivalent position, of SEQ ID NO:1; and
a third substitution at a third amino acid residue corresponding to position 127, or equivalent position, of SEQ ID NO:1.

In other embodiments, the modification comprises a substitution at amino acid residue corresponding to position 108, or equivalent position, of SEQ ID NO:1.

In one embodiment, the modification comprises:
a first substitution at a first amino acid residue corresponding to position 108, or equivalent position, of SEQ ID NO:1; and
a second substitution at a second amino acid residue corresponding to position 124, or equivalent position, of SEQ ID NO:1.

In another embodiment, the modification comprises:
a first substitution at a first amino acid residue corresponding to position 108, or equivalent position, of SEQ ID NO:1; and
a second substitution at a second amino acid residue corresponding to position 127, or equivalent position, of SEQ ID NO:1.

In some embodiments, the modification comprises:
a first substitution at a first amino acid residue corresponding to position 108, or equivalent position, of SEQ ID NO:1;
a second substitution at a second amino acid residue corresponding to position 124, or equivalent position, of SEQ ID NO:1; and
a third substitution at a third amino acid residue corresponding to position 127, or equivalent position, of SEQ ID NO:1.

In other embodiments, the modification comprises a substitution at amino acid residue corresponding to position 124, or equivalent position, of SEQ ID NO:1.

In one embodiment, the modification comprises:
a first substitution at a first amino acid residue corresponding to position 124, or equivalent position, of SEQ ID NO:1; and
a second substitution at a second amino acid residue corresponding to position 127, or equivalent position, of SEQ ID NO:1.

In another embodiment, the modification comprises a substitution at amino acid residue corresponding to position 127, or equivalent position, of SEQ ID NO:1.

In some embodiments, the alphavirus comprises a capsid protein having the sequence (single-letter code): MKLEX$_{aa5}$DKX$_{aa8}$FPIML (SEQ ID NO:6), wherein X$_{aa5}$ and X$_{aa8}$ each independently is not a substrate for phosphorylation by the serine/threonine kinase. In one embodiment, X$_{aa5}$ and X$_{aa8}$ each independently is not serine or threonine. In another embodiment, X$_{aa5}$ and X$_{aa8}$ each independently is alanine.

In some embodiments, the alphavirus comprises a capsid protein having the sequence (single-letter code): MKLEADKAFPIML (SEQ ID NO:7)

In one embodiment, the alphavirus comprises a capsid protein having the sequence (single-letter code): X$_{aa1}$GPPNPKAQNGNKKKX$_{aa16}$NKKPGKRQRMV-MKLEX$_{aa32}$DKX$_{aa35}$ (SEQ ID NO:8), wherein X$_{aa1}$, X$_{aa16}$, X$_{aa32}$, and X$_{aa35}$ each independently is not a substrate for phosphorylation by the serine/threonine kinase. In one embodiment, X$_{aa1}$, X$_{aa16}$, X$_{aa32}$, and X$_{aa35}$ each independently is not serine or threonine. In another embodiment, X$_{aa1}$, X$_{aa16}$, X$_{aa32}$, and X$_{aa35}$ each independently is alanine.

In some embodiments, the alphavirus comprises a capsid protein having the sequence (single-letter code): AGPPNPKAQNGNKKKANKKPGKRQRMVMKLEADKA (SEQ ID NO:9).

In one embodiment, the alphavirus comprises a capsid protein having the sequence (single-letter code):

```
                                         (SEQ ID NO: 10)
MFPFQPMYPMQPMPYRNPFAAPRRPWFPRTDPFLAMQVQELTRSMAN

LTFKQRRDAPPEGPSAKKPKKEASQKQKGGGQGKKKKNQGKKKAK

X_{aa93}GPPNPKAQNGNKKKX_{aa108}NKKPGKRQRMVMKLEX_{aa124}DK

X_{aa127}FPIMLEGKINGYACVVGGKLFRPMHVEGKIDNDVLAALKTKK

ASKYDLEYADVPQNMRADTFKYTHEKPQGYYSWHHGAVQYENGRFTVP

KGVGAKGDSGRPILDNQGRVVAIVLGGVNEGSRTALSVVMWNEKGVTV

KYTPENCEQW,
``` wherein X$_{aa93}$, X$_{aa108}$, X$_{aa124}$, and X$_{aa127}$ each independently is not a substrate for phosphorylation by the serine/threonine kinase. In another embodiment, X$_{aa93}$, X$_{aa108}$, X$_{aa124}$, and X$_{aa127}$ each independently is not serine or threonine. In some embodiments, X$_{aa93}$, X$_{aa108}$, X$_{aa124}$, and X$_{aa127}$ each independently is A.

In one embodiment, the alphavirus comprises a capsid protein having the sequence (single-letter code):

```
                                         (SEQ ID NO: 11)
MFPYPTLNYPPMAPINPMAYRDPNPPRRRWRPFRPPLAAQIEDLRRS

IANLTLKQRAPNPPGPPAKRKKPAPKPKPAQAKKKRPPPPAKKQKRK

PKPGKRQRMCMKLEXaa_{110}DKXaa_{113}FPIMLNGQVNGYACVVGGRV
```

FKPLHVEGRIDNEQLAAIKLKKASIYDLEYGDVPQCMKSDTLQYTSD

KPPGFYNWHHGAVQYENNRFTVPRGVGGEGDSGRPILDNKGRVVAIV

LGGVNEGSRTALSVVTWDQKGVTVKDTPEGSEPWS, wherein $X_{aa110}$ and $X_{aa113}$ each independently is not a substrate for phosphorylation by the serine/threonine kinase. In another embodiment, $X_{aa110}$ and $X_{aa113}$ each independently is not serine or threonine. In some embodiments, $X_{aa110}$ and $X_{aa113}$ each independently is A.

In one embodiment, the alphavirus comprises a capsid protein having the sequence (single-letter code):

(SEQ ID NO: 12)
MFPYPQLNFPPVYPTNPMAYRDPNPPRCRWRPFRPPLAAQIEDLRRS

IANLTFKQRSPNPPPGPPPKKKKSAPKPKPTQPKKKKQQAKKTKRK

PKPGKRQRMCMKLEX$_{aa108}$DKX$_{aa111}$FPIMLNGQVNGYACVVGGR

LMKPLHVEGKIDNEQLAAVKLKKASMYDLEYGDVPQNMKSDTLQYTS

DKPPGFYNWHHGAVQYENGRFTVPRGVGGKGDSGRPILDNRGRVVAI

VLGGANEGTRTALSVVTWNQKGVTIKDTPEGSEPWS, wherein $X_{aa108}$ and $X_{aa111}$ each independently is not a substrate for phosphorylation by the serine/threonine kinase. In another embodiment, $X_{aa108}$ and $X_{aa111}$ each independently is not serine or threonine. In some embodiments, $X_{aa108}$ and $X_{aa111}$ each independently is A.

In other embodiments, the alphavirus comprises a capsid protein having the sequence (single letter code):

(SEQ ID NO: 13)
MFPFQPMYPMQPMPYRNPFAAPRRPWFPRTDPFLAMQVQELTRSMAN

LTFKQRRDAPPEGPSAKKPKKEASQKQKGGGQGKKKKNQGKKKAKAG

PPNPKAQNGNKKKANKKPGKRQRMVMKLEADKAFPIMLEGKINGYAC

VVGGKLFRPMHVEGKIDNDVLAALKTKKASKYDLEYADVPQNMRADT

FKYTHEKPQGYYSWHHGAVQYENGRFTVPKGVGAKGDSGRPILDNQG

RVVAIVLGGVNEGSRTALSVVMWNEKGVTVKYTPENCEQW;

(SEQ ID NO: 14)
MFPFQPMYPMQPMPYRNPFAAPRRPWFPRTDPFLAMQVQELTRSMAN

LTFKQRRDAPPEGPPAKKPKREAPQKQKGGGQGKKKKNQGKKKAKAG

PPNPKAQSGNKKKANKKPGKRQRMVMKLEADKAFPIMLEGKINGYAC

VVGGKLFRPMHVEGKIDNDVLAALKTKKASKYDLEYADVPQNMRADT

FKYTHEKPQGYYSWHHGAVQYENGRFTVPKGVGAKGDSGRPILDNQG

RVVAIVLGGVNEGSRTALSVVMWNEKGVTVKYTPENCEQW;

(SEQ ID NO: 15)
MFPYPTLNYPPMAPINPMAYRDPNPPRRRWRPFRPPLAAQIEDLRRS

IANLTLKQRAPNPPAGPPAKRKKPAPKPKPAQAKKKRPPPPAKKQKR

KPKPGKRQRMCMKLEADKAFPIMLNGQVNGYACVVGGRVFKPLHVEG

RIDNEQLAAIKLKKASIYDLEYGDVPQCMKSDTLQYTSDKPPGFYNW

HHGAVQYENNRFTVPRGVGGEGDSGRPILDNKGRVVAIVLGGVNEGS

RTALSVVTWDQKGVTVKDTPEGSEPWS;
or (SEQ ID NO: 16)
MFPYPQLNFPPVYPTNPMAYRDPNPPRCRWRPFRPPLAAQIEDLRRS

IANLTFKQRSPNPPPGPPPKKKKSAPKPKPTQPKKKKQQAKKTKRKP

KPGKRQRMCMKLEADKAFPIMLNGQVNGYACVVGGRLMKPLHVEGKI

DNEQLAAVKLKKASMYDLEYGDVPQNMKSDTLQYTSDKPPGFYNWHH

GAVQYENGRFTVPRGVGGKGDSGRPILDNRGRVVAIVLGGANEGTRT

ALSVVTWNQKGVTIKDTPEGSEPWS.

In some embodiments, the structural proteins of the alphavirus of the present invention are translated as a polyprotein precursor. GenBank Accession No. L01443.1, which is herein incorporated by reference in its entirety, describes sequences for structural and nonstructural polyprotein precursors of a VEEV strain.

In one embodiment, the alphavirus of the present invention comprises structural proteins translated as a polyprotein precursor having the sequence (single letter code):

(SEQ ID NO: 17)
MFPFQPMYPMQPMPYRNPFAAPRRPWFPRTDPFLAMQVQELTRSMAN

LTFKQRRDAPPEGPSAKKPKKEASQKQKGGGQGKKKKNQGKKKAKAG

PPNPKAQNGNKKKANKKPGKRQRMVMKLEADKAFPIMLEGKINGYAC

VVGGKLFRPMHVEGKIDNDVLAALKTKKASKYDLEYADVPQNMRADT

FKYTHEKPQGYYSWHHGAVQYENGRFTVPKGVGAKGDSGRPILDNQG

RVVAIVLGGVNEGSRTALSVVMWNEKGVTVKYTPENCEQWSLVTTMC

LLANVTFPCAQPPICYDRKPAETLAMLSVNVDNPGYDELLEAAVKCP

GRKRRSTEELFNEYKLTRPYMARCIRCAVGSCHSPIAIEAVKSDGHD

GYVRLQTSSQYGLDSSGNLKGRTMRYDMHGTIKEIPLHQVSLYTSRP

CHIVDGHGYFLLARCPAGDSITMEFKKDSVRHSCSVPYEVKFNPVGR

ELYTHPPEHGVEQACQVYAHDAQNRGAYVEMHLPGSEVDSSLVSLSG

SSVTVTPPDGTSALVECECGGTKISETINKTKQFSQCTKKEQCRAYR

LQNDKWVYNSDKLPKAAGATLKGKLHVPFLLADGKCTVPLAPEPMIT

FGFRSVSLKLHPKNPTYLITRQLADEPHYTHELISEPAVRNFTVTEK

GWEFVWGNHPPKRFWAQETAPGNPHGLPHEVITHYYHRYPMSTILGL

SICAAIATVSVAASTWLFCRSRVACLTPYRLTPNARIPFCLAVLCCA

RTARAETTWESLDHLWNNNQQMFWIQLLIPLAALIVVTRLLRCVCCV

VPFLVMAGAAGAGAYEHATTMPSQAGISYNTIVNRAGYAPLPISITP

TKIKLIPTVNLEYVTCHYKTGMDSPAIKCCGSQECTPTYRPDEQCKV

FTGVYPFMWGGAYCFCDTENTQVSKAYVMKSDDCLADHAEAYKAHTA

SVQAFLNITVGEHSIVTTVYVNGETPVNFNGVKITAGPLSTAWTPFD

RKIVQYAGEIYNYDFPEYGAGQPGAFGDIQSRTVSSSDLYANTNLVL

QRPKAGAIHVPYTQAPSGFEQWKKDKAPSLKFTAPFGCEIYTNPIRA

ENCAVGSIPLAFDIDPDALFTRVSETPTLSAAECTLNECVYSSDFGGI

ATVKYSASKSGKCAVHVPSGTATLKEAAVELTEQGSATIHFSTANIH

PEFRLQICTSYVTCKGDCHPPKDHIVTHPQYHAQTFTAAVSKTAWTW

LTSLLGGSAVIIIGLVLATIVAMYVLTNQKHN.

In still other embodiments, the capsids and/or polyprotein precursors provided herein may further comprise one or more (e.g., 1, 2, 3, 4, 5, 6, 7, 8, 9, 10, 11, 12, 13, 14, 15, 16, 17, 18, 19, 20 or more) other substitutions, insertions, deletions, and/or additions (and combinations thereof) e.g., as compared to any polypeptide described herein (e.g., a polypeptide having a sequence as set forth in any one of SEQ ID NOs:6-17). Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Non-conservative amino acid substitutions typically entail exchanging a member of one of the classes described above for a member of another class. After making an amino acid substitution, insertion, deletion, and/or addition, the capsid containing the amino acid substitution(s), insertion(s), deletion(s), and/or addition(s) can be assessed using viral assays described herein and/or known in the art.

In other aspects, the present invention provides a method for preparing an alphavirus described herein. Alphavirus genomes with the desired modifications described herein can be prepared by any one of numerous methods including standard techniques (e.g., recombinant DNA techniques) known to one of ordinary skill in the art.

In one embodiment, the method comprises providing a modified alphavirus having a genome capable of expressing a modified capsid protein comprising a modification relative to a nonmodified capsid of a wild-type alphavirus genome, wherein the modification decreases phosphorylation of the modified capsid protein compared to the nonmodified capsid. In some embodiments, the modified capsid protein has the amino acid sequence as set forth in any one of SEQ ID NOs:6-16.

In some embodiments, an alphavirus RNA genome (e.g., isolated from virions or from infected cells) may be subjected to the desired modification (e.g., using oligonucleotide-directed, linker-scanning, polymerase chain reaction-based mutagenesis techniques) following its conversion to cDNA, and then reverted (e.g., via the RNA intermediate) back into infectious viral particles. In one embodiment, the entire cDNA copy of the genome can be cloned under the control of a phage RNA polymerase (e.g., SP6 or T7) promoter (e.g., cloned immediately downstream of the promoter) that allows the in vitro synthesis of genome RNA, which is then transfected into cells for generation of virus. In another embodiment, the DNA plasmid may be transfected into cells expressing a phage RNA polymerase in the cytoplasm.

In other embodiments, the modifying comprises de novo preparation of DNA containing codons corresponding to the desired modifications and substituting the corresponding region of the genome with the prepared DNA. In one embodiment, the entire genome can be substituted with the prepared DNA. In another embodiment, a portion of the genome can be substituted with the prepared DNA.

In other aspects, the present invention provides a composition comprising an alphavirus described herein. In another embodiment, the composition is a vaccine. In one embodiment, the composition comprises the alphavirus and a pharmaceutically acceptable carrier.

Pharmaceutically acceptable carriers are known to one of ordinary skill in the art and include, but are not limited to, one or more of phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of fatty acids or natural glycerides, and a propellant. Additional carriers such as lecithin may be included to facilitate intranasal delivery. Pharmaceutically acceptable carriers can further comprise auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

Suitable compositions and formulations are known in the art for preparing viruses therein. For example, U.S. Pat. No. 10,137,186 to Stinchcomb et al., which is herein incorporated by reference in its entirety, describes compositions and methods for alphavirus formulations.

In some embodiments, the composition comprises an alphavirus described herein: HEPES buffer, one or more carbohydrates, and a protein such as e.g., gelatin. In some embodiments, the carbohydrate is a sugar or a polyol. Sugars can include, but are not limited to, monosaccharides, (e.g. glucose, galactose, ribose, mannose, rhamnose, talose, xylose or allose arabinose), disaccharides (e.g. trehalose, sucrose, maltose, isomaltose, cellibiose, gentiobiose, laminaribose, xvlobiose, mannobiose, lactose, or fructose), trisaccharides (e.g. acarbose, raffinose, melizitose, panose, or cellotriose) or sugar polymers (e.g. dextran, xanthan, pullulan, cyclodextrins, amylose, amylopectin, starch, celloologosaccharides, cellulose, maltooligosaccharides, glycogen, chitosan, or chitin). Polvols can include, but are not limited to, mannitol, sorbitol, arabitol, erythritol, maltitol, xylitol, glycitol, glycol, polyglycitol, polyethylene glycol, polypropylene glycol, and glycerol.

In some embodiments, the alphavirus of the invention can be used directly in compositions (e.g., vaccine formulations), or lyophilized using lyophilization methods known to one of ordinary skill in the art.

In other embodiments, compositions (e.g., vaccines) of the invention comprise as an active ingredient an immunogenically effective amount of an alphavirus described herein. The virus may be introduced into a subject by any suitable means, including both parenteral injection (such as intraperitoneal, subcutaneous, or intramuscular injection), or orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering are known in the art, and any suitable conventional technique can be employed.

In other aspects, the present invention provides a method for eliciting an immune response in a subject against alphavirus. The method comprises administering to the subject a prophylactically or therapeutically effective amount or dose of a composition comprising the alphavirus of the invention described herein.

Subjects that can be administered or otherwise benefit from the alphavirus and alphavirus compositions of the present invention include vertebrates such as, without limitation, mammals. A mammal can be a human or animal including livestock and companion animals. Companion animals include but are not limited to animals kept as pets. Examples of companion animals include cats, dogs, and horses, as well as birds, such as parrots and parakeets. Livestock refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

In some embodiments, the subject is a human. In another embodiment, the subject is a non-human mammal.

In other embodiments, the subject can be a human who is a medical subject/patient (e.g., a patient in a hospital or clinic; a veterinarian patient (e.g., livestock or companion animal)); lab/clinical/health care provider (e.g., nurses, doctors, veterinarians, laboratory personnel), or a member of the armed services or law enforcement, or fire fighter.

Compositions (e.g., vaccines) of the invention can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

In some embodiments, administering comprises administering intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally.

Administering may be performed, for example, once, a plurality of times, and/or over one or more extended periods.

In one embodiment, the administering elicits a protective immune response in the subject against an alphavirus.

In another embodiment, the method is for protection of a subject against alphavirus, the method comprising administering to the subject a live attenuated alphavirus vaccine of the invention in an amount effective to protect the subject from infection by alphavirus.

In another embodiment, the present invention provides a method for preventing a subject from becoming afflicted with an alphavirus-associated disease, the method comprising administering to the subject a prophylactically effective dose of a composition described herein comprising an alphavirus of the invention.

In some embodiments, the subject has been exposed to, or is suspected of having been exposed to, an alphavirus, such that infection could result.

In other embodiments, the present invention provides a method for delaying the onset, or slowing the rate of progression, of an alphavirus-associated disease in an alphavirus-infected subject, the method comprising administering to the subject a therapeutically effective dose of a composition described herein comprising an alphavirus of the invention.

In other embodiments, eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art and, in some embodiments, can be on the order of several weeks to months. The present invention is not limited, however, to any particular method, route or frequency of administration.

In other embodiments, a prophylactically effective dose is any amount of a vaccine of the invention that, when administered to a subject prone to alphavirus infection or prone to affliction with an alphavirus-associated disorder, induces in the subject an immune response that protects the subject from becoming infected by the alphavirus or afflicted with the disorder.

In some embodiments, protecting the subject includes either reducing the likelihood of the subject becoming infected with the alphavirus, or lessening the likelihood of the disorder's onset in the subject, by at least about two-fold, preferably at least about two-fold, three-fold, four-fold, five-fold, tenfold, or more.

In other embodiments, a prophylactically effective dose induces in the subject an immune response that completely prevents the subject from becoming infected by an alphavirus or prevents the onset of the disorder in the subject entirely.

In some embodiments, a therapeutically effective dose is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

In other embodiments, any of the instant immunization and/or therapeutic methods further comprise administering to the subject at least one adjuvant e.g., for enhancing the immunogenicity of an antigen and boosting an immune response in a subject.

One of ordinary skill in the art can routinely determine optimum amounts/dosages, dosing methodologies and repetition rates. The optimum amount/dose can depend on the subject's state of health and weight, the mode of administration, the nature of the formulation, etc.

In some embodiments, an immunogenically effective dose is administered. For example, in one embodiment, about $10^3$ to about $10^7$ pfu alphavirus of the present invention per subject is administered, illustratively about $10^4$ to about $10^6$ pfu alphavirus per subject.

In other embodiments, an alphavirus of the invention of one particular serotype can be combined with viruses of other serotypes of alphavirus to achieve protection against multiple alphaviruses. For example, in some embodiments, the different viruses are in admixture and administered simultaneously, but may also be administered separately.

In some embodiments, the alphavirus compositions or vaccines of the invention may be combined with compositions or vaccines that induce protective responses to other agents.

In other aspects, the present invention provides a polynucleotide encoding the capsid or genome of an alphavirus of the present invention. In one embodiment, the polynucleotide is an isolated or purified polynucleotide. In another embodiment, the polynucleotide comprises RNA or cDNA. In some embodiments, an expression vector comprises the polynucleotide. In other embodiments, the expression vector is a plasmid.

In some embodiments, the polynucleotide encodes the amino acid sequence of any one of SEQ ID NOs:6-17.

In one embodiment, the polynucleotide comprises the sequence of any one of SEQ ID NOs:18-20.

In other aspects, the present invention provides a host cell comprising an alphavirus described herein. In some embodiments, the host cell is an isolated cell infected with the alphavirus. In some embodiments, host cells are mammalian host cells. In other embodiments, the cells are cultured cells.

In other aspects, the present invention provides a kit for use with methods and compositions described herein. Compositions and virus formulations may be provided in the kit. The kits can also include a suitable container and optionally one or more additional agents. In some embodiments, the container is a vial, test tube, flask, bottle, syringe and/or other container. In other embodiments, the kit comprises the alphavirus virus, a pharmaceutically acceptable carrier, an applicator, and instructional material for the use thereof e.g., for directing the administration of the alphavirus.

The invention will be further described in the following examples, which do not limit the scope of the invention described in the claims.

EXAMPLES

Example 1

Materials and Methods

Viral Infection and Drug Treatment

VEEV TC-83, VEEV Trinidad Donkey (TrD), and Sindbis virus (SINV) EgAr339 were obtained from BEI Resources. Chikungunya virus (CHIKV) 181/25 was a gift from Naomi Forrester, the University of Texas Medical Branch. VEEV TaV-nLuc and EEEV TaV-nLuc was kindly provided by William Klimstra of the University of Pittsburgh. The following reagents were obtained through the NIH Biodefense and Emerging Infections Research Resources Repository, NIAID, NIH: Venezuelan Equine Encephalitis Virus, TC-83, NR-63, Venezuelan Equine Encephalitis Virus, Trinidad Donkey, NR-332, Sindbis Virus, EgAr 339, NR-15695, and Polyclonal Anti-Venezuelan Equine Encephalitis Virus, TC-83 (Subtype IA/B) Capsid Protein (antiserum, Goat), NR-9403. All experiments with VEEV TrD and EEEV were performed under BSL3 conditions whereas the rest were performed under BSL2 conditions. All work involving select agents was registered with the Centers for Disease Control and Prevention and conducted at George Mason University's Biomedical Research Laboratory (Fairfax, Va., USA), which is registered in accordance with federal select agent regulations.

For infections, virus was added to supplemented Dulbecco's Modified Eagles Medium (DMEM) to achieve a MOI of either 0.1 or 1. Cells were infected for one hour at 37° C. and rocked every 15-20 min. Cells were then washed with sterile PBS pH 7.4 and media was added. Unless otherwise noted, cells were pre- and post-treated with either dimethyl sulfoxide (DMSO) or the PKCδ inhibitor, Rottlerin. DMSO concentration was equal to the volume of Rottlerin added to the media and always less than 0.1% of the final sample volume. Crystal violet plaque assays were performed to determine viral titers.

Cell Culture

Vero (ATCC, CCL-81) and U87MG (ATCC, HTB-14) cells were maintained at 37° C., 5% $CO_2$ in Dulbecco's modified Eagle medium (DMEM) supplemented with 10% fetal bovine serum (FBS), 1% glutamine, and 1% penicillin/streptomycin. BHK-21 (ATCC, CCL-10) cells were maintained at 37° C., 5% $CO_2$ in Modified Eagle Medium (MEM) supplemented with 10% fetal bovine serum (FBS), 1% glutamine, and 1% penicillin/streptomycin. Human Primary Astrocytes (Lonza CC-2565) were maintained at 37° C., 5% $CO_2$ in Astrocyte Growth Medium Bullet Kit (Lonza CC-3186).

Immunoprecipitation and Western Blot Analysis

Protein lysates were obtained using lysis buffer consisting of 50 mM Tris-HCl pH 7.4, 120 mM NaCl, 5 mM EDTA, 0.5% NP-40, 50 mM NaF, 0.2 mM $Na_3VO_4$, cOmplete™

Protease Inhibitor Cocktail (Sigma-Aldrich, 11697498001). Following cell lysis, 1 mg of total protein per sample was immunoprecipitated with 1 µg of anti-PKCδ (Cell Signaling, 9616) rabbit primary antibody, Anti-VEEV-capsid (BEI Resources, NR-9403) goat primary antibody, or anti-HA (Cell Signaling, 3724) rabbit primary antibody at 4° C. overnight. Following immunoprecipitation, antibody:antigen complexes were bound to Protein G Dynabeads (Thermo Fisher, 10004D). Beads containing the protein complexes were washed one time in $TNE_{600}$ with 0.1% NP-40, twice in $TNE_{150}$ with 0.1% NP-40, and once in PBS. Western blot loading buffer, consisting of Novex Tris-Glycine Sample Loading Buffer SDS (Thermo Fisher, LC2676), T-PER Tissure Protein Extraction Reagent (Thermo Fisher, 78510), EDTA, cOmplete Protease Inhibitor Cocktail, 50 mM NaF, 0.2 mM $Na_3VO_4$, and 300 mM DTT, was added to antibody:dynabead complexes and samples were run on NuPAGE™ 4-12% Bis-Tris Protein Gels (Thermo Fisher, NP0321). Following transfer to a PVDF membrane, membranes were blocked in either 5% BSA-TBS-Tween or 3% Milk-PB S-Tween and incubated in the indicated primary antibody [anti-PKCδ (Cell Signaling, 9616) 1:1000 dilution), anti-PKCµ, (Cell Signaling, 90039, 1:1000 dilution), anti-PKCα (Cell Signaling, 2056, 1:1000 dilution), anti-PKCζ (Cell Signaling, 9368, 1:1000 dilution), anti-VEEV-capsid (BEI Resources, 1:1000 dilution), anti-phosphoserine (Millipore, AB1603, 1:500 dilution), anti-phosphothreonine (Millipore, AB1607, 1:500 dilution), or anti-VEEV-E2 (1:500 dilution)] overnight at 4° C. Following primary antibody incubation, membranes were washed and incubated for 1 hour in the appropriate secondary antibody, either anti-rabbit HRP-conjugated (Cell Signaling, 7074), anti-mouse HRP-conjugated (Cell Signaling, 7076) or anti-goat HRP-conjugated. Membranes were imaged on a Chemidoc XRS molecular imager (BioRad) using the SuperSignal West Femto Maximum Sensitivity Substrate kit (Thermo Fisher, 34095). Non-immunoprecipitated samples were processed in the same way without performing the immunoprecipitation steps.

RNA Immunoprecipitation

Infected cells were collected, washed in PBS, and cross-linked with 1% paraformaldehyde. Cross-linked cells were lysed in RIPA lysis buffer (50 mM Tris-HCl, pH 7.5, 1% NP-40, 0.5% Sodium Deoxycholate, 0.05% Sodium Dodecyl Sulfate, 1 mM EDTA, cOmplete Protease Inhibitor Cocktail tablet, and 150 mM NaCl) and ultrasonicated. Lysates were clarified by centrifugation and immunoprecipitated as described above with α-HA and α-VEEV capsid antibodies. Following immunoprecipitation, antibody:antigen complexes were bound to protein G Dynabeads as described above. Beads bound to antibody complexes were washed in high stringency RIPA buffer (50 mM Tris-HCl, pH 7.5, 1% NP-40, 1% Sodium Deoxycholate, 0.1% Sodium Dodecyl Sulfate, 1 mM EDTA, 1M NaCl, 1M Urea, and cOmplete Protease Inhibitor Cocktail tablet) and resuspended in TEDS buffer (50 mM Tris-HCl, pH 7.0), 1% Sodium Dodecyl Sulfate, 5 mM EDTA, and 10 mM DTT). Samples were then processed for RNA extraction.

RNA Isolation and RT-qPCR

Supernatants were collected to analyze extracellular viral RNA, and infected cells were lysed and collected in TRIzol (Thermo Fisher, 15596026) to analyze intracellular RNA. Extracellular viral RNA was isolated using Ambion's Mag-Max Viral RNA Isolation Kit (Thermo Fisher, AM1836) while intracellular RNA and immunoprecipitated RNA (and input RNA) was isolated using the Direct-zol RNA Miniprep Kit (Zymo Research, R2050) by following the manufacturer's instructions. RT-qPCR was performed as described previously (Kehn-Hall K. et al., PLoS One., 7(4):e34761 (2012) for viral RNA using the Integrated DNA Technologies primer pairs and Taq-Man probe described elsewhere (Carey, B. D. et al. J. Virol., 92(15):e02068-17 (2018) against the viral RNA packaging signal (nt 1057-1154). The absolute quantification was determined using StepOne Software v2.3 based on the threshold cycle relative to the standard curve. The standard curve was determined using serial dilutions of VEEV-TC-83 RNA at known concentrations. Relative RNA:capsid binding was determined by subtracting the background RNA bound to antibody and dynabeads (α-HA IP samples) from the experimental samples and compared to input RNA levels. Results were normalized to TC-83 for comparison.

Luminescent Assays

For cell viability assays, cells were cultured as described above and transfected with siRNA at a final concentration of 50 nM. Cells were incubated for 72 hours and ATP production was measured as an indication of cell viability using Promega's Cell Titer-Glo (Promega, G7570). For viral luciferase assays, VEEV and EEEV TaV-nLuc luminesence was measured with Promega's Nano-Glo Luciferase Assay system (Promega, N1110). Assays were performed in white-walled, 96-well plates (Corning, 3610) seeded with 10,000 cells per well following the manufacturer's protocol. Luminescence was detected on a Beckman Coulter DTX880 plate reader after 100 ms integration per well.

Transfections

For siRNA transfections, U87MG cells were transfected with DharmaFECT transfection reagent (GE Lifesciences, T-2001) for 72 hours prior to VEEV infection. For siRNA either On-Target Plus SMARTpool for PRKCD (GE Lifesciences, L-003524-00) or All Stars siRNA (Qiagen, SI03650318) negative control were used. For experiments with plasmids, we previously described a VEEV structural polyprotein construct (Carey, B. D. et al., J. Virol., 92(15): 1-15 (2018)), herein incorporated by reference in its entirety) that was transfected using polyethylenimine (PEI) at a ratio of 4 µg PEI:1 µg DNA.

Confocal Microscopy

Vero cells were grown on poly-L-lysine coated coverslips in a 6-well plate, infected with VEEV TC-83 or mock-infected, and processed for immunofluorescence analysis as previously described (Lundberg, L. et al., Antiviral Res., 100(3):662-72 (2013)). Anti-VEEV-capsid goat primary antibody (1:1000 dilution) and Alexa Fluor 568 donkey anti-goat secondary antibody (Thermo Fisher, A11057, 1:500 dilution) were used to probe for capsid. Anti-PKCδ rabbit primary antibody (1:1000 dilution) and Alexa Fluor 488 donkey anti-rabbit secondary antibody (Thermo Fisher, A21206, 1:500 dilution) were used to probe for PKCδ. Anti VEEV-E2 mouse primary antibody (1:1000 dilution) and Alexa Fluor 568 anti-mouse secondary antibody (Thermo Fisher, A10037, 1:500 dilution) were used to probe for E2. Slides were imaged using an oil-immersion 60× objective lens on a Nikon Eclipse TE 2000-U confocal microscope, with all samples subjected to four line averaging. At least four images were taken of each sample, with one representative image shown. Each image was processed using Nikon NIS-Elements AR Analysis 3.2 software.

VEEV CPD Mutant Virus Production

The original plasmid containing the infectious cDNA of VEEV TC-83 was obtained from Ilya Frolov at the University of Alabama Birmingham and described elsewhere (Kinney, R. M. et al., J Virol., 67(3):1269-77 (1993)). Viral genome-coding cDNA was cloned under the control of the SP6 promoter. Mutations in the capsid-coding sequence of the VEEV TC-83 that prevents phosphorylation of the threonine and serine in positions 93, 108, 124 and 127 were introduced using standard DNA techniques. Briefly, in the plasmid that encodes VEEV TC-83 cDNA (see SEQ ID NO:21, wherein nucleotides 7562-11327 encode VEEV TC-83 structural polyprotein precursor of SEQ ID NO:22)), the fragment of the capsid sequence between AflII and Bsu361 restriction sites was replaced by in vitro synthesized gBlock gene fragment (Integrated DNA Technologies). In the gBlock fragment, all the serine and threonine codons corresponding to the capsid amino acids in positions 93, 108, 124 and 127 were changed to alanine codons (see SEQ ID NO:20, wherein nucleotides 7562-11327 encode VEEV CPD structural polyprotein precursor of SEQ ID NO:17)). Presence of the mutations in the phospho-deficient capsid mutant virus was confirmed by sequencing of the several viral genomes collected from infected cells. All of the sequences and details of the cloning procedures can be obtained upon request. In vitro transcription was performed on the mutated TC-83 molecular clone using the MEGA-script SP6 Transcription Kit (Thermo Fisher, AM1330). Resultant RNA was electroporated into BEM cells and virus was collected 24 hours post electroporation. Passage 0 virus titer was determined by plaque assay as described above and used to infect Vero cells to grow virus for passage 1 as described above. Passage 1 virus was used in subsequent experiments.

Animal Experiments

Six week old female C3H/HeN mice were obtained from Charles River Laboratories. Groups of 10 mice were individually identified via tattoo and had temperature transponders (BioMedic Data Systems) implanted subcutaneously 3 days prior to the start of the study. Mice were infected intranasally with a dose of $2 \times 10^7$ pfu/mouse of VEEV TC-83 or VEEV CPD. Animals were observed for survival over the course of 21 days. Mice were observed daily for signs of clinical illness as determined by our clinical sign scoring sheet developed for TC-83 animal studies. Mice were scored individually on the following parameters: appearance, mobility, attitude, and body condition. Appearance was scored as follows: 0—smooth coat, bright eyes; 1—slightly scruffy and/or hunched at rest; 2—scruffy and/or hunched at rest; 3—very scruffy and/or hunched at rest, mild eye crust; and 4—very scruffy and/or hunched at rest, closed inset eyes. Mobility was scored as follows: 0—active, exploring cage; 1—less active, walking; 2—slow movement; 3—no movement; and 4—unresponsive. Attitude was scored as follows: 0—alert, 1—mildly lethargic, 2-lethargic, and 3—unaware. Body condition was scored as follows: 0—normal or overweight; 1-underconditioned; and 2—emaciated. Scores for each parameter were summed for a total score and mice scoring 0-5 were observed once daily, mice scoring 6-10 were observed twice daily, and mice scoring an 11 or greater were humanely euthanized. Measurements of well-being, weights and body temperatures were recorded each day. Personnel performing clinical observations, weights and body temperatures were blinded to the animal groups. Experiments were performed in animal biosafety level 2 (ABSL-2) laboratories in accordance with the National Research Council's *Guide for the Care and Use of Laboratory Animals* (53) and under George Mason University IACUC protocol number 0384.

Statistical Analysis

Statistical analysis was performed using GraphPad Prism software (worldwideweb.graphpad.com). All experiments were done with at least 3 biological replicates and statistical significance was evaluated using Students T-test. P-values are indicated within the figure by an asterisk where *=p<0.05, =p<0.005, *=p<0.0005, and ****=p<0.0001.

Example 2

VEEV Capsid Co-Immunoprecipitates With PKCδ

In order to determine if PKC associates with capsid, co-immunoprecipitation experiments were performed.

Phospho-prediction site server, NetPhos 3.1 is an online tool that predicts phosphorylation sites in eukaryotic proteins using ensembles of neural networks. Analysis of the primary amino acid sequence of capsid by NetPhos 3.1 (Blom, N. et al., Proteomics, 4(6):1633-49 (2004)) resulted in a list of potential phosphorylation sites on capsid based on known kinase consensus sequences as shown in Table 2.

TABLE 2

Predicted Sites of Phosphorylation on VEEV capsid

| Sequence | Amino Acid | Position # | Score[1] | Potential Kinase |
|---|---|---|---|---|
| ELTRSMANL | Serine | 44 | 0.561 | PKA |
| ELTRSMANL | Serine | 44 | 0.506 | DNAPK |
| MANLTFKQR | Threonine | 49 | 0.887 | PKC |
| PEGPSAKKP | Serine | 62 | 0.972 | Unknown |
| PEGPSAKKP | Serine | 62 | 0.705 | PKC |
| KKEASQKQK | Serine | 71 | 0.981 | Unknown |
| KKEASQKQK | Serine | 71 | 0.781 | PKC |
| KKEASQKQK | Serine | 71 | 0.582 | DNAPK |
| KKAKTGPPN[2] | Threonine | 93 | 0.782 | PKC |
| NKKKTNKKP[2] | Threonine | 108 | 0.905 | PKC |
| MKLESDKTF[2] | Serine | 124 | 0.738 | Unknown |
| MKLESDKTF[2] | Serine | 124 | 0.683 | PKC |
| AALKTKKAS | Threonine | 167 | 0.931 | PKC |
| TKKASKYDL | Serine | 171 | 0.998 | Unknown |
| TKKASKYDL | Serine | 171 | 0.725 | PKA |
| MRADTFKYT | Threonine | 188 | 0.943 | Unknown |
| MRADTFKYT | Threonine | 188 | 0.829 | PKC |
| TFKYTHEKP | Threonine | 192 | 0.537 | PKC |
| QGYYSWHHG | Serine | 201 | 0.762 | Unknown |
| NGRFTVPKG | Threonine | 215 | 0.658 | PKC |
| AKGDSGRPI | Serine | 226 | 0.926 | Unknown |
| EKGVTVKYT | Threonine | 264 | 0.88 | PKC |

[1]Score is the confidence that the software has of the site being a true phosphorylation site. Values above 0.500 are considered above the threshold
[2]Sites experimentally shown to be phosphorylated (data not shown).

Any potential sites of tyrosine phosphorylation were removed. Next, any residues with a score below 0.500 were removed from analysis because scores below 0.500 indicate less than 50% confidence that the site is actually phosphorylated. The software also listed potential kinases for each residue including DNA-dependent protein kinase (DNAPK), Protein Kinase A (PKA), and Protein Kinase C (PKC). NetPhos 3.1 predicted an unknown kinase and PKC to be the responsible kinases of phosphorylation at those residues.

Figure 1B:
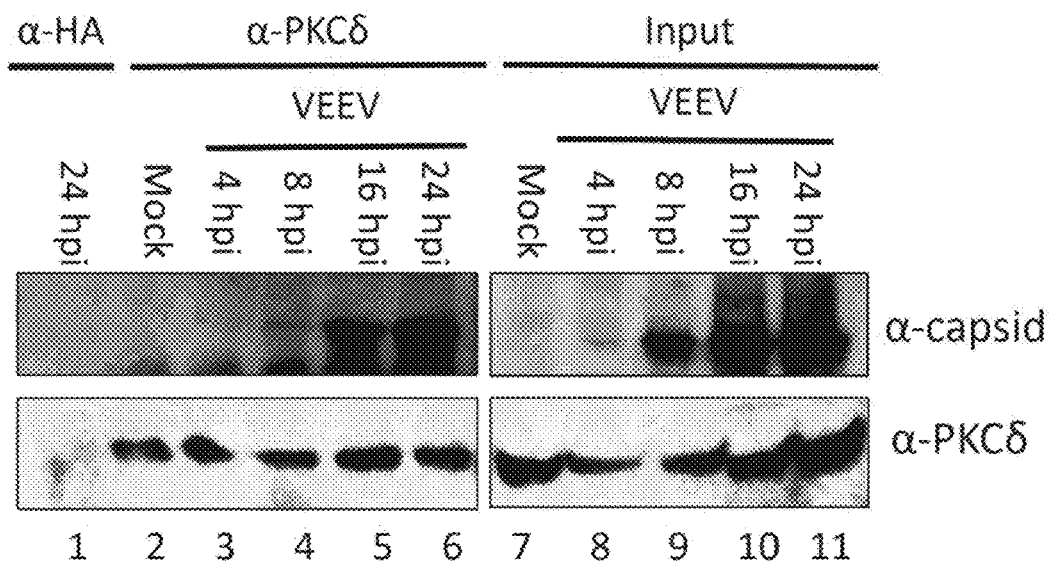

Vero cells were infected with VEEV TC-83 (a live attenuated vaccine strain of VEEV) or mock infected. Following infection, cells were lysed, and samples were immunoprecipitated with an antibody against VEEV capsid. Western blot analysis was done on immunoprecipitated samples with antibodies against PKC isoforms α, δ, μ, and ζ Analysis demonstrated an association between PKCδ and capsid but no other PKC isoforms tested (FIG. 1a). To determine at what point of the viral life cycle this interaction was most detectable, cells were infected with VEEV TC-83 and collected at 4, 8, 16, and 24 hours post infection (hpi). Samples were immunoprecipated with an antibody against PKCδ and western blot analysis for VEEV capsid was performed. Results indicated the association between capsid and PKCδ is highest at 16 and 24 hpi (FIG. 1b) with a slight interaction observed at 8 hpi. This detection at later time points could, however, be due to increased levels of virus at later time points making the interaction easier to detect. Furthermore, confocal microscopy was performed to visualize co-localization between VEEV capsid and PKCδ. Cells were either mock infected or infected with VEEV TC-83 and incubated for 16 hours. Cells were fixed, permeabilized, and stained with antibodies against PKCδ and either VEEV capsid (FIG. 2a) or VEEV E2 (FIG. 2b). Consistent with immunoprecipitation results, a clear co-localization between VEEV capsid and PKCδ was detected. A line scan analysis of z-stack images was performed (FIG. 2c) and a Pearson's correlation of 0.771 was determined. Line scan analysis of E2 and PKCδ z-stack images (FIG. 2d) did not show co-localization with a Pearson's correlation of 0.581. Localization of PKCδ in uninfected cells was fairly compact and perinuclear, suggesting localization in the ER/Golgi. However, after VEEV infection PKCδ localization displayed a more diffuse phenotype. Collectively, these results suggest that VEEV capsid interacts with PKCδ.

The data demonstrated that PKCδ interacts with VEEV capsid, as indicated by its co-immunoprecipitation with capsid and co-localization by confocal microscopy during VEEV infection.

Example 3

PKCδ Modulates the Phosphorylation of VEEV Capsid

In order to determine if PKCδ is responsible for the phosphorylation of VEEV capsid, cells were treated with siRNA targeting either PKCδ or a scrambled control, and then transfected with a plasmid expressing the structural polyprotein of VEEV.

Figure 3A:
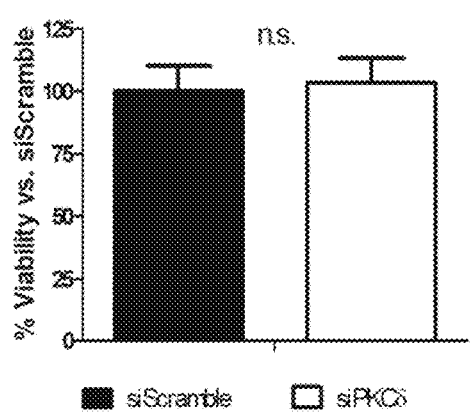
FIGS. 3A-3D are graphs and western blots showing siRNA Knockdown of PKC decreases phosphorylation of VEEV capsid. A) U87MG cells were transfected with 50 nM of the indicated siRNA and incubated for 72 hours. Cell viability was measured using Cell Titer-Glo assay from Promega. Luminescence was measured and normalized to siRNA scramble data. Values are average of 8 biological replicates. B) Western blots probing for PKCδ and actin from cell lysates treated with the indicated siRNA. Images are representative of 3 biological replicates. C) U87MG cells were transfected with siRNA against PKCδ or a scrambled control and incubated for 72 hours. Cells were transfected with a plasmid expressing the VEEV structural polyprotein and incubated for 48 hours. Cells were collected, lysed, and immunoprecipitated with α-HA or α-VEEV capsid antibodies. Protein complexes were bound to Protein G Dynabeads, samples were run on SDS-PAGE, and western blot analysis was performed for phospho-Ser or phospho-Thr residues. D) Western blot band density was analyzed on BioRad Quantity One software and normalized to capsid. Normalized values were calculated relative to siScramble transfected cells. Quantitation was performed for 3 biological replicates.
Figure 3B:
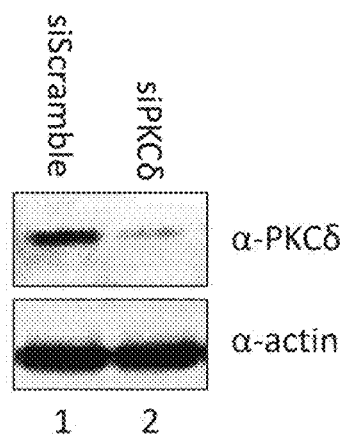
Figure 3C:
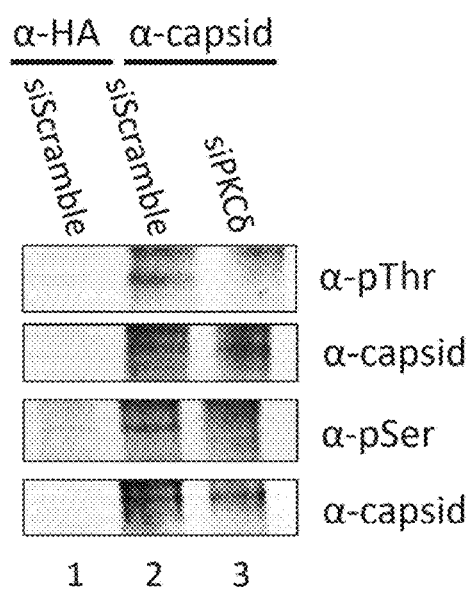
Figure 3D:
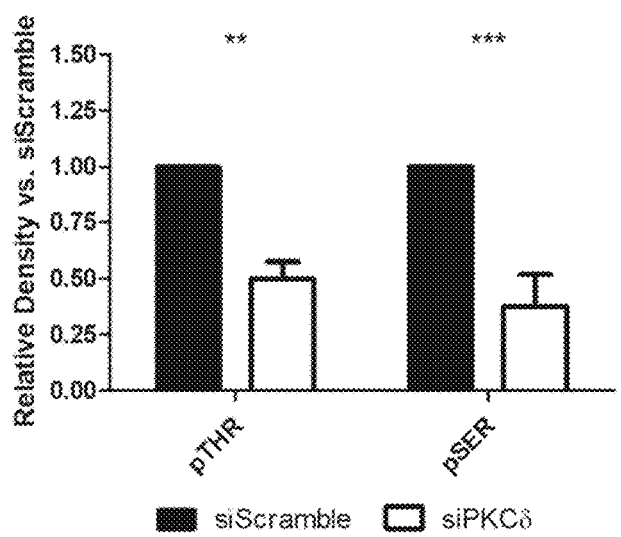

Following 48 hours of incubation, cells were collected, lysed, and samples were immunoprecipitated with an antibody against VEEV capsid. Anti-phospho-serine and anti-phospho-threonine antibodies were used to detect phosphorylation via western blot analysis. Capsid threonine phosphorylation was decreased by 50% and serine phosphorylation by 60% following PKCδ siRNA treatment (FIG. 3c & d). PKCδ siRNA had no effect on cell viability (FIG. 3a) and PKCδ protein expression was efficiently knocked down (FIG. 3b). These data suggest that PKCδ is involved in the phosphorylation of VEEV capsid.

Example 4

Inhibition of PKCδ Decreases Alphavirus Replication

In order to determine if the decrease in phosphorylation is important for VEEV replication, a series of experiments was performed to measure viral production after treatment with either siRNA directed against PKCδ or a small molecule inhibitor of PKCδ, Rottlerin.

Transfection of siRNA against PKCδ caused a significant time-dependent decrease in VEEV TC-83 viral titers (FIG. 4a) with more than one log decrease at 16 hpi. The PKCδ inhibitor, Rottlerin, is a potent inhibitor of VEEV TC-83 with an effective concentration 50% ($EC_{50}$) of less than 1 μM, which is well below its cytotoxic concentration 50% ($CC_{50}$) of 63 μM (FIG. 4b & c). Inhibiting PKCδ with 10 μM of Rottlerin triggered a 2 log decrease in VEEV TC-83 replication at 8 hpi and a 3 log decrease at both 16 and 24 hpi (FIG. 4d). The efficacy of Rottlerin against fully virulent VEEV and eastern equine encephalitis virus (EEEV) using nano-luciferase (nLuc) reporter viruses as well as SINV and chikungunya virus (CHIKV) was tested to assay the importance of PKCδ across the alphavirus genus. The $EC_{50}$ of Rottlerin was determined to be 1.1 μM for VEEV ZPC738 TaV-nLuc and 1.7 μM for EEEV FL93-939 TaV-nLuc (FIG. 4e). Treatment with Rottlerin also caused a 5 log decrease in SINV replication and a 3 log decrease in CHIKV replication (FIG. 4f), suggesting that PKCδ is an important kinase across the alphavirus genus.

A significant decrease of viral titers was observed starting at 8 hpi and continuing for at least 24 hpi when PKCδ was inhibited with the small molecule inhibitor, Rottlerin. PKCδ knockdown with siRNA also caused a significant decrease in viral titers.

Example 5

Phosphorylation Deficient Capsid Modified Virus Packages More Efficiently than TC-83

To further investigate the importance of the phosphorylation of VEEV capsid, a capsid deficient mutant virus was prepared using the VEEV TC-83 backbone (VEEV CPD).

Figures 5A, 5B, 5C, 5D, 5E:
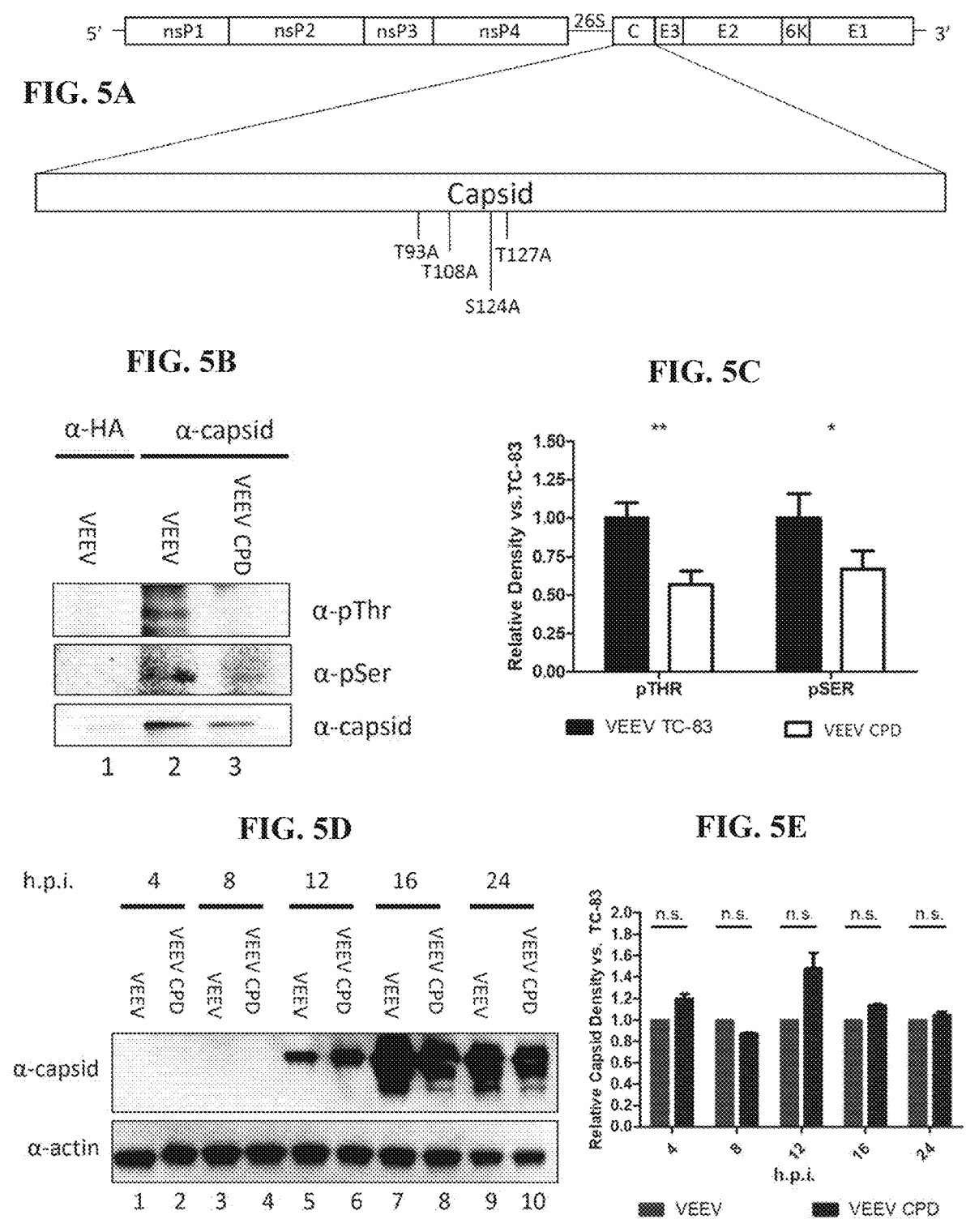
Figures 6A, 6B, 6C, 6D:
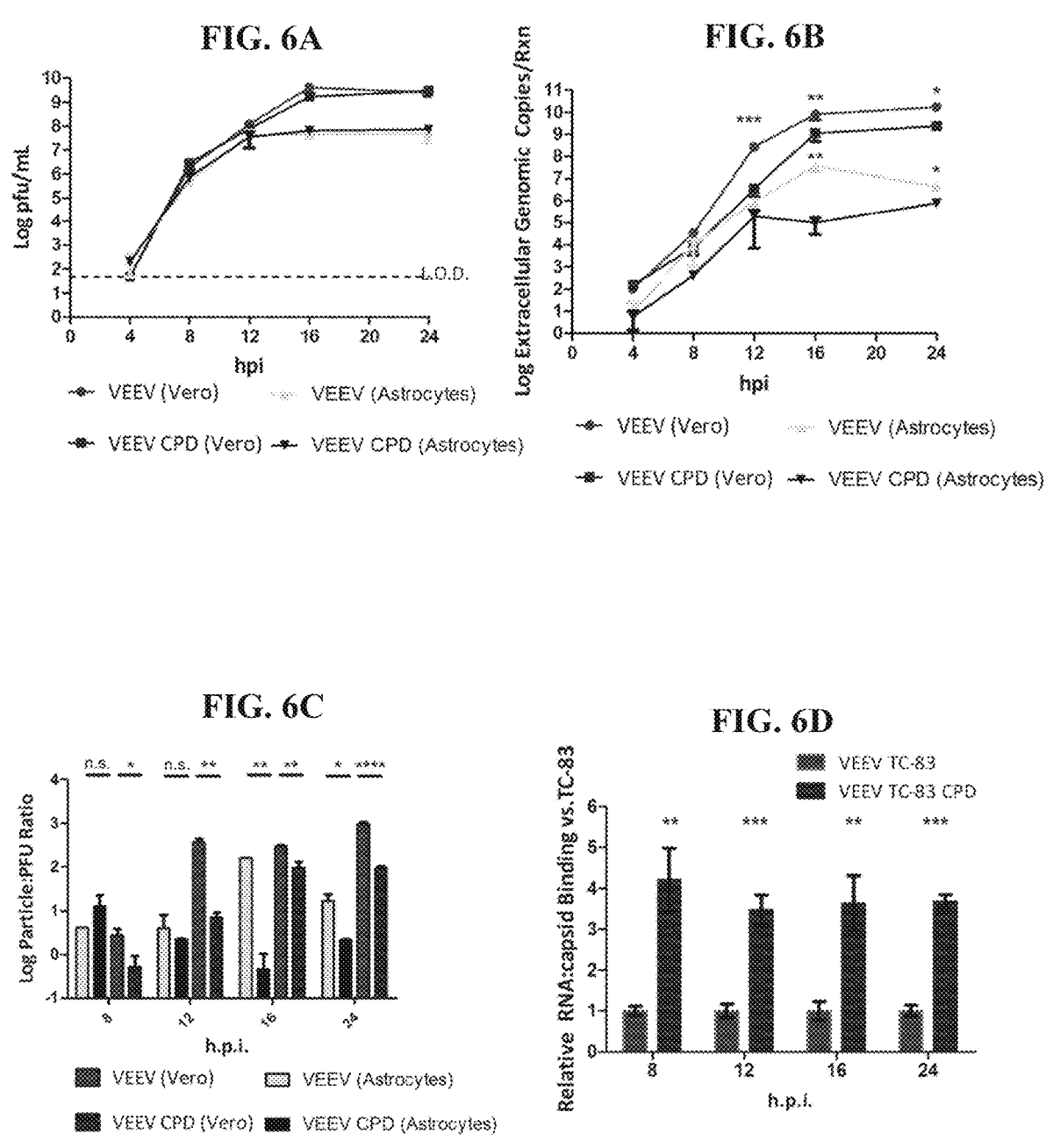

VEEV CPD was produced by mutating the following capsid residues to alanine (T93A, T108A, S124A, and T127A) (FIG. 5a). Cells infected with VEEV CPD showed decreased capsid phosphorylation on both threonine and serine residues (FIG. 5b & c) with no significant difference in capsid expression (FIG. 5d & e). Viral growth kinetics were measured at 4, 8, 12, 16, and 24 hpi in Vero cells. Growth kinetics were also observed in human primary astrocytes, given that the brain is a main target of the virus. Viral titers were unaltered between the two viruses in both cell types (FIG. 6a). There was significantly less viral RNA present in VEEV CPD infected cells at 4 and 8 hpi, but no differences at later time points (S1 Figure). However, analysis of the amount of viral RNA in the cell cultural media performed by RT-qPCR showed there was a significant decrease in extracellular viral RNA at later time points: 12 (Vero cells only), 16 and 24 hpi (FIG. 6b). A particle to PFU ratio analysis of extracellular genomic copies to particle forming units was performed and the particle to PFU ratio was determined to be lower in CPD vs. VEEV TC-83 (FIG. 6c). These data suggest that cells infected with CPD output more functional viral particles than TC-83, potentially due to more efficient viral packaging.

The phospho-deficient mutant virus, VEEV CPD, displayed no significant difference in titer when compared to the parental TC-83. The knockdown of PKCδ and mutation of capsid phosphorylated residues decreases the level of phosphorylation on VEEV capsid to almost undetectable levels. The knockdown of PKCδ coupled with the drop in capsid phosphorylation suggests that PKCδ is the kinase responsible for phosphorylating capsid.

Example 6

VEEV CPD Binds RNA More Efficiently than VEEV TC-83

In order to determine whether capsid phosphorylation mediates vRNA binding, the effect of VEEV CPD on vRNA binding to capsid was investigated. Cells were infected with either VEEV TC-83 or VEEV CPD, fixed in paraformaldehyde, lysed, and immunoprecipitated for VEEV capsid. After immunoprecipitation, RNA was isolated, and RT-qPCR was performed with primers targeting the RNA packaging signal. Results indicated that almost 4 times more RNA bound to capsid in the VEEV CPD vs. parental virus at all time points post infection tested (FIG. 6d). These data suggest that phosphorylation of capsid is inhibitory to viral RNA binding. The results indicated that there is more viral RNA bound to capsid in the mutant strain.

Figure 8:
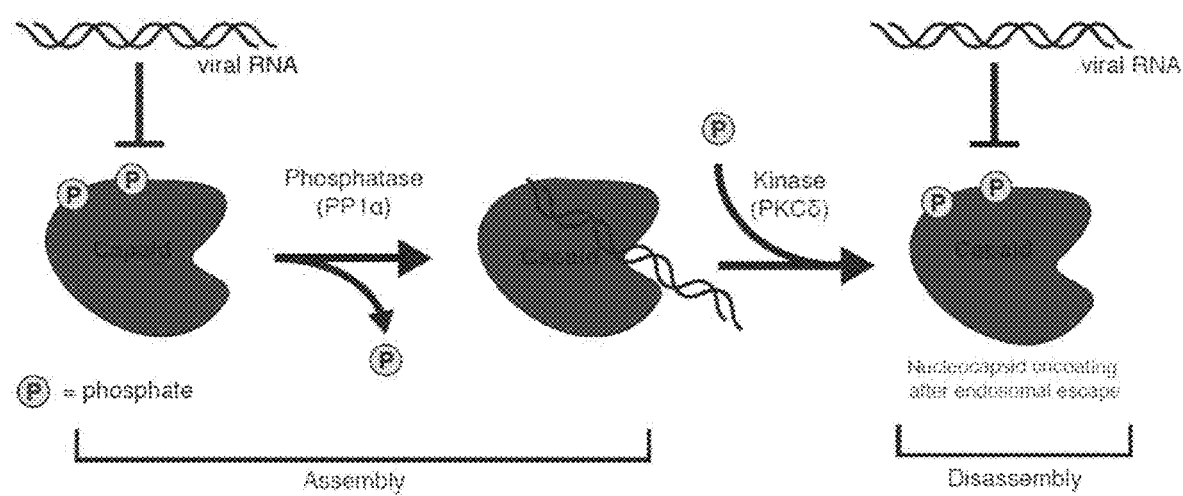

The data suggests that capsid phosphorylation/dephosphorylation is a cycle and that PKCδ regulates VEEV capsid binding to viral RNA (FIG. 8). Dephosphorylation of capsid by PP1α allows for vRNA to bind to capsid and assemble at the cell surface for budding while phosphorylation of capsid by PKCδ causes nucleocapsid uncoating and allows for viral RNA replication and translation.

Example 7

VEEV CPD Virus is Attenuated in a Mouse Model

Figures 7A, 7B:
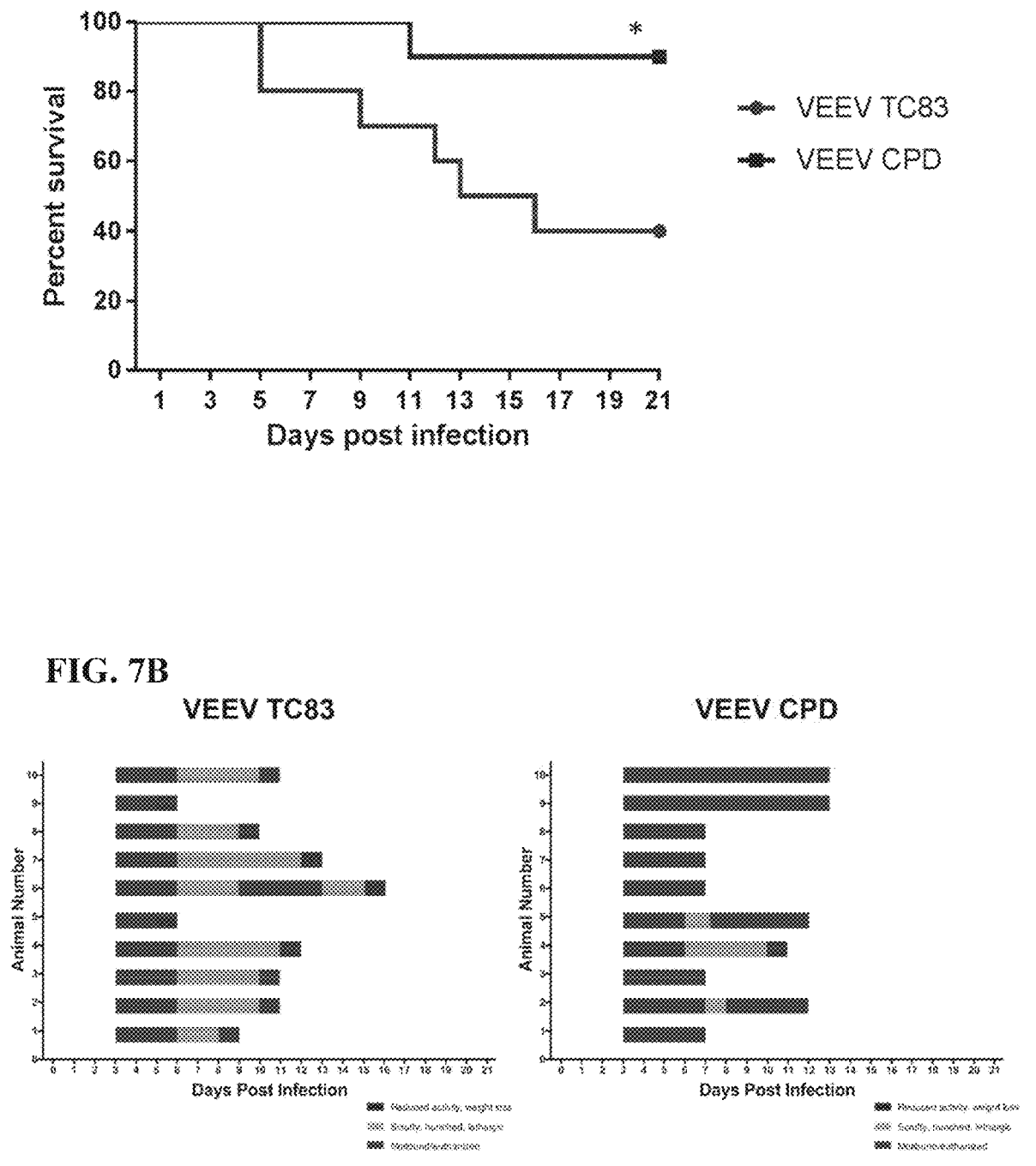

To determine if the mutations in VEEV capsid phosphorylation sites cause attenuation of VEEV TC-83 in vivo, six week old female C3H/HeN mice were challenged intranasally with a lethal dose of VEEV TC-83 or VEEV CPD. Mice were monitored for survival over 21 days and were observed daily for clinical symptoms of disease, weight loss, and body temperature. Sixty percent of mice infected with VEEV TC-83 succumbed to infection by 15 days post-infection while 90% of mice infected with VEEV CPD survived the infection (FIG. 7a). Furthermore, survivors infected with VEEV CPD showed less severe clinical signs of infection compared to TC-83 infected mice (FIG. 7b). Mice infected with TC-83 displayed mild signs of clinical illness (decreased activity, weight loss) by day 3 post-infection and increased in severity (scruffy, hunched, lethargic, significant weight loss) by day 5/6 post-infection. Surviving TC-83 mice recovered by day 11 (FIG. 7a). Meanwhile, mice infected with CPD mutant virus displayed mild signs of clinical illness (decreased activity, weight loss) with only 3 of the mice increasing to more severe signs and one mouse succumbing to infection (FIG. 7b and FIG. 10). These data suggest that CPD is attenuated in mice.

The data shows that mutating the phosphorylation sites on VEEV capsid attenuates the virus in vivo. Additionally, surviving mice infected with VEEV CPD display only mild clinical symptoms of infection suggesting that VEEV CPD does not induce the pathogenesis observed with VEEV TC-83.

We claim:

1. An alphavirus having a capsid protein comprising a modification to decrease phosphorylation of the capsid protein compared to a nonmodified capsid,
   wherein the alphavirus is a live, attenuated VEEV virus,
   the modification prevents phosphorylation of one or more amino acid residues of the capsid protein by a serine/threonine kinase, and
   the modification comprises one or more substitutions at amino acid residues corresponding to positions T93, T108, S124, and/or T127, or equivalent position, of SEQ ID NO:1.

2. The alphavirus of claim 1, wherein the serine/threonine kinase is a PKGδ.

3. The alphavirus of claim 1, wherein the alphavirus is capable of replication, wherein pathogenicity of the virus is reduced compared to a control virus comprising the nonmodified capsid, and wherein administration of the virus to a subject elicits an immune response.

4. The alphavirus of claim 1, wherein the capsid protein comprises the amino acid sequence as set forth in SEQ ID NO:10.

5. A composition comprising the alphavirus of claim 1; and a pharmaceutically acceptable carrier.

6. An isolated host cell comprising the alphavirus of claim 1.

7. A kit comprising the alphavirus of claim 1.

8. A method for eliciting an immune response in a subject against VEEV, the method comprises administering to the subject a prophylactically or therapeutically effective amount of the alphavirus of claim 1.

9. A method for preparing the live, attenuated VEEV alphavirus of claim 1, the method comprising
   providing a modified alphavirus having a genome capable of expressing a modified capsid protein comprising a modification relative to a nonmodified capsid of a wild-type alphavirus genome, wherein the modification decreases phosphorylation of the modified capsid protein compared to the nonmodified capsid.

10. The method of claim 9, wherein the modified capsid protein has the amino acid sequence as set forth in SEQ ID NO:10.

* * * * *

SEQUENCE LISTING

```
<160> NUMBER OF SEQ ID NOS: 22

<210> SEQ ID NO 1
<211> LENGTH: 275
<212> TYPE: PRT
<213> ORGANISM: Venezuelan equine encephalitis virus
<220> FEATURE:
<221> NAME/KEY: MISC_FEATURE
<223> OTHER INFORMATION: capsid protein

<400> SEQUENCE: 1

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Lys
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175
```

```
Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
            195                 200                 205

Tyr Glu Asn Gly Arg Phe Thr Val Pro Lys Gly Val Gly Ala Lys Gly
        210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275

<210> SEQ ID NO 2
<211> LENGTH: 275
<212> TYPE: PRT
<213> ORGANISM: Venezuelan equine encephalitis virus
<220> FEATURE:
<221> NAME/KEY: MISC_FEATURE
<223> OTHER INFORMATION: capsid protein

<400> SEQUENCE: 2

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Pro Ala Lys
    50                  55                  60

Lys Pro Lys Arg Glu Ala Pro Gln Lys Gln Lys Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Ser Gly Asn Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255
```

```
Met Trp Asn Glu Lys Gly Val Thr Val Lys Tyr Thr Pro Glu Asn Cys
            260                 265                 270

Glu Gln Trp
        275

<210> SEQ ID NO 3
<211> LENGTH: 262
<212> TYPE: PRT
<213> ORGANISM: Eastern equine encephalomyelitis virus
<220> FEATURE:
<221> NAME/KEY: MISC_FEATURE
<223> OTHER INFORMATION: capsid protein

<400> SEQUENCE: 3

Met Phe Pro Tyr Pro Thr Leu Asn Tyr Pro Pro Met Ala Pro Ile Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Ala Asn Leu Thr Leu Lys Gln Arg Ala Pro Asn Pro Pro Ala Gly Pro
    50                  55                  60

Pro Ala Lys Arg Lys Lys Pro Ala Pro Lys Pro Lys Pro Ala Gln Ala
65                  70                  75                  80

Lys Lys Lys Arg Pro Pro Pro Ala Lys Gln Lys Arg Lys Pro
                85                  90                  95

Lys Pro Gly Lys Arg Gln Arg Met Cys Met Lys Leu Glu Ser Asp Lys
            100                 105                 110

Thr Phe Pro Ile Met Leu Asn Gly Gln Val Asn Gly Tyr Ala Cys Val
        115                 120                 125

Val Gly Gly Arg Val Phe Lys Pro Leu His Val Glu Gly Arg Ile Asp
    130                 135                 140

Asn Glu Gln Leu Ala Ala Ile Lys Leu Lys Lys Ala Ser Ile Tyr Asp
145                 150                 155                 160

Leu Glu Tyr Gly Asp Val Pro Gln Cys Met Lys Ser Asp Thr Leu Gln
                165                 170                 175

Tyr Thr Ser Asp Lys Pro Pro Gly Phe Tyr Asn Trp His His Gly Ala
            180                 185                 190

Val Gln Tyr Glu Asn Asn Arg Phe Thr Val Pro Arg Gly Val Gly Gly
        195                 200                 205

Glu Gly Asp Ser Gly Arg Pro Ile Leu Asp Asn Lys Gly Arg Val Val
    210                 215                 220

Ala Ile Val Leu Gly Gly Val Asn Glu Gly Ser Arg Thr Ala Leu Ser
225                 230                 235                 240

Val Val Thr Trp Asp Gln Lys Gly Val Thr Val Lys Asp Thr Pro Glu
                245                 250                 255

Gly Ser Glu Pro Trp Ser
            260

<210> SEQ ID NO 4
<211> LENGTH: 260
<212> TYPE: PRT
<213> ORGANISM: Western equine encephalomyelitis virus
<220> FEATURE:
<221> NAME/KEY: MISC_FEATURE
<223> OTHER INFORMATION: capsid protein

<400> SEQUENCE: 4
```

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Cys Arg Trp Arg Pro
            20                  25                  30

Phe Arg Pro Pro Leu Ala Ala Gln Ile Glu Asp Leu Arg Arg Ser Ile
        35                  40                  45

Ala Asn Leu Thr Phe Lys Gln Arg Ser Pro Asn Pro Pro Gly Pro
50                  55                  60

Pro Pro Lys Lys Lys Lys Ser Ala Pro Lys Pro Lys Pro Thr Gln Pro
65              70                  75                  80

Lys Lys Lys Lys Gln Gln Ala Lys Lys Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Lys Gly
        195                 200                 205

Asp Ser Gly Arg Pro Ile Leu Asp Asn Arg Gly Arg Val Val Ala Ile
    210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Lys Asp Thr Pro Glu Gly Ser
                245                 250                 255

Glu Pro Trp Ser
        260

<210> SEQ ID NO 5
<211> LENGTH: 261
<212> TYPE: PRT
<213> ORGANISM: Chikungunya virus
<220> FEATURE:
<221> NAME/KEY: MISC_FEATURE
<223> OTHER INFORMATION: capsid protein

<400> SEQUENCE: 5

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys

```
                    85                  90                  95
Lys Lys Pro Gly Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260

<210> SEQ ID NO 6
<211> LENGTH: 13
<212> TYPE: PRT
<213> ORGANISM: Artificial Sequence
<220> FEATURE:
<223> OTHER INFORMATION: Capsid protein
<220> FEATURE:
<221> NAME/KEY: MISC_FEATURE
<222> LOCATION: (5)..(5)
<223> OTHER INFORMATION: Any amino acid that is not a substrate for
      phosphorylation by a serine/threonine kinase
<220> FEATURE:
<221> NAME/KEY: MISC_FEATURE
<222> LOCATION: (8)..(8)
<223> OTHER INFORMATION: Any amino acid that is not a substrate for
      phosphorylation by a serine/threonine kinase

<400> SEQUENCE: 6

Met Lys Leu Glu Xaa Asp Lys Xaa Phe Pro Ile Met Leu
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Capsid protein

<400> SEQUENCE: 7

Met Lys Leu Glu Ala Asp Lys Ala Phe Pro Ile Met Leu
1               5                   10

<210> SEQ ID NO 8
<211> LENGTH: 35
<212> TYPE: PRT
<213> ORGANISM: Artificial Sequence
<220> FEATURE:
<223> OTHER INFORMATION: Capsid protein
<220> FEATURE:
```

```
<221> NAME/KEY: MISC_FEATURE
<222> LOCATION: (1)..(1)
<223> OTHER INFORMATION: Any amino acid that is not a substrate for
      phosphorylation by a serine/threonine kinase
<220> FEATURE:
<221> NAME/KEY: MISC_FEATURE
<222> LOCATION: (16)..(16)
<223> OTHER INFORMATION: Any amino acid that is not a substrate for
      phosphorylation by a serine/threonine kinase
<220> FEATURE:
<221> NAME/KEY: MISC_FEATURE
<222> LOCATION: (32)..(32)
<223> OTHER INFORMATION: Any amino acid that is not a substrate for
      phosphorylation by a serine/threonine kinase
<220> FEATURE:
<221> NAME/KEY: MISC_FEATURE
<222> LOCATION: (35)..(35)
<223> OTHER INFORMATION: Any amino acid that is not a substrate for
      phosphorylation by a serine/threonine kinase

<400> SEQUENCE: 8

Xaa Gly Pro Pro Asn Pro Lys Ala Gln Asn Gly Asn Lys Lys Lys Xaa
1               5                   10                  15

Asn Lys Lys Pro Gly Lys Arg Gln Arg Met Val Met Lys Leu Glu Xaa
            20                  25                  30

Asp Lys Xaa
        35

<210> SEQ ID NO 9
<211> LENGTH: 35
<212> TYPE: PRT
<213> ORGANISM: Artificial Sequence
<220> FEATURE:
<223> OTHER INFORMATION: Capsid protein

<400> SEQUENCE: 9

Ala Gly Pro Pro Asn Pro Lys Ala Gln Asn Gly Asn Lys Lys Lys Ala
1               5                   10                  15

Asn Lys Lys Pro Gly Lys Arg Gln Arg Met Val Met Lys Leu Glu Ala
            20                  25                  30

Asp Lys Ala
        35

<210> SEQ ID NO 10
<211> LENGTH: 275
<212> TYPE: PRT
<213> ORGANISM: Artificial Sequence
<220> FEATURE:
<223> OTHER INFORMATION: Capsid protein
<220> FEATURE:
<221> NAME/KEY: Any amino acid that is not a substrate for
      phosphorylation by a serine/threonine kinase
<222> LOCATION: (93)..(93)
<220> FEATURE:
<221> NAME/KEY: Any amino acid that is not a substrate for
      phosphorylation by a serine/threonine kinase
<222> LOCATION: (108)..(108)
<220> FEATURE:
<221> NAME/KEY: Any amino acid that is not a substrate for
      phosphorylation by a serine/threonine kinase
<222> LOCATION: (124)..(124)
<220> FEATURE:
<221> NAME/KEY: Any amino acid that is not a substrate for
      phosphorylation by a serine/threonine kinase
<222> LOCATION: (127)..(127)

<400> SEQUENCE: 10

Met Phe Pro Phe Gln Pro Met Tyr Pro Met Gln Pro Met Pro Tyr Arg
1               5                   10                  15
```

```
Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
            35                  40                  45

Thr Phe Lys Gln Arg Arg Asp Ala Pro Pro Glu Gly Pro Ser Ala Lys
        50                  55                  60

Lys Pro Lys Lys Glu Ala Ser Gln Lys Gln Lys Gly Gly Gln Gly
 65                  70                  75                  80

Lys Lys Lys Lys Asn Gln Gly Lys Lys Ala Lys Xaa Gly Pro Pro
                85                  90                  95

Asn Pro Lys Ala Gln Asn Gly Asn Lys Lys Xaa Asn Lys Lys Pro
            100                 105                 110

Gly Lys Arg Gln Arg Met Val Met Lys Leu Glu Xaa Asp Lys Xaa Phe
            115                 120                 125

Pro Ile Met Leu Glu Gly Lys Ile Asn Gly Tyr Ala Cys Val Val Gly
            130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
            195                 200                 205

Tyr Glu Asn Gly Arg Phe Thr Val Pro Lys Gly Val Gly Ala Lys Gly
210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275

<210> SEQ ID NO 11
<211> LENGTH: 262
<212> TYPE: PRT
<213> ORGANISM: Artificial Sequence
<220> FEATURE:
<223> OTHER INFORMATION: Capsid Protein
<220> FEATURE:
<221> NAME/KEY: Any amino acid that is not a substrate for
      phosphorylation by a serine/threonine kinase
<222> LOCATION: (110)..(110)
<220> FEATURE:
<221> NAME/KEY: Any amino acid that is not a substrate for
      phosphorylation by a serine/threonine kinase
<222> LOCATION: (113)..(113)

<400> SEQUENCE: 11

Met Phe Pro Tyr Pro Thr Leu Asn Tyr Pro Pro Met Ala Pro Ile Asn
1               5                   10                  15

Pro Met Ala Tyr Arg Asp Pro Asn Pro Arg Arg Trp Arg Pro
            20                  25                  30

Phe Arg Pro Pro Leu Ala Ala Gln Ile Glu Asp Leu Arg Arg Ser Ile
            35                  40                  45

Ala Asn Leu Thr Leu Lys Gln Arg Ala Pro Asn Pro Pro Ala Gly Pro
```

```
                 50                  55                  60
Pro Ala Lys Arg Lys Lys Pro Ala Pro Lys Pro Lys Pro Ala Gln Ala
 65                  70                  75                  80

Lys Lys Lys Arg Pro Pro Pro Ala Lys Lys Gln Lys Arg Lys Pro
                 85                  90                  95

Lys Pro Gly Lys Arg Gln Arg Met Cys Met Lys Leu Glu Xaa Asp Lys
                100                 105                 110

Xaa Phe Pro Ile Met Leu Asn Gly Gln Val Asn Gly Tyr Ala Cys Val
                115                 120                 125

Val Gly Gly Arg Val Phe Lys Pro Leu His Val Glu Gly Arg Ile Asp
                130                 135                 140

Asn Glu Gln Leu Ala Ala Ile Lys Leu Lys Lys Ala Ser Ile Tyr Asp
145                 150                 155                 160

Leu Glu Tyr Gly Asp Val Pro Gln Cys Met Lys Ser Asp Thr Leu Gln
                165                 170                 175

Tyr Thr Ser Asp Lys Pro Pro Gly Phe Tyr Asn Trp His His Gly Ala
                180                 185                 190

Val Gln Tyr Glu Asn Asn Arg Phe Thr Val Pro Arg Gly Val Gly Gly
                195                 200                 205

Glu Gly Asp Ser Gly Arg Pro Ile Leu Asp Asn Lys Gly Arg Val Val
                210                 215                 220

Ala Ile Val Leu Gly Gly Val Asn Glu Gly Ser Arg Thr Ala Leu Ser
225                 230                 235                 240

Val Val Thr Trp Asp Gln Lys Gly Val Thr Val Lys Asp Thr Pro Glu
                245                 250                 255

Gly Ser Glu Pro Trp Ser
                260

<210> SEQ ID NO 12
<211> LENGTH: 260
<212> TYPE: PRT
<213> ORGANISM: Artificial Sequence
<220> FEATURE:
<223> OTHER INFORMATION: Capsid protein
<220> FEATURE:
<221> NAME/KEY: Any amino acid that is not a substrate for
      phosphorylation by a serine/threonine kinase
<222> LOCATION: (108)..(108)
<220> FEATURE:
<221> NAME/KEY: Any amino acid that is not a substrate for
      phosphorylation by a serine/threonine kinase
<222> LOCATION: (111)..(111)

<400> SEQUENCE: 12

Met Phe Pro Tyr Pro Gln Leu Asn Phe Pro Pro Val Tyr Pro Thr Asn
 1                5                  10                  15

Pro Met Ala Tyr Arg Asp Pro Asn Pro Arg Cys Arg Trp Arg Pro
                 20                  25                  30

Phe Arg Pro Pro Leu Ala Ala Gln Ile Glu Asp Leu Arg Arg Ser Ile
                 35                  40                  45

Ala Asn Leu Thr Phe Lys Gln Arg Ser Pro Asn Pro Pro Gly Pro
 50                  55                  60

Pro Pro Lys Lys Lys Lys Ser Ala Pro Lys Pro Lys Thr Gln Pro
 65                  70                  75                  80

Lys Lys Lys Lys Gln Gln Ala Lys Lys Thr Lys Arg Lys Pro Lys Pro
                 85                  90                  95

Gly Lys Arg Gln Arg Met Cys Met Lys Leu Glu Xaa Asp Lys Xaa Phe
                100                 105                 110
```

```
Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
        130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                    165                 170                 175

Ser Asp Lys Pro Pro Gly Phe Tyr Asn Trp His His Gly Ala Val Gln
                180                 185                 190

Tyr Glu Asn Gly Arg Phe Thr Val Pro Arg Gly Val Gly Gly Lys Gly
            195                 200                 205

Asp Ser Gly Arg Pro Ile Leu Asp Asn Arg Gly Arg Val Val Ala Ile
        210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Lys Asp Thr Pro Glu Gly Ser
                    245                 250                 255

Glu Pro Trp Ser
                260

<210> SEQ ID NO 13
<211> LENGTH: 275
<212> TYPE: PRT
<213> ORGANISM: Artificial Sequence
<220> FEATURE:
<223> OTHER INFORMATION: Capsid protein

<400> SEQUENCE: 13

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
            35                  40                  45

Thr Phe Lys Gln Arg Arg Asp Ala Pro Pro Glu Gly Pro Ser Ala Lys
        50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Ala Lys Ala Gly Pro Pro
                    85                  90                  95

Asn Pro Lys Ala Gln Asn Gly Asn Lys Lys Lys Ala Asn Lys Lys Pro
                100                 105                 110

Gly Lys Arg Gln Arg Met Val Met Lys Leu Glu Ala Asp Lys Ala Phe
            115                 120                 125

Pro Ile Met Leu Glu Gly Lys Ile Asn Gly Tyr Ala Cys Val Val Gly
        130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                    165                 170                 175

Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
            195                 200                 205
```

Tyr Glu Asn Gly Arg Phe Thr Val Pro Lys Gly Val Gly Ala Lys Gly
            210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275

<210> SEQ ID NO 14
<211> LENGTH: 275
<212> TYPE: PRT
<213> ORGANISM: Artificial Sequence
<220> FEATURE:
<223> OTHER INFORMATION: Capsid protein

<400> SEQUENCE: 14

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Pro Ala Lys
    50                  55                  60

Lys Pro Lys Arg Glu Ala Pro Gln Lys Gln Lys Gly Gly Gln Gly
65                  70                  75                  80

Lys Lys Lys Lys Asn Gln Gly Lys Lys Ala Lys Ala Gly Pro Pro
                85                  90                  95

Asn Pro Lys Ala Gln Ser Gly Asn Lys Lys Ala Asn Lys Lys Pro
            100                 105                 110

Gly Lys Arg Gln Arg Met Val Met Lys Leu Glu Ala Asp Lys Ala Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275

```
<210> SEQ ID NO 15
<211> LENGTH: 262
<212> TYPE: PRT
<213> ORGANISM: Artificial Sequence
<220> FEATURE:
<223> OTHER INFORMATION: Capsid protein

<400> SEQUENCE: 15

Met Phe Pro Tyr Pro Thr Leu Asn Tyr Pro Pro Met Ala Pro Ile Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Ala Asn Leu Thr Leu Lys Gln Arg Ala Pro Asn Pro Pro Ala Gly Pro
    50                  55                  60

Pro Ala Lys Arg Lys Lys Pro Ala Pro Lys Pro Lys Pro Ala Gln Ala
65                  70                  75                  80

Lys Lys Lys Arg Pro Pro Pro Ala Lys Lys Gln Lys Arg Lys Pro
                85                  90                  95

Lys Pro Gly Lys Arg Gln Arg Met Cys Met Lys Leu Glu Ala Asp Lys
                100                 105                 110

Ala Phe Pro Ile Met Leu Asn Gly Gln Val Asn Gly Tyr Ala Cys Val
            115                 120                 125

Val Gly Gly Arg Val Phe Lys Pro Leu His Val Glu Gly Arg Ile Asp
        130                 135                 140

Asn Glu Gln Leu Ala Ala Ile Lys Leu Lys Lys Ala Ser Ile Tyr Asp
145                 150                 155                 160

Leu Glu Tyr Gly Asp Val Pro Gln Cys Met Lys Ser Asp Thr Leu Gln
                165                 170                 175

Tyr Thr Ser Asp Lys Pro Pro Gly Phe Tyr Asn Trp His His Gly Ala
            180                 185                 190

Val Gln Tyr Glu Asn Asn Arg Phe Thr Val Pro Arg Gly Val Gly Gly
        195                 200                 205

Glu Gly Asp Ser Gly Arg Pro Ile Leu Asp Asn Lys Gly Arg Val Val
    210                 215                 220

Ala Ile Val Leu Gly Gly Val Asn Glu Gly Ser Arg Thr Ala Leu Ser
225                 230                 235                 240

Val Val Thr Trp Asp Gln Lys Gly Val Thr Val Lys Asp Thr Pro Glu
                245                 250                 255

Gly Ser Glu Pro Trp Ser
            260

<210> SEQ ID NO 16
<211> LENGTH: 260
<212> TYPE: PRT
<213> ORGANISM: Artificial Sequence
<220> FEATURE:
<223> OTHER INFORMATION: Capsid protein

<400> SEQUENCE: 16

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Cys Arg Trp Arg Pro
            20                  25                  30

Phe Arg Pro Pro Leu Ala Ala Gln Ile Glu Asp Leu Arg Arg Ser Ile
```

```
            35                  40                  45
Ala Asn Leu Thr Phe Lys Gln Arg Ser Pro Asn Pro Pro Gly Pro
        50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Lys Thr Lys Arg Lys Pro Lys Pro
                85                  90                  95

Gly Lys Arg Gln Arg Met Cys Met Lys Leu Glu Ala Asp Lys Ala Phe
                100                 105                 110

Pro Ile Met Leu Asn Gly Gln Val Asn Gly Tyr Ala Cys Val Val Gly
            115                 120                 125

Gly Arg Leu Met Lys Pro Leu His Val Glu Gly Lys Ile Asp Asn Glu
        130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
                180                 185                 190

Tyr Glu Asn Gly Arg Phe Thr Val Pro Arg Gly Val Gly Gly Lys Gly
            195                 200                 205

Asp Ser Gly Arg Pro Ile Leu Asp Asn Arg Gly Arg Val Val Ala Ile
        210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Lys Asp Thr Pro Glu Gly Ser
                245                 250                 255

Glu Pro Trp Ser
                260

<210> SEQ ID NO 17
<211> LENGTH: 1255
<212> TYPE: PRT
<213> ORGANISM: Artificial Sequence
<220> FEATURE:
<223> OTHER INFORMATION: Structural polyprotein precursor

<400> SEQUENCE: 17

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
            35                  40                  45

Thr Phe Lys Gln Arg Arg Asp Ala Pro Pro Glu Gly Pro Ser Ala Lys
        50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Ala Lys Ala Gly Pro Pro
                85                  90                  95

Asn Pro Lys Ala Gln Asn Gly Asn Lys Lys Ala Asn Lys Lys Pro
                100                 105                 110

Gly Lys Arg Gln Arg Met Val Met Lys Leu Glu Ala Asp Lys Ala Phe
            115                 120                 125

Pro Ile Met Leu Glu Gly Lys Ile Asn Gly Tyr Ala Cys Val Val Gly
```

-continued

```
                130                 135                 140
Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
                195                 200                 205

Tyr Glu Asn Gly Arg Phe Thr Val Pro Lys Gly Val Gly Ala Lys Gly
                210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
                260                 265                 270

Glu Gln Trp Ser Leu Val Thr Thr Met Cys Leu Leu Ala Asn Val Thr
                275                 280                 285

Phe Pro Cys Ala Gln Pro Pro Ile Cys Tyr Asp Arg Lys Pro Ala Glu
                290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
                340                 345                 350

Cys Ile Arg Cys Ala Val Gly Ser Cys His Ser Pro Ile Ala Ile Glu
                355                 360                 365

Ala Val Lys Ser Asp Gly His Asp Gly Tyr Val Arg Leu Gln Thr Ser
                370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
                420                 425                 430

Phe Leu Leu Ala Arg Cys Pro Ala Gly Asp Ser Ile Thr Met Glu Phe
                435                 440                 445

Lys Lys Asp Ser Val Arg His Ser Cys Ser Val Pro Tyr Glu Val Lys
                450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
                500                 505                 510

Val Ser Leu Ser Gly Ser Ser Val Thr Val Thr Pro Pro Asp Gly Thr
                515                 520                 525

Ser Ala Leu Val Glu Cys Glu Cys Gly Gly Thr Lys Ile Ser Glu Thr
                530                 535                 540

Ile Asn Lys Thr Lys Gln Phe Ser Gln Cys Thr Lys Lys Glu Gln Cys
545                 550                 555                 560
```

Arg Ala Tyr Arg Leu Gln Asn Asp Lys Trp Val Tyr Asn Ser Asp Lys
            565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
            595                 600                 605

Met Ile Thr Phe Gly Phe Arg Ser Val Ser Leu Lys Leu His Pro Lys
            610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
            645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
            675                 680                 685

Val Ile Thr His Tyr Tyr His Arg Tyr Pro Met Ser Thr Ile Leu Gly
            690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
            725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
            755                 760                 765

Asn Asn Asn Gln Gln Met Phe Trp Ile Gln Leu Leu Ile Pro Leu Ala
770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
            805                 810                 815

Ala Thr Thr Met Pro Ser Gln Ala Gly Ile Ser Tyr Asn Thr Ile Val
            820                 825                 830

Asn Arg Ala Gly Tyr Ala Pro Leu Pro Ile Ser Ile Thr Pro Thr Lys
            835                 840                 845

Ile Lys Leu Ile Pro Thr Val Asn Leu Glu Tyr Val Thr Cys His Tyr
850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
            885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
            915                 920                 925

Ala Asp His Ala Glu Ala Tyr Lys Ala His Thr Ala Ser Val Gln Ala
            930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
            965                 970                 975

-continued

```
Gly Pro Leu Ser Thr Ala Trp Thr Pro Phe Asp Arg Lys Ile Val Gln
            980                 985                 990
Tyr Ala Gly Glu Ile Tyr Asn Tyr Asp Phe Pro Glu Tyr Gly Ala Gly
        995                 1000                1005
Gln Pro Gly Ala Phe Gly Asp Ile Gln Ser Arg Thr Val Ser Ser
    1010                1015                1020
Ser Asp Leu Tyr Ala Asn Thr Asn Leu Val Leu Gln Arg Pro Lys
    1025                1030                1035
Ala Gly Ala Ile His Val Pro Tyr Thr Gln Ala Pro Ser Gly Phe
    1040                1045                1050
Glu Gln Trp Lys Lys Asp Lys Ala Pro Ser Leu Lys Phe Thr Ala
    1055                1060                1065
Pro Phe Gly Cys Glu Ile Tyr Thr Asn Pro Ile Arg Ala Glu Asn
    1070                1075                1080
Cys Ala Val Gly Ser Ile Pro Leu Ala Phe Asp Ile Pro Asp Ala
    1085                1090                1095
Leu Phe Thr Arg Val Ser Glu Thr Pro Thr Leu Ser Ala Ala Glu
    1100                1105                1110
Cys Thr Leu Asn Glu Cys Val Tyr Ser Ser Asp Phe Gly Gly Ile
    1115                1120                1125
Ala Thr Val Lys Tyr Ser Ala Ser Lys Ser Gly Lys Cys Ala Val
    1130                1135                1140
His Val Pro Ser Gly Thr Ala Thr Leu Lys Glu Ala Ala Val Glu
    1145                1150                1155
Leu Thr Glu Gln Gly Ser Ala Thr Ile His Phe Ser Thr Ala Asn
    1160                1165                1170
Ile His Pro Glu Phe Arg Leu Gln Ile Cys Thr Ser Tyr Val Thr
    1175                1180                1185
Cys Lys Gly Asp Cys His Pro Pro Lys Asp His Ile Val Thr His
    1190                1195                1200
Pro Gln Tyr His Ala Gln Thr Phe Thr Ala Ala Val Ser Lys Thr
    1205                1210                1215
Ala Trp Thr Trp Leu Thr Ser Leu Leu Gly Gly Ser Ala Val Ile
    1220                1225                1230
Ile Ile Ile Gly Leu Val Leu Ala Thr Ile Val Ala Met Tyr Val
    1235                1240                1245
Leu Thr Asn Gln Lys His Asn
    1250                1255

<210> SEQ ID NO 18
<211> LENGTH: 825
<212> TYPE: DNA
<213> ORGANISM: Artificial Sequence
<220> FEATURE:
<223> OTHER INFORMATION: Sequence encoding VEEV CPD capsid

<400> SEQUENCE: 18
atgttcccgt tccagccaat gtatccgatg cagccaatgc ctatcgcaa cccgttcgcg    60 gccccgcgca ggccctggtt ccccagaacc gacccttttc tggcgatgca ggtgcaggaa   120
ttaacccgct cgatggctaa cctgacgttc aagcaacgcc gggacgcgcc acctgagggg   180
ccatccgcta agaaaccgaa gaaggaggcc tcgcaaaaac agaaggggg aggccaaggg   240 aagaagaaga gaaccaagg gaagaagaag gctaaggcag gccgcctaa tcgaaggca    300 cagaatggaa acaagaagaa ggccaacaag aaaccaggca agacagcg catggtcatg   360
```

```
aaattggaag ctgacaaggc gttcccaatc atgttggaag ggaagataaa cggctacgct    420
tgtgtggtcg agggaagtt attcaggccg atgcatgtgg aaggcaagat agacaacgac     480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa atgggcgtt tcacggtgcc gaaaggagtt     660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccggag aactgcgagc aatgg                    825

<210> SEQ ID NO 19
<211> LENGTH: 3766
<212> TYPE: DNA
<213> ORGANISM: Artificial Sequence
<220> FEATURE:
<223> OTHER INFORMATION: Sequence encoding VEEV CPD structural
      polyprotein precursor

<400> SEQUENCE: 19
atgttcccgt tccagccaat gtatccgatg cagccaatgc cctatcgcaa cccgttcgcg     60
gccccgcgca ggccctggtt ccccagaacc gaccctttc tggcgatgca ggtgcaggaa    120
ttaacccgct cgatggctaa cctgacgttc aagcaacgcc gggacgcgcc acctgagggg    180
ccatccgcta gaaaccgaa gaaggaggcc tcgcaaaaac agaaggggg aggccaaggg     240 aagaagaaga gaaccaagg gaagaagaag gctaaggcag gccgcctaa tccgaaggca     300 cagaatggaa acaagaagaa ggccaacaag aaaccaggca gagacagcg catggtcatg    360 aaattggaag ctgacaaggc gttcccaatc atgttggaag ggaagataaa cggctacgct    420
tgtgtggtcg agggaagtt attcaggccg atgcatgtgg aaggcaagat agacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa atgggcgtt tcacggtgcc gaaaggagtt     660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccggag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata gctaacgcg cccttacatg gccagatgca tcagatgtgc agttgggagc    1080
tgccatagtc caatagcaat cgaggcagta agagcgacg ggcacgacgg ttatgttaga    1140
cttcagactt cctcgcagta tggcctggat tcctccggca acttaaaggg caggaccatg    1200
cggtatgaca tgcacgggac cattaaagag ataccactac atcaagtgtc actctataca    1260
tctcgcccgt gtcacattgt ggatgggcac ggttatttcc tgcttgccag gtgcccggca    1320
ggggactcca tcaccatgga atttaagaaa gattccgtca gacactcctg ctcggtgccg    1380
tatgaagtga aatttaatcc tgtaggcaga gaactctata tcatcccccc agaacacgga    1440
gtagagcaag cgtgccaagt ctacgcacat gatgcacaga cagaggagc ttatgtcgag    1500 atgcacctcc cgggctcaga agtggacagc agtttggttt ccttgagcgg cagttcagtc    1560
```

```
accgtgacac ctcctgatgg gactagcgcc ctggtggaat gtgagtgtgg cggcacaaag      1620
atctccgaga ccatcaacaa gacaaaacag ttcagccagt gcacaaagaa ggagcagtgc      1680
agagcatatc ggctgcagaa cgataagtgg gtgtataatt ctgacaaact gcccaaagca      1740
gcgggagcca ccttaaaagg aaaactgcat gtcccattct tgctggcaga cggcaaatgc      1800
accgtgcctc tagcaccaga acctatgata accttcggtt tcagatcagt gtcactgaaa      1860
ctgcacccta gaatcccac atatctaatc acccgccaac ttgctgatga gcctcactac      1920
acgcacgagc tcatatctga accagctgtt aggaatttta ccgtcaccga aaagggtgg       1980
gagtttgtat ggggaaacca cccgccgaaa aggttttggg cacaggaaac agcacccgga      2040
aatccacatg ggctaccgca cgaggtgata actcattatt accacagata ccctatgtcc      2100
accatcctgg gtttgtcaat ttgtgccgcc attgcaaccg tttccgttgc agcgtctacc      2160
tggctgtttt gcagatctag agttgcgtgc ctaactcctt accggctaac acctaacgct      2220
aggataccat tttgtctggc tgtgctttgc tgcgcccgca ctgcccgggc cgagaccacc      2280
tgggagtcct tggatcacct atggaacaat aaccaacaga tgttctggat tcaattgctg      2340
atccctctgg ccgccttgat cgtagtgact cgcctgctca ggtgcgtgtg ctgtgtcgtg      2400
cctttttag tcatggccgg cgccgcaggc gccggcgcct acgagcacgc gaccacgatg      2460
ccgagccaag cgggaatctc gtataacact atagtcaaca gagcaggcta cgcaccactc      2520
cctatcagca taacaccaac aaagatcaag ctgataccta cagtgaactt ggagtacgtc      2580
acctgccact acaaaacagg aatggattca ccagccatca aatgctgcgg atctcaggaa      2640
tgcactccaa cttacaggcc tgatgaacag tgcaaagtct tcacaggggt ttacccgttc      2700
atgtggggtg gtgcatattg cttttgcgac actgagaaca cccaagtcag caaggcctac      2760
gtaatgaaat ctgacgactg ccttgcggat catgctgaag catataaagc gcacacagcc      2820
tcagtgcagg cgttcctcaa catcacagtg ggagaacact ctattgtgac taccgtgtat      2880
gtgaatggag aaaactcctgt gaatttcaat ggggtcaaaa taactgcagg tccgctttcc      2940
acagcttgga caccctttga tcgcaaaatc gtgcagtatg ccggggagat ctataattat      3000
gattttcctg agtatgggc aggacaacca ggagcatttg gagatataca atccagaaca      3060
gtctcaagct ctgatctgta tgccaatacc aacctagtgc tgcagagacc caaagcagga      3120
gcgatccacg tgcctacac tcaggcacct tcgggttttg agcaatggaa gaaagataaa      3180
gctccatcat tgaaatttac cgccccttc ggatgcgaaa tatatacaaa ccccattcgc      3240
gccgaaaact gtgctgtagg gtcaattcca ttagccttg acattcccga cgccttgttc      3300
accagggtgt cagaaacacc gacactttca gcggccgagt gcactcttaa cgagtgcgtg      3360
tattcttccg actttggtgg gatcgccacg gtcaagtact cggccagcaa gtcaggcaag      3420
tgcgcagtcc atgtgccatc agggactgct accctaaaag aagcagcagt cgagctaacc      3480
gagcaagggt cggcgactat ccatttctcg accgcaaata tccacccgga gttcaggctc      3540
caaatatgca catcatatgt tacgtgcaaa ggtgattgtc accccccgaa agaccatatt      3600
gtgacacacc ctcagtatca cgcccaaaca tttacagccg cggtgtcaaa accgcgtgg      3660
acgtggttaa catccctgct gggaggatca gccgtaatta ttataattgg cttggtgctg      3720
gctactattg tggccatgta cgtgctgacc aaccagaaac ataatt              3766
```

<210> SEQ ID NO 20
<211> LENGTH: 11446
<212> TYPE: PRT
<213> ORGANISM: Artificial Sequence
<220> FEATURE:
<223> OTHER INFORMATION: VEEV CPD sequence

<400> SEQUENCE: 20

Ala Thr Ala Gly Gly Cys Gly Gly Cys Gly Cys Ala Thr Gly Ala Gly
1               5                   10                  15

Ala Gly Ala Ala Gly Cys Cys Cys Ala Gly Ala Cys Cys Ala Ala Thr
            20                  25                  30

Thr Ala Cys Cys Thr Ala Cys Cys Cys Ala Ala Ala Thr Gly Gly
        35                  40                  45

Ala Gly Ala Ala Ala Gly Thr Thr Cys Ala Cys Gly Thr Thr Gly Ala
        50                  55                  60

Cys Ala Thr Cys Gly Ala Gly Gly Ala Ala Gly Ala Cys Ala Gly Cys
65                  70                  75                  80

Cys Cys Ala Thr Thr Cys Cys Thr Cys Ala Gly Ala Gly Cys Thr Thr
                85                  90                  95

Thr Gly Cys Ala Gly Cys Gly Gly Ala Gly Cys Thr Thr Cys Cys Cys
            100                 105                 110

Gly Cys Ala Gly Thr Thr Thr Gly Ala Gly Gly Thr Ala Gly Ala Ala
            115                 120                 125

Gly Cys Cys Ala Ala Gly Cys Ala Gly Gly Thr Cys Ala Cys Thr Gly
            130                 135                 140

Ala Thr Ala Ala Thr Gly Ala Cys Cys Ala Thr Gly Cys Thr Ala Ala
145                 150                 155                 160

Thr Gly Cys Cys Ala Gly Ala Gly Cys Gly Thr Thr Thr Thr Cys Gly
            165                 170                 175

Cys Ala Thr Cys Thr Gly Gly Cys Thr Thr Cys Ala Ala Ala Ala Cys
            180                 185                 190

Thr Gly Ala Thr Cys Gly Ala Ala Ala Cys Gly Gly Ala Gly Gly Thr
            195                 200                 205

Gly Gly Ala Cys Cys Cys Ala Thr Cys Cys Gly Ala Cys Ala Cys Gly
            210                 215                 220

Ala Thr Cys Cys Thr Thr Gly Ala Cys Ala Thr Thr Gly Gly Ala Ala
225                 230                 235                 240

Gly Thr Gly Cys Gly Cys Cys Cys Cys Cys Gly Cys Cys Ala Gly
            245                 250                 255

Ala Ala Thr Gly Thr Ala Thr Thr Cys Thr Ala Ala Gly Cys Ala Cys
            260                 265                 270

Ala Ala Gly Thr Ala Thr Cys Ala Thr Thr Gly Thr Ala Thr Cys Thr
            275                 280                 285

Gly Thr Cys Cys Gly Ala Thr Gly Ala Gly Ala Thr Gly Thr Gly Cys
            290                 295                 300

Gly Gly Ala Ala Gly Ala Thr Cys Cys Gly Ala Cys Ala Gly Ala
305                 310                 315                 320

Thr Thr Gly Thr Ala Thr Ala Ala Gly Thr Ala Thr Gly Cys Ala Ala
            325                 330                 335

Cys Thr Ala Ala Gly Cys Thr Gly Ala Ala Gly Ala Ala Ala Ala
            340                 345                 350

Cys Thr Gly Thr Ala Ala Gly Gly Ala Ala Thr Ala Ala Cys Thr
            355                 360                 365

Gly Ala Thr Ala Ala Gly Gly Ala Ala Thr Thr Gly Gly Ala Cys Ala
            370                 375                 380

Ala Gly Ala Ala Ala Ala Thr Gly Ala Ala Gly Gly Ala Gly Cys Thr
385                 390                 395                 400

-continued

```
Gly Gly Cys Cys Gly Cys Cys Gly Thr Cys Ala Thr Gly Ala Gly Cys
                405                 410                 415

Gly Ala Cys Cys Cys Thr Gly Ala Cys Cys Thr Gly Gly Ala Ala Ala
            420                 425                 430

Cys Thr Gly Ala Gly Ala Cys Thr Ala Thr Gly Thr Gly Cys Cys Thr
        435                 440                 445

Cys Cys Ala Cys Gly Ala Cys Gly Ala Cys Gly Ala Gly Thr Cys Gly
    450                 455                 460

Thr Gly Thr Cys Gly Cys Thr Ala Cys Gly Ala Ala Gly Gly Gly Cys
465                 470                 475                 480

Ala Ala Gly Thr Cys Gly Cys Thr Gly Thr Thr Thr Ala Cys Cys Ala
                485                 490                 495

Gly Gly Ala Thr Gly Thr Ala Thr Ala Cys Gly Cys Gly Gly Thr Thr
            500                 505                 510

Gly Ala Cys Gly Gly Ala Cys Cys Gly Ala Cys Ala Ala Gly Thr Cys
        515                 520                 525

Thr Cys Thr Ala Thr Cys Ala Cys Cys Ala Ala Gly Cys Cys Ala Ala
    530                 535                 540

Thr Ala Ala Gly Gly Gly Ala Gly Thr Thr Ala Gly Ala Gly Thr Cys
545                 550                 555                 560

Gly Cys Cys Thr Ala Cys Thr Gly Gly Ala Thr Ala Gly Gly Cys Thr
                565                 570                 575

Thr Thr Gly Ala Cys Ala Cys Cys Ala Cys Cys Cys Cys Thr Thr Thr
            580                 585                 590

Thr Ala Thr Gly Thr Thr Thr Ala Ala Gly Ala Ala Cys Thr Thr Gly
        595                 600                 605

Gly Cys Thr Gly Gly Ala Gly Cys Ala Thr Ala Thr Cys Cys Ala Thr
    610                 615                 620

Cys Ala Thr Ala Cys Thr Cys Thr Ala Cys Cys Ala Ala Cys Thr Gly
625                 630                 635                 640

Gly Gly Cys Cys Gly Ala Cys Gly Ala Ala Ala Cys Cys Gly Thr Gly
                645                 650                 655

Thr Thr Ala Ala Cys Gly Gly Cys Thr Cys Gly Thr Ala Ala Cys Ala
            660                 665                 670

Thr Ala Gly Gly Cys Cys Thr Ala Thr Gly Cys Ala Gly Cys Thr Cys
        675                 680                 685

Thr Gly Ala Cys Gly Thr Thr Ala Thr Gly Gly Ala Gly Cys Gly Gly
    690                 695                 700

Thr Cys Ala Cys Gly Thr Ala Gly Ala Gly Gly Gly Ala Thr Gly Thr
705                 710                 715                 720

Cys Cys Ala Thr Thr Cys Thr Thr Ala Gly Ala Ala Ala Gly Ala Ala
                725                 730                 735

Gly Thr Ala Thr Thr Thr Gly Ala Ala Ala Cys Cys Ala Thr Cys Cys
            740                 745                 750

Ala Ala Cys Ala Ala Thr Gly Thr Thr Cys Thr Ala Thr Thr Cys Thr
        755                 760                 765

Cys Thr Gly Thr Thr Gly Gly Cys Thr Cys Gly Ala Cys Cys Ala Thr
    770                 775                 780

Cys Thr Ala Cys Cys Ala Cys Gly Ala Gly Ala Ala Gly Ala Gly Gly
785                 790                 795                 800

Gly Ala Cys Thr Thr Ala Cys Thr Gly Ala Gly Gly Ala Gly Cys Thr
                805                 810                 815
```

Gly Gly Cys Ala Cys Cys Thr Gly Cys Gly Thr Cys Thr Gly Thr
            820                 825                 830

Ala Thr Thr Thr Cys Ala Cys Thr Thr Ala Cys Gly Thr Gly Gly Cys
            835                 840                 845

Ala Ala Gly Cys Ala Ala Ala Thr Thr Ala Cys Ala Cys Ala Thr
            850                 855                 860

Gly Thr Cys Gly Gly Thr Gly Thr Gly Ala Gly Ala Cys Thr Ala Thr
865                 870                 875                 880

Ala Gly Thr Thr Ala Gly Thr Thr Gly Cys Gly Ala Cys Gly Gly Gly
            885                 890                 895

Thr Ala Cys Gly Thr Cys Gly Thr Thr Ala Ala Ala Gly Ala Ala
            900                 905                 910

Thr Ala Gly Cys Thr Ala Thr Cys Ala Gly Thr Cys Cys Ala Gly Gly
            915                 920                 925

Cys Cys Thr Gly Thr Ala Thr Gly Gly Gly Ala Ala Gly Cys Cys Thr
            930                 935                 940

Thr Cys Ala Gly Gly Cys Thr Ala Thr Gly Cys Thr Gly Cys Thr Ala
945                 950                 955                 960

Cys Gly Ala Thr Gly Cys Ala Cys Cys Gly Cys Gly Ala Gly Gly
            965                 970                 975

Ala Thr Thr Cys Thr Thr Gly Thr Gly Cys Thr Gly Cys Ala Ala Ala
            980                 985                 990

Gly Thr Gly Ala Cys Ala Gly Ala Cys Ala Cys Ala Thr Thr Gly Ala
            995                1000                1005

Ala Cys Gly Gly Gly Gly Ala Gly Ala Gly Gly Thr Cys Thr
            1010                1015                1020

Cys Thr Thr Thr Thr Cys Cys Gly Thr Gly Thr Gly Cys Ala
            1025                1030                1035

Cys Gly Thr Ala Thr Gly Thr Gly Cys Cys Ala Gly Cys Thr Ala
            1040                1045                1050

Cys Ala Thr Thr Gly Thr Gly Thr Gly Ala Cys Cys Ala Ala Ala
            1055                1060                1065

Thr Gly Ala Cys Thr Gly Gly Cys Ala Thr Ala Cys Thr Gly Gly
            1070                1075                1080

Cys Ala Ala Cys Ala Gly Ala Thr Gly Thr Cys Ala Gly Thr Gly
            1085                1090                1095

Cys Gly Gly Ala Cys Gly Ala Cys Gly Cys Gly Cys Ala Ala Ala
            1100                1105                1110

Ala Ala Cys Thr Gly Cys Thr Gly Gly Thr Gly Gly Gly Cys
            1115                1120                1125

Thr Cys Ala Ala Cys Cys Ala Gly Cys Gly Thr Ala Thr Ala Gly
            1130                1135                1140

Thr Cys Gly Thr Cys Ala Ala Cys Gly Gly Thr Cys Gly Cys Ala
            1145                1150                1155

Cys Cys Cys Ala Gly Ala Gly Ala Ala Ala Cys Ala Cys Cys Ala
            1160                1165                1170

Ala Thr Ala Cys Cys Ala Thr Gly Ala Ala Ala Ala Thr Thr
            1175                1180                1185

Ala Cys Cys Thr Thr Thr Thr Gly Cys Cys Cys Gly Thr Ala Gly
            1190                1195                1200

Thr Gly Gly Cys Cys Ala Gly Gly Cys Ala Thr Thr Gly
            1205                1210                1215

Cys Thr Ala Gly Gly Thr Gly Gly Gly Cys Ala Ala Ala Gly Gly

```
                     1220                1225                 1230

Ala Ala  Thr Ala Thr Ala Ala  Gly Gly Ala Ala Gly  Ala Thr Cys
         1235                1240                 1245

Ala Ala  Gly Ala Ala Gly Ala  Thr Gly Ala Ala Ala  Gly Gly Cys
         1250                1255                 1260

Cys Ala  Cys Thr Ala Gly Gly  Ala Cys Thr Ala Cys  Gly Ala Gly
         1265                1270                 1275

Ala Thr  Ala Gly Ala Cys Ala  Gly Thr Thr Ala Gly  Thr Cys Ala
         1280                1285                 1290

Thr Gly  Gly Gly Gly Thr Gly  Thr Thr Gly Thr Thr  Gly Gly Gly
         1295                1300                 1305

Cys Thr  Thr Thr Thr Ala Gly  Ala Ala Gly Gly Cys  Ala Cys Ala
         1310                1315                 1320

Ala Gly  Ala Thr Ala Ala Cys  Ala Thr Cys Thr Ala  Thr Thr Thr
         1325                1330                 1335

Ala Thr  Ala Ala Gly Cys Gly  Cys Cys Cys Gly Gly  Ala Thr Ala
         1340                1345                 1350

Cys Cys  Cys Ala Ala Ala Cys  Cys Ala Thr Cys Ala  Thr Cys Ala
         1355                1360                 1365

Ala Ala  Gly Thr Gly Ala Ala  Cys Ala Gly Cys Gly  Ala Thr Thr
         1370                1375                 1380

Thr Cys  Cys Ala Cys Thr Cys  Ala Thr Thr Cys Gly  Thr Gly Cys
         1385                1390                 1395

Thr Gly  Cys Cys Cys Ala Gly  Gly Ala Thr Ala Gly  Gly Cys Ala
         1400                1405                 1410

Gly Thr  Ala Ala Cys Ala Cys  Ala Thr Thr Gly Ala  Gly Ala Gly
         1415                1420                 1425

Thr Cys  Gly Gly Gly Cys Thr  Gly Ala Gly Ala Ala  Cys Ala Ala
         1430                1435                 1440

Gly Ala  Ala Thr Cys Ala Gly  Gly Ala Ala Ala Ala  Thr Gly Thr
         1445                1450                 1455

Thr Ala  Gly Ala Gly Gly Ala  Gly Cys Ala Cys Ala  Ala Gly Gly
         1460                1465                 1470

Ala Gly  Cys Cys Gly Thr Cys  Ala Cys Cys Thr Cys  Thr Cys Ala
         1475                1480                 1485

Thr Thr  Ala Cys Cys Gly Cys  Cys Gly Ala Gly Gly  Ala Cys Gly
         1490                1495                 1500

Thr Ala  Cys Ala Ala Gly Ala  Ala Gly Cys Thr Ala  Ala Gly Thr
         1505                1510                 1515

Gly Cys  Gly Cys Ala Gly Cys  Cys Gly Ala Thr Gly  Ala Gly Gly
         1520                1525                 1530

Cys Thr  Ala Ala Gly Gly Ala  Gly Gly Thr Gly Cys  Gly Thr Gly
         1535                1540                 1545

Ala Ala  Gly Cys Cys Gly Ala  Gly Gly Ala Gly Thr  Thr Gly Cys
         1550                1555                 1560

Gly Cys  Gly Cys Ala Gly Cys  Thr Cys Thr Ala Cys  Cys Ala Cys
         1565                1570                 1575

Cys Thr  Thr Thr Gly Gly Cys  Ala Gly Cys Thr Gly  Ala Thr Gly
         1580                1585                 1590

Thr Thr  Gly Ala Gly Gly Ala  Gly Cys Cys Cys Ala  Cys Thr Cys
         1595                1600                 1605

Thr Gly  Gly Ala Gly Gly Cys  Ala Gly Ala Cys Gly  Thr Cys Gly
         1610                1615                 1620
```

-continued

```
Ala Cys Thr Thr Gly Ala Thr Gly Thr Thr Ala Cys Ala Ala Gly
    1625                1630                1635

Ala Gly Gly Cys Thr Gly Gly Gly Gly Cys Cys Gly Gly Cys Thr
    1640                1645                1650

Cys Ala Gly Thr Gly Gly Ala Gly Ala Cys Ala Cys Cys Thr Cys
    1655                1660                1665

Gly Thr Gly Gly Cys Thr Thr Gly Ala Thr Ala Ala Ala Gly Gly
    1670                1675                1680

Thr Thr Ala Cys Cys Ala Gly Cys Thr Ala Cys Gly Ala Thr Gly
    1685                1690                1695

Gly Cys Gly Ala Gly Gly Ala Cys Ala Ala Gly Ala Thr Cys Gly
    1700                1705                1710

Gly Cys Thr Cys Thr Thr Ala Cys Gly Cys Thr Gly Thr Gly Cys
    1715                1720                1725

Thr Thr Thr Cys Thr Cys Cys Gly Cys Ala Gly Gly Cys Thr Gly
    1730                1735                1740

Thr Ala Cys Thr Cys Ala Ala Gly Ala Gly Thr Gly Ala Ala Ala
    1745                1750                1755

Ala Ala Thr Thr Ala Thr Cys Thr Thr Gly Cys Ala Thr Cys Cys
    1760                1765                1770

Ala Cys Cys Cys Thr Cys Thr Cys Gly Cys Thr Gly Ala Ala Cys
    1775                1780                1785

Ala Ala Gly Thr Cys Ala Thr Ala Gly Thr Gly Ala Thr Ala Ala
    1790                1795                1800

Cys Ala Cys Ala Cys Thr Cys Thr Gly Gly Cys Cys Gly Ala Ala
    1805                1810                1815

Ala Ala Gly Gly Gly Cys Gly Thr Thr Ala Thr Gly Cys Cys Gly
    1820                1825                1830

Thr Gly Gly Ala Ala Cys Cys Ala Thr Ala Cys Cys Ala Thr Gly
    1835                1840                1845

Gly Thr Ala Ala Ala Gly Thr Ala Gly Thr Gly Gly Thr Gly Cys
    1850                1855                1860

Cys Ala Gly Ala Gly Gly Gly Ala Cys Ala Thr Gly Cys Ala Ala
    1865                1870                1875

Thr Ala Cys Cys Cys Gly Thr Cys Cys Ala Gly Gly Ala Cys Thr
    1880                1885                1890

Thr Thr Cys Ala Ala Gly Cys Thr Cys Thr Gly Ala Gly Thr Gly
    1895                1900                1905

Ala Ala Ala Gly Thr Gly Cys Cys Ala Cys Cys Ala Thr Thr Gly
    1910                1915                1920

Thr Gly Thr Ala Cys Ala Ala Cys Gly Ala Ala Cys Gly Thr Gly
    1925                1930                1935

Ala Gly Thr Thr Cys Gly Thr Ala Ala Ala Cys Ala Gly Gly Thr
    1940                1945                1950

Ala Cys Cys Thr Gly Cys Ala Cys Cys Ala Thr Ala Thr Thr Gly
    1955                1960                1965

Cys Cys Ala Cys Ala Cys Ala Thr Gly Gly Ala Gly Gly Ala Gly
    1970                1975                1980

Cys Gly Cys Thr Gly Ala Ala Cys Ala Cys Thr Gly Ala Thr Gly
    1985                1990                1995

Ala Ala Gly Ala Ala Thr Ala Thr Thr Ala Cys Ala Ala Ala Ala
    2000                2005                2010
```

```
Cys Thr Gly Thr Cys Ala Ala Gly Cys Cys Cys Ala Gly Cys Gly
    2015                2020                2025

Ala Gly Cys Ala Cys Gly Ala Cys Gly Gly Cys Gly Ala Ala Thr
    2030                2035                2040

Ala Cys Cys Thr Gly Thr Ala Cys Gly Ala Cys Ala Thr Cys Gly
    2045                2050                2055

Ala Cys Ala Gly Gly Ala Ala Ala Cys Ala Gly Thr Gly Cys Gly
    2060                2065                2070

Thr Cys Ala Ala Gly Ala Ala Ala Gly Ala Ala Cys Thr Ala Gly
    2075                2080                2085

Thr Cys Ala Cys Thr Gly Gly Gly Cys Thr Ala Gly Gly Gly Cys
    2090                2095                2100

Thr Cys Ala Cys Ala Gly Gly Cys Gly Ala Gly Cys Thr Gly Gly
    2105                2110                2115

Thr Gly Gly Ala Thr Cys Cys Thr Cys Cys Cys Thr Thr Cys Cys
    2120                2125                2130

Ala Thr Gly Ala Ala Thr Thr Cys Gly Cys Cys Thr Ala Cys Gly
    2135                2140                2145

Ala Gly Ala Gly Thr Cys Thr Gly Ala Gly Ala Ala Cys Ala Cys
    2150                2155                2160

Gly Ala Cys Cys Ala Gly Cys Cys Gly Cys Thr Cys Cys Thr Thr
    2165                2170                2175

Ala Cys Cys Ala Ala Gly Thr Ala Cys Cys Ala Ala Cys Cys Ala
    2180                2185                2190

Thr Ala Gly Gly Gly Gly Thr Gly Thr Ala Thr Gly Gly Cys Gly
    2195                2200                2205

Thr Gly Cys Cys Ala Gly Gly Ala Thr Cys Ala Gly Gly Cys Ala
    2210                2215                2220

Ala Gly Thr Cys Thr Gly Gly Cys Ala Thr Cys Ala Thr Thr Ala
    2225                2230                2235

Ala Ala Ala Gly Cys Gly Cys Ala Gly Thr Cys Ala Cys Cys Ala
    2240                2245                2250

Ala Ala Ala Ala Ala Gly Ala Thr Cys Thr Ala Gly Thr Gly Gly
    2255                2260                2265

Thr Gly Ala Gly Cys Gly Cys Cys Ala Ala Gly Ala Ala Ala Gly
    2270                2275                2280

Ala Ala Ala Ala Cys Thr Gly Thr Gly Cys Ala Gly Ala Ala Ala
    2285                2290                2295

Thr Thr Ala Thr Ala Ala Gly Gly Ala Cys Gly Thr Cys Ala
    2300                2305                2310

Ala Gly Ala Ala Ala Ala Thr Gly Ala Ala Ala Gly Gly Gly Cys
    2315                2320                2325

Thr Gly Gly Ala Cys Gly Thr Cys Ala Ala Thr Gly Cys Cys Ala
    2330                2335                2340

Gly Ala Ala Cys Thr Gly Thr Gly Gly Ala Cys Thr Cys Ala Gly
    2345                2350                2355

Thr Gly Cys Thr Cys Thr Thr Gly Ala Ala Thr Gly Ala Thr Thr
    2360                2365                2370

Gly Cys Ala Ala Ala Cys Ala Cys Cys Cys Cys Gly Thr Ala Gly
    2375                2380                2385

Ala Gly Ala Cys Cys Cys Thr Gly Thr Ala Thr Ala Thr Thr Gly
    2390                2395                2400

Ala Cys Gly Ala Ala Gly Cys Thr Thr Thr Thr Gly Cys Thr Thr
```

-continued

```
            2405                2410                2415
Gly Thr Cys Ala Thr Gly Cys Ala Gly Gly Thr Ala Cys Thr Cys
            2420                2425                2430

Thr Cys Ala Gly Ala Gly Cys Gly Cys Thr Cys Ala Thr Ala Gly
            2435                2440                2445

Cys Cys Ala Thr Thr Ala Thr Ala Ala Gly Ala Cys Cys Thr Ala
            2450                2455                2460

Ala Ala Ala Ala Gly Gly Cys Ala Gly Thr Gly Cys Thr Cys Thr
            2465                2470                2475

Gly Cys Gly Gly Gly Ala Thr Cys Cys Cys Ala Ala Ala Ala Cys
            2480                2485                2490

Ala Gly Thr Gly Cys Gly Gly Thr Thr Thr Thr Thr Thr Thr Ala
            2495                2500                2505

Ala Cys Ala Thr Gly Ala Thr Gly Thr Gly Cys Cys Thr Gly Ala
            2510                2515                2520

Ala Ala Gly Thr Gly Cys Ala Thr Thr Thr Thr Ala Ala Cys Cys
            2525                2530                2535

Ala Cys Gly Ala Gly Ala Thr Thr Thr Gly Cys Ala Cys Ala Cys
            2540                2545                2550

Ala Ala Gly Thr Cys Thr Thr Cys Cys Ala Cys Ala Ala Ala Ala
            2555                2560                2565

Gly Cys Ala Thr Cys Thr Cys Thr Cys Gly Cys Cys Gly Thr Thr
            2570                2575                2580

Gly Cys Ala Cys Thr Ala Ala Ala Thr Cys Thr Gly Thr Gly Ala
            2585                2590                2595

Cys Thr Thr Cys Gly Gly Thr Cys Gly Thr Cys Thr Cys Ala Ala
            2600                2605                2610

Cys Cys Thr Thr Gly Thr Thr Thr Thr Ala Cys Gly Ala Cys Ala
            2615                2620                2625

Ala Ala Ala Ala Ala Ala Thr Gly Ala Gly Ala Ala Cys Gly Ala
            2630                2635                2640

Cys Gly Ala Ala Thr Cys Cys Gly Ala Ala Ala Gly Ala Gly Ala
            2645                2650                2655

Cys Thr Ala Ala Gly Ala Thr Thr Gly Thr Gly Ala Thr Thr Gly
            2660                2665                2670

Ala Cys Ala Cys Thr Ala Cys Cys Gly Gly Cys Ala Gly Thr Ala
            2675                2680                2685

Cys Cys Ala Ala Ala Cys Thr Ala Ala Gly Cys Ala Gly Gly
            2690                2695                2700

Ala Cys Gly Ala Thr Cys Thr Cys Ala Thr Thr Cys Thr Cys Ala
            2705                2710                2715

Cys Thr Thr Gly Thr Thr Thr Cys Ala Gly Ala Gly Gly Gly Thr
            2720                2725                2730

Gly Gly Gly Thr Gly Ala Ala Gly Cys Ala Gly Thr Thr Gly Cys
            2735                2740                2745

Ala Ala Ala Thr Ala Gly Ala Thr Thr Ala Cys Ala Ala Ala Gly
            2750                2755                2760

Gly Cys Ala Ala Cys Gly Ala Ala Ala Thr Ala Ala Thr Gly Ala
            2765                2770                2775

Cys Gly Gly Cys Ala Gly Cys Thr Gly Cys Cys Thr Cys Thr Cys
            2780                2785                2790

Ala Ala Gly Gly Gly Cys Thr Gly Ala Cys Cys Cys Gly Thr Ala
            2795                2800                2805
```

```
Ala Ala Gly Gly Thr Gly Thr Gly Thr Ala Thr Gly Cys Cys Gly
2810                2815                2820

Thr Thr Cys Gly Gly Thr Ala Cys Ala Ala Gly Thr Gly Ala
    2825                2830                2835

Ala Thr Gly Ala Ala Ala Ala Thr Cys Cys Thr Cys Thr Gly Thr
    2840                2845                2850

Ala Cys Gly Cys Ala Cys Cys Ala Cys Cys Thr Cys Ala Gly
    2855                2860                2865

Ala Ala Cys Ala Thr Gly Thr Gly Ala Ala Cys Gly Thr Cys Cys
    2870                2875                2880

Thr Ala Cys Thr Gly Ala Cys Cys Cys Gly Cys Ala Cys Gly Gly
    2885                2890                2895

Ala Gly Gly Ala Cys Cys Gly Cys Ala Thr Cys Gly Thr Gly Thr
    2900                2905                2910

Gly Gly Ala Ala Ala Ala Cys Ala Cys Thr Ala Gly Cys Cys Gly
    2915                2920                2925

Gly Cys Gly Ala Cys Cys Ala Thr Gly Gly Ala Thr Ala Ala
    2930                2935                2940

Ala Ala Ala Cys Ala Cys Thr Gly Ala Cys Thr Gly Cys Cys Ala
    2945                2950                2955

Ala Gly Thr Ala Cys Cys Thr Gly Gly Gly Ala Ala Thr Thr
    2960                2965                2970

Thr Cys Ala Cys Thr Gly Cys Cys Ala Cys Gly Ala Thr Ala Gly
    2975                2980                2985

Ala Gly Gly Ala Gly Thr Gly Gly Cys Ala Ala Gly Cys Ala Gly
    2990                2995                3000

Ala Gly Cys Ala Thr Gly Ala Thr Gly Cys Cys Ala Thr Cys Ala
    3005                3010                3015

Thr Gly Ala Gly Gly Cys Ala Cys Ala Thr Cys Thr Thr Gly Gly
    3020                3025                3030

Ala Gly Ala Gly Ala Cys Cys Gly Gly Ala Cys Cys Cys Thr Ala
    3035                3040                3045

Cys Cys Gly Ala Cys Gly Thr Cys Thr Thr Cys Cys Ala Gly Ala
    3050                3055                3060

Ala Thr Ala Ala Gly Gly Cys Ala Ala Ala Cys Gly Thr Gly Thr
    3065                3070                3075

Gly Thr Thr Gly Gly Gly Cys Cys Ala Ala Gly Gly Cys Thr Thr
    3080                3085                3090

Thr Ala Gly Thr Gly Cys Cys Gly Gly Thr Gly Cys Thr Gly Ala
    3095                3100                3105

Ala Gly Ala Cys Cys Gly Cys Thr Gly Gly Cys Ala Thr Ala Gly
    3110                3115                3120

Ala Cys Ala Thr Gly Ala Cys Ala Cys Thr Gly Ala Ala Cys
    3125                3130                3135

Ala Ala Thr Gly Gly Ala Ala Cys Ala Cys Thr Thr Gly Gly
    3140                3145                3150

Ala Thr Thr Ala Thr Thr Thr Gly Ala Ala Ala Cys Gly Gly
    3155                3160                3165

Ala Cys Ala Ala Ala Gly Cys Thr Cys Ala Cys Thr Cys Ala Gly
    3170                3175                3180

Cys Ala Gly Ala Gly Ala Thr Ala Gly Thr Ala Thr Thr Gly Ala
    3185                3190                3195
```

```
Ala Cys  Cys Ala Ala Cys Thr  Ala Thr Gly Cys Gly  Thr Gly Ala
    3200                 3205                 3210

Gly Gly  Thr Thr Cys Thr Thr  Thr Gly Gly Ala Cys  Thr Cys Gly
    3215                 3220                 3225

Ala Thr  Cys Thr Gly Gly Ala  Cys Thr Cys Cys Gly  Gly Thr Cys
    3230                 3235                 3240

Thr Ala  Thr Thr Thr Thr Cys  Thr Gly Cys Ala Cys  Cys Cys Ala
    3245                 3250                 3255

Cys Thr  Gly Thr Thr Cys Cys  Gly Thr Thr Ala Thr  Cys Cys Ala
    3260                 3265                 3270

Thr Thr  Ala Gly Gly Ala Ala  Thr Ala Ala Thr Cys  Ala Cys Thr
    3275                 3280                 3285

Gly Gly  Gly Ala Thr Ala Ala  Cys Thr Cys Cys Cys  Cys Gly Thr
    3290                 3295                 3300

Cys Gly  Cys Cys Thr Ala Ala  Cys Ala Thr Gly Thr  Ala Cys Gly
    3305                 3310                 3315

Gly Gly  Cys Thr Gly Ala Ala  Thr Ala Ala Ala Gly  Ala Ala Gly
    3320                 3325                 3330

Thr Gly  Gly Thr Cys Cys Gly  Thr Cys Ala Gly Cys  Thr Cys Thr
    3335                 3340                 3345

Cys Thr  Cys Gly Cys Ala Gly  Gly Thr Ala Cys Cys  Cys Ala Cys
    3350                 3355                 3360

Ala Ala  Cys Thr Gly Cys Cys  Thr Cys Gly Gly Gly  Cys Ala Gly
    3365                 3370                 3375

Thr Thr  Gly Cys Cys Ala Cys  Thr Gly Gly Ala Ala  Gly Ala Gly
    3380                 3385                 3390

Thr Cys  Thr Ala Thr Gly Ala  Cys Ala Thr Gly Ala  Ala Cys Ala
    3395                 3400                 3405

Cys Thr  Gly Gly Thr Ala Cys  Ala Cys Thr Gly Cys  Gly Cys Ala
    3410                 3415                 3420

Ala Thr  Thr Ala Thr Gly Ala  Thr Cys Cys Gly Cys  Gly Cys Ala
    3425                 3430                 3435

Thr Ala  Ala Ala Cys Cys Thr  Ala Gly Thr Ala Cys  Cys Thr Gly
    3440                 3445                 3450

Thr Ala  Ala Ala Cys Ala Gly  Ala Ala Gly Ala Cys  Thr Gly Cys
    3455                 3460                 3465

Cys Thr  Cys Ala Thr Gly Cys  Thr Thr Thr Ala Gly  Thr Cys Cys
    3470                 3475                 3480

Thr Cys  Cys Ala Cys Cys Ala  Thr Ala Ala Thr Gly  Ala Ala Cys
    3485                 3490                 3495

Ala Cys  Cys Cys Ala Cys Ala  Gly Ala Gly Thr Gly  Ala Cys Thr
    3500                 3505                 3510

Thr Thr  Thr Cys Thr Thr Cys  Ala Thr Thr Cys Gly  Thr Cys Ala
    3515                 3520                 3525

Gly Cys  Ala Ala Ala Thr Thr  Gly Ala Ala Gly Gly  Gly Cys Ala
    3530                 3535                 3540

Gly Ala  Ala Cys Thr Gly Thr  Cys Cys Thr Gly Gly  Thr Gly Gly
    3545                 3550                 3555

Thr Cys  Gly Gly Gly Gly Ala  Ala Ala Ala Gly Thr  Thr Gly Thr
    3560                 3565                 3570

Cys Cys  Gly Thr Cys Cys Cys  Ala Gly Gly Cys Ala  Ala Ala Ala
    3575                 3580                 3585

Thr Gly  Gly Thr Thr Gly Ala  Cys Thr Gly Gly Thr  Thr Gly Thr
```

```
    3590                3595                3600

Cys Ala  Gly Ala Cys Cys Gly  Gly Cys Cys Thr Gly  Ala Gly Gly
    3605                3610                3615

Cys Thr  Ala Cys Cys Thr Thr  Cys Ala Gly Ala Gly  Cys Thr Cys
    3620                3625                3630

Gly Gly  Cys Thr Gly Gly Ala  Thr Thr Thr Ala Gly  Gly Cys Ala
    3635                3640                3645

Thr Cys  Cys Cys Ala Gly Gly  Thr Gly Ala Thr Gly  Thr Gly Cys
    3650                3655                3660

Cys Cys  Ala Ala Ala Thr Ala  Thr Gly Ala Cys Ala  Thr Ala Ala
    3665                3670                3675

Thr Ala  Thr Thr Thr Gly Thr  Thr Ala Ala Thr Gly  Thr Gly Ala
    3680                3685                3690

Gly Gly  Ala Cys Cys Cys Cys  Ala Thr Ala Thr Ala  Ala Ala Thr
    3695                3700                3705

Ala Cys  Cys Ala Thr Cys Ala  Cys Thr Ala Thr Cys  Ala Gly Cys
    3710                3715                3720

Ala Gly  Thr Gly Thr Gly Ala  Ala Gly Ala Cys Cys  Ala Thr Gly
    3725                3730                3735

Cys Cys  Ala Thr Thr Ala Ala  Gly Cys Thr Thr Ala  Gly Cys Ala
    3740                3745                3750

Thr Gly  Thr Thr Gly Ala Cys  Cys Ala Ala Gly Ala  Ala Ala Gly
    3755                3760                3765

Cys Thr  Thr Gly Thr Cys Thr  Gly Cys Ala Thr Cys  Thr Gly Ala
    3770                3775                3780

Ala Thr  Cys Cys Cys Gly Gly  Cys Gly Gly Ala Ala  Cys Cys Thr
    3785                3790                3795

Gly Thr  Gly Thr Cys Ala Gly  Cys Ala Thr Ala Gly  Gly Thr Thr
    3800                3805                3810

Ala Thr  Gly Gly Thr Thr Ala  Cys Gly Cys Thr Gly  Ala Cys Ala
    3815                3820                3825

Gly Gly  Gly Cys Cys Ala Gly  Cys Gly Ala Ala Ala  Gly Cys Ala
    3830                3835                3840

Thr Cys  Ala Thr Thr Gly Gly  Thr Gly Cys Thr Ala  Thr Ala Gly
    3845                3850                3855

Cys Gly  Cys Gly Gly Cys Ala  Gly Thr Thr Cys Ala  Ala Gly Thr
    3860                3865                3870

Thr Thr  Thr Cys Cys Cys Gly  Gly Gly Thr Ala Thr  Gly Cys Ala
    3875                3880                3885

Ala Ala  Cys Cys Gly Ala Ala  Ala Thr Cys Cys Thr  Cys Ala Cys
    3890                3895                3900

Thr Thr  Gly Ala Ala Gly Ala  Gly Ala Cys Gly Gly  Ala Ala Gly
    3905                3910                3915

Thr Thr  Cys Thr Gly Thr Thr  Thr Gly Thr Ala Thr  Thr Cys Ala
    3920                3925                3930

Thr Thr  Gly Gly Gly Thr Ala  Cys Gly Ala Thr Cys  Gly Cys Ala
    3935                3940                3945

Ala Gly  Gly Cys Cys Cys Gly  Thr Ala Cys Gly Cys  Ala Cys Ala
    3950                3955                3960

Ala Thr  Cys Cys Thr Thr Ala  Cys Ala Ala Gly Cys  Thr Thr Thr
    3965                3970                3975

Cys Ala  Thr Cys Ala Ala Cys  Cys Thr Thr Gly Ala  Cys Cys Ala
    3980                3985                3990
```

```
Ala Cys Ala Thr Thr Thr Ala Thr Ala Cys Ala Gly Gly Thr Thr
    3995                4000                4005
Cys Cys Ala Gly Ala Cys Thr Cys Cys Ala Cys Gly Ala Ala Gly
    4010                4015                4020
Cys Cys Gly Gly Ala Thr Gly Thr Gly Cys Ala Cys Cys Cys Thr
    4025                4030                4035
Cys Ala Thr Ala Thr Cys Ala Thr Gly Thr Gly Thr Gly Thr Cys
    4040                4045                4050
Gly Ala Gly Gly Gly Gly Ala Thr Ala Thr Gly Cys Cys Ala
    4055                4060                4065
Cys Gly Gly Cys Cys Ala Cys Cys Gly Ala Ala Gly Gly Ala Gly
    4070                4075                4080
Thr Gly Ala Thr Thr Ala Thr Ala Ala Ala Thr Gly Cys Thr Gly
    4085                4090                4095
Cys Thr Ala Ala Cys Ala Gly Cys Ala Ala Gly Gly Ala Cys
    4100                4105                4110
Ala Ala Cys Cys Thr Gly Gly Cys Gly Gly Ala Gly Gly Gly Gly
    4115                4120                4125
Thr Gly Thr Gly Cys Gly Gly Ala Gly Cys Gly Cys Thr Gly Thr
    4130                4135                4140
Ala Thr Ala Ala Gly Ala Ala Ala Thr Thr Cys Cys Cys Gly Gly
    4145                4150                4155
Ala Ala Ala Gly Cys Thr Thr Cys Gly Ala Thr Thr Thr Ala Cys
    4160                4165                4170
Ala Gly Cys Cys Gly Ala Thr Cys Gly Ala Ala Gly Thr Ala Gly
    4175                4180                4185
Gly Ala Ala Ala Gly Cys Gly Cys Gly Ala Cys Thr Gly Gly
    4190                4195                4200
Thr Cys Ala Ala Ala Gly Gly Thr Gly Cys Ala Gly Cys Thr Ala
    4205                4210                4215
Ala Ala Cys Ala Thr Ala Thr Cys Ala Thr Thr Cys Ala Thr Gly
    4220                4225                4230
Cys Cys Gly Thr Ala Gly Gly Ala Cys Cys Ala Ala Ala Cys Thr
    4235                4240                4245
Thr Cys Ala Ala Cys Ala Ala Ala Gly Thr Thr Thr Cys Gly Gly
    4250                4255                4260
Ala Gly Gly Thr Thr Gly Ala Ala Gly Gly Thr Gly Ala Cys Ala
    4265                4270                4275
Ala Ala Cys Ala Gly Thr Thr Gly Gly Cys Ala Gly Ala Gly Gly
    4280                4285                4290
Cys Thr Thr Ala Thr Gly Ala Gly Thr Cys Cys Ala Thr Cys Gly
    4295                4300                4305
Cys Thr Ala Ala Gly Ala Thr Gly Thr Cys Ala Ala Cys Gly
    4310                4315                4320
Ala Thr Ala Ala Cys Ala Ala Thr Thr Ala Cys Ala Ala Gly Thr
    4325                4330                4335
Cys Ala Gly Thr Ala Gly Cys Gly Ala Thr Thr Cys Cys Ala Cys
    4340                4345                4350
Thr Gly Thr Thr Gly Thr Cys Cys Ala Cys Cys Gly Gly Cys Ala
    4355                4360                4365
Thr Cys Thr Thr Thr Thr Cys Cys Gly Gly Gly Ala Ala Cys Ala
    4370                4375                4380
```

| | | | | | | | | | | | | | |
|---|---|---|---|---|---|---|---|---|---|---|---|---|---|
|Ala|Ala|Gly|Ala|Thr|Cys|Gly|Ala|Cys|Thr|Ala|Ala|Cys|Cys Cys|
| |4385| | | |4390| | | |4395| | | | |
|Ala|Ala|Thr|Cys|Ala|Thr|Thr|Gly|Ala|Ala|Cys|Cys|Ala|Thr Thr|
| |4400| | | |4405| | | |4410| | | | |
|Thr|Gly|Cys|Thr|Gly|Ala|Cys|Ala|Gly|Cys|Thr|Thr|Thr|Ala Gly|
| |4415| | | |4420| | | |4425| | | | |
|Ala|Cys|Ala|Cys|Cys|Ala|Cys|Thr|Gly|Ala|Thr|Gly|Cys|Ala Gly|
| |4430| | | |4435| | | |4440| | | | |
|Ala|Thr|Gly|Thr|Ala|Gly|Cys|Cys|Ala|Thr|Ala|Thr|Ala|Cys Thr|
| |4445| | | |4450| | | |4455| | | | |
|Gly|Cys|Ala|Gly|Gly|Gly|Ala|Cys|Ala|Ala|Gly|Ala|Ala|Ala Thr|
| |4460| | | |4465| | | |4470| | | | |
|Gly|Gly|Gly|Ala|Ala|Ala|Thr|Gly|Ala|Cys|Thr|Cys|Thr|Cys Ala|
| |4475| | | |4480| | | |4485| | | | |
|Ala|Gly|Gly|Ala|Ala|Gly|Cys|Ala|Gly|Thr|Gly|Gly|Cys|Thr Ala|
| |4490| | | |4495| | | |4500| | | | |
|Gly|Gly|Ala|Gly|Ala|Gly|Ala|Ala|Gly|Cys|Ala|Gly|Thr|Gly Gly|
| |4505| | | |4510| | | |4515| | | | |
|Ala|Gly|Gly|Ala|Gly|Ala|Thr|Ala|Thr|Gly|Cys|Ala|Thr|Ala Thr|
| |4520| | | |4525| | | |4530| | | | |
|Cys|Cys|Gly|Ala|Cys|Gly|Ala|Cys|Thr|Cys|Thr|Thr|Cys|Ala Gly|
| |4535| | | |4540| | | |4545| | | | |
|Thr|Gly|Ala|Cys|Ala|Gly|Ala|Ala|Cys|Cys|Thr|Gly|Ala|Thr Gly|
| |4550| | | |4555| | | |4560| | | | |
|Cys|Ala|Gly|Ala|Gly|Cys|Thr|Gly|Gly|Thr|Gly|Ala|Gly|Gly Gly|
| |4565| | | |4570| | | |4575| | | | |
|Thr|Gly|Cys|Ala|Thr|Cys|Cys|Gly|Ala|Ala|Gly|Ala|Gly|Thr Thr|
| |4580| | | |4585| | | |4590| | | | |
|Cys|Thr|Thr|Thr|Gly|Gly|Cys|Thr|Gly|Gly|Ala|Ala|Gly|Gly Ala|
| |4595| | | |4600| | | |4605| | | | |
|Ala|Gly|Gly|Gly|Cys|Thr|Ala|Cys|Ala|Gly|Cys|Ala|Cys|Ala Ala|
| |4610| | | |4615| | | |4620| | | | |
|Gly|Cys|Gly|Ala|Thr|Gly|Gly|Cys|Ala|Ala|Ala|Ala|Cys|Thr Thr|
| |4625| | | |4630| | | |4635| | | | |
|Thr|Cys|Thr|Cys|Ala|Thr|Ala|Thr|Thr|Thr|Gly|Gly|Ala|Ala Gly|
| |4640| | | |4645| | | |4650| | | | |
|Gly|Gly|Ala|Cys|Cys|Ala|Ala|Gly|Thr|Thr|Thr|Cys|Ala|Cys Cys|
| |4655| | | |4660| | | |4665| | | | |
|Ala|Gly|Gly|Cys|Gly|Gly|Cys|Cys|Ala|Ala|Gly|Gly|Ala|Thr Ala|
| |4670| | | |4675| | | |4680| | | | |
|Thr|Ala|Gly|Cys|Ala|Gly|Ala|Ala|Ala|Thr|Thr|Ala|Ala|Thr Gly|
| |4685| | | |4690| | | |4695| | | | |
|Cys|Cys|Ala|Thr|Gly|Thr|Gly|Gly|Cys|Cys|Gly|Thr|Thr|Gly|
| |4700| | | |4705| | | |4710| | | | |
|Cys|Ala|Ala|Cys|Gly|Gly|Ala|Gly|Gly|Cys|Cys|Ala|Ala|Thr Gly|
| |4715| | | |4720| | | |4725| | | | |
|Ala|Gly|Cys|Ala|Gly|Gly|Thr|Ala|Thr|Gly|Cys|Ala|Thr|Gly Thr|
| |4730| | | |4735| | | |4740| | | | |
|Ala|Thr|Ala|Thr|Cys|Cys|Thr|Cys|Gly|Gly|Ala|Gly|Ala|Ala Ala|
| |4745| | | |4750| | | |4755| | | | |
|Gly|Cys|Ala|Thr|Gly|Ala|Gly|Cys|Ala|Gly|Thr|Ala|Thr|Thr Ala|
| |4760| | | |4765| | | |4770| | | | |
|Gly|Gly|Thr|Cys|Gly|Ala|Ala|Ala|Thr|Gly|Cys|Cys|Cys|Cys Gly|

-continued

```
            4775                4780                4785
Thr Cys Gly Ala Ala Gly Ala Gly Thr Cys Gly Ala Ala Gly
        4790                4795                4800
Cys Cys Thr Cys Cys Ala Cys Ala Cys Ala Cys Cys Thr Ala
        4805                4810                4815
Gly Cys Ala Cys Gly Cys Thr Gly Cys Cys Thr Thr Gly Cys Thr
        4820                4825                4830
Thr Gly Thr Gly Cys Ala Thr Cys Cys Ala Thr Gly Cys Cys Ala
        4835                4840                4845
Thr Gly Ala Cys Thr Cys Cys Ala Gly Ala Ala Ala Gly Ala Gly
        4850                4855                4860
Thr Ala Cys Ala Gly Cys Gly Cys Cys Thr Ala Ala Ala Ala Gly
        4865                4870                4875
Cys Cys Thr Cys Ala Cys Gly Thr Cys Cys Ala Gly Ala Ala Cys
        4880                4885                4890
Ala Ala Ala Thr Thr Ala Cys Thr Gly Thr Gly Thr Gly Cys Thr
        4895                4900                4905
Cys Ala Thr Cys Cys Thr Thr Thr Cys Cys Ala Thr Thr Gly Cys
        4910                4915                4920
Cys Gly Ala Ala Gly Thr Ala Thr Ala Gly Ala Ala Thr Cys Ala
        4925                4930                4935
Cys Thr Gly Gly Thr Gly Thr Gly Cys Ala Gly Ala Ala Gly Ala
        4940                4945                4950
Thr Cys Cys Ala Ala Thr Gly Cys Thr Cys Cys Ala Gly Cys
        4955                4960                4965
Cys Thr Ala Thr Ala Thr Thr Gly Thr Thr Cys Thr Cys Ala Cys
        4970                4975                4980
Cys Gly Ala Ala Ala Gly Thr Gly Cys Cys Thr Gly Cys Gly Thr
        4985                4990                4995
Ala Thr Ala Thr Thr Cys Ala Thr Cys Cys Ala Ala Gly Gly Ala
        5000                5005                5010
Ala Gly Thr Ala Thr Cys Thr Cys Gly Thr Gly Gly Ala Ala Ala
        5015                5020                5025
Cys Ala Cys Cys Ala Cys Cys Gly Gly Thr Ala Gly Ala Cys Gly
        5030                5035                5040
Ala Gly Ala Cys Thr Cys Cys Gly Gly Ala Gly Cys Cys Ala Thr
        5045                5050                5055
Cys Gly Gly Cys Ala Gly Ala Gly Ala Ala Cys Cys Ala Ala Thr
        5060                5065                5070
Cys Cys Ala Cys Ala Gly Ala Gly Gly Gly Gly Ala Cys Ala Cys
        5075                5080                5085
Cys Thr Gly Ala Ala Cys Ala Ala Cys Cys Ala Cys Cys Ala Cys
        5090                5095                5100
Thr Thr Ala Thr Ala Ala Cys Cys Gly Ala Gly Gly Ala Thr Gly
        5105                5110                5115
Ala Gly Ala Cys Cys Ala Gly Gly Ala Cys Thr Ala Gly Ala Ala
        5120                5125                5130
Cys Gly Cys Cys Thr Gly Ala Gly Cys Cys Gly Ala Thr Cys Ala
        5135                5140                5145
Thr Cys Ala Thr Cys Gly Ala Ala Gly Ala Gly Ala Ala Gly
        5150                5155                5160
Ala Ala Gly Ala Gly Gly Ala Thr Ala Gly Cys Ala Thr Ala Ala
        5165                5170                5175
```

Gly Thr Thr Thr Gly Cys Thr Gly Thr Cys Ala Gly Ala Thr Gly
            5180            5185                5190

Gly Cys Cys Cys Gly Ala Cys Cys Cys Ala Cys Cys Ala Gly Gly
            5195            5200                5205

Thr Gly Cys Thr Gly Cys Ala Ala Gly Thr Cys Gly Ala Gly Gly
            5210            5215                5220

Cys Ala Gly Ala Cys Ala Thr Thr Cys Ala Cys Gly Gly Gly Cys
            5225            5230                5235

Cys Gly Cys Cys Cys Thr Cys Thr Gly Thr Ala Thr Cys Thr Ala
            5240            5245                5250

Gly Cys Thr Cys Ala Thr Cys Cys Thr Gly Gly Thr Cys Cys Ala
            5255            5260                5265

Thr Thr Cys Cys Thr Cys Ala Thr Gly Cys Ala Thr Cys Cys Gly
            5270            5275                5280

Ala Cys Thr Thr Thr Gly Ala Thr Gly Thr Gly Gly Ala Cys Ala
            5285            5290                5295

Gly Thr Thr Thr Ala Thr Cys Cys Ala Thr Ala Cys Thr Thr Gly
            5300            5305                5310

Ala Cys Ala Cys Cys Cys Thr Gly Gly Ala Gly Gly Gly Ala Gly
5315 5320 5325

Cys Thr Ala Gly Cys Gly Thr Gly Ala Cys Cys Ala Gly Cys Gly
5330 5335 5340

Gly Gly Gly Cys Ala Ala Cys Gly Thr Cys Ala Gly Cys Cys Gly
5345 5350 5355

Ala Gly Ala Cys Thr Ala Ala Cys Thr Cys Thr Thr Ala Cys Thr
5360 5365 5370

Thr Cys Gly Cys Ala Ala Ala Gly Ala Gly Thr Ala Thr Gly Gly
5375 5380 5385

Ala Gly Thr Thr Thr Cys Thr Gly Gly Cys Gly Cys Gly Ala Cys
5390 5395 5400

Cys Gly Gly Thr Gly Cys Cys Thr Gly Cys Gly Cys Cys Thr Cys
5405 5410 5415

Gly Ala Ala Cys Ala Gly Thr Ala Thr Thr Cys Ala Gly Gly Ala
5420 5425 5430

Ala Cys Cys Cys Thr Cys Cys Ala Cys Ala Thr Cys Cys Cys Gly
5435 5440 5445

Cys Thr Cys Cys Gly Cys Gly Cys Ala Cys Ala Ala Gly Ala Ala
5450 5455 5460

Cys Ala Cys Cys Gly Thr Cys Ala Cys Thr Thr Gly Cys Ala Cys
5465 5470 5475

Cys Cys Ala Gly Cys Ala Gly Gly Gly Cys Cys Thr Gly Cys Thr
5480 5485 5490

Cys Gly Ala Gly Ala Ala Cys Cys Ala Gly Cys Cys Thr Ala Gly
5495 5500 5505

Thr Thr Thr Cys Cys Ala Cys Cys Cys Cys Gly Cys Cys Ala Gly
5510 5515 5520

Gly Cys Gly Thr Gly Ala Ala Thr Ala Gly Gly Gly Thr Gly Ala
5525 5530 5535

Thr Cys Ala Cys Thr Ala Gly Ala Gly Ala Gly Gly Ala Gly Cys
5540 5545 5550

Thr Cys Gly Ala Gly Gly Cys Gly Cys Thr Thr Ala Cys Cys Cys
5555 5560 5565

-continued

```
Cys Gly  Thr Cys Ala Cys Gly  Cys Ala Cys Thr Cys  Cys Thr Ala
    5570                 5575                 5580

Gly Cys  Ala Gly Gly Thr Cys  Gly Gly Thr Cys Thr  Cys Gly Ala
    5585                 5590                 5595

Gly Ala  Ala Cys Cys Ala Gly  Cys Cys Thr Gly Gly  Thr Cys Thr
    5600                 5605                 5610

Cys Cys  Ala Ala Cys Cys Cys  Gly Cys Cys Ala Gly  Gly Cys Gly
    5615                 5620                 5625

Thr Ala  Ala Ala Thr Ala Gly  Gly Gly Thr Gly Ala  Thr Thr Ala
    5630                 5635                 5640

Cys Ala  Ala Gly Ala Gly Ala  Gly Gly Ala Gly Thr  Thr Thr Gly
    5645                 5650                 5655

Ala Gly  Gly Cys Gly Thr Thr  Cys Gly Thr Ala Gly  Cys Ala Cys
    5660                 5665                 5670

Ala Ala  Cys Ala Ala Cys Ala  Ala Thr Gly Ala Cys  Gly Gly Thr
    5675                 5680                 5685

Thr Thr  Gly Ala Thr Gly Cys  Gly Gly Gly Thr Gly  Cys Ala Thr
    5690                 5695                 5700

Ala Cys  Ala Thr Cys Thr Thr  Thr Thr Cys Cys Thr  Cys Cys Gly
    5705                 5710                 5715

Ala Cys  Ala Cys Cys Gly Gly  Thr Cys Ala Ala Gly  Gly Gly Cys
    5720                 5725                 5730

Ala Thr  Thr Thr Ala Cys Ala  Ala Cys Ala Ala Ala  Ala Ala Thr
    5735                 5740                 5745

Cys Ala  Gly Thr Ala Ala Gly  Gly Cys Ala Ala Ala  Cys Gly Gly
    5750                 5755                 5760

Thr Gly  Cys Thr Ala Thr Cys  Cys Gly Ala Ala Gly  Thr Gly Gly
    5765                 5770                 5775

Thr Gly  Thr Thr Gly Gly Ala  Gly Ala Gly Gly Ala  Cys Cys Gly
    5780                 5785                 5790

Ala Ala  Thr Thr Gly Gly Ala  Gly Ala Thr Thr Thr  Cys Gly Thr
    5795                 5800                 5805

Ala Thr  Gly Cys Cys Cys Cys  Gly Cys Gly Cys Cys  Thr Cys Gly
    5810                 5815                 5820

Ala Cys  Cys Ala Ala Gly Ala  Ala Ala Ala Ala Gly  Ala Ala Gly
    5825                 5830                 5835

Ala Ala  Thr Thr Ala Cys Thr  Ala Cys Gly Cys Ala  Ala Gly Ala
    5840                 5845                 5850

Ala Ala  Thr Thr Ala Cys Ala  Gly Thr Thr Ala Ala  Ala Thr Cys
    5855                 5860                 5865

Cys Cys  Ala Cys Ala Cys Cys  Thr Gly Cys Thr Ala  Ala Cys Ala
    5870                 5875                 5880

Gly Ala  Ala Gly Cys Ala Gly  Ala Thr Ala Cys Cys  Ala Gly Thr
    5885                 5890                 5895

Cys Cys  Ala Gly Gly Ala Ala  Gly Gly Thr Gly Gly  Ala Gly Ala
    5900                 5905                 5910

Ala Cys  Ala Thr Gly Ala Ala  Ala Gly Cys Cys Ala  Thr Ala Ala
    5915                 5920                 5925

Cys Ala  Gly Cys Thr Ala Gly  Ala Cys Gly Thr Ala  Thr Thr Cys
    5930                 5935                 5940

Thr Gly  Cys Ala Ala Gly Gly  Cys Cys Thr Ala Gly  Gly Gly Cys
    5945                 5950                 5955

Ala Thr  Thr Ala Thr Thr Thr  Gly Ala Ala Gly Gly  Cys Ala Gly
```

|   |   |   |   |   |   |   |   |   |   |
|---|---|---|---|---|---|---|---|---|---|
|   | 5960 |   |   | 5965 |   |   | 5970 |   |   |
| Ala | Ala | Gly | Gly | Ala | Ala | Ala | Gly | Thr | Gly | Ala | Gly | Thr |
|   | 5975 |   |   | 5980 |   |   | 5985 |   |   |

Ala Ala Gly Gly Ala Ala Ala Gly Thr Gly Ala Gly Thr
  5975              5980              5985

Gly Cys Thr Ala Cys Cys Gly Ala Ala Cys Cys Thr Gly Cys
  5990              5995              6000

Ala Thr Cys Cys Thr Gly Thr Thr Cys Cys Thr Thr Thr Gly Thr
  6005              6010              6015

Ala Thr Thr Cys Ala Thr Cys Thr Ala Gly Thr Gly Thr Gly Ala
  6020              6025              6030

Ala Cys Cys Gly Thr Gly Cys Cys Thr Thr Thr Cys Ala Ala
  6035              6040              6045

Gly Cys Cys Cys Ala Ala Gly Gly Thr Cys Gly Cys Ala Gly
  6050              6055              6060

Thr Gly Gly Ala Ala Gly Cys Cys Thr Gly Thr Ala Ala Cys Gly
  6065              6070              6075

Cys Cys Ala Thr Gly Thr Thr Gly Ala Ala Ala Gly Ala Gly Ala
  6080              6085              6090

Ala Cys Thr Thr Thr Cys Cys Gly Ala Cys Thr Gly Thr Gly Gly
  6095              6100              6105

Cys Thr Thr Cys Thr Thr Ala Cys Thr Gly Thr Ala Thr Thr Ala
  6110              6115              6120

Thr Thr Cys Cys Ala Gly Ala Gly Thr Ala Cys Gly Ala Thr Gly
  6125              6130              6135

Cys Cys Thr Ala Thr Thr Gly Gly Ala Cys Ala Thr Gly Gly
  6140              6145              6150

Thr Thr Gly Ala Cys Gly Gly Ala Gly Cys Thr Thr Cys Ala Thr
  6155              6160              6165

Gly Cys Thr Gly Cys Thr Thr Ala Gly Ala Cys Ala Cys Thr Gly
  6170              6175              6180

Cys Cys Ala Gly Thr Thr Thr Thr Thr Gly Cys Cys Thr Gly
  6185              6190              6195

Cys Ala Ala Ala Gly Cys Thr Gly Cys Gly Cys Ala Gly Cys Thr
  6200              6205              6210

Thr Thr Cys Cys Ala Ala Ala Gly Ala Ala Ala Cys Ala Cys Thr
  6215              6220              6225

Cys Cys Thr Ala Thr Thr Thr Gly Gly Ala Ala Cys Cys Cys Ala
  6230              6235              6240

Cys Ala Ala Thr Ala Cys Gly Ala Thr Cys Gly Gly Cys Ala Gly
  6245              6250              6255

Thr Gly Cys Cys Thr Thr Cys Ala Gly Cys Gly Ala Thr Cys Cys
  6260              6265              6270

Ala Gly Ala Ala Cys Ala Cys Gly Cys Thr Cys Cys Ala Gly Ala
  6275              6280              6285

Ala Cys Gly Thr Cys Cys Thr Gly Gly Cys Ala Gly Cys Thr Gly
  6290              6295              6300

Cys Cys Ala Cys Ala Ala Ala Ala Gly Ala Ala Ala Thr Thr
  6305              6310              6315

Gly Cys Ala Ala Thr Gly Thr Cys Ala Cys Gly Cys Ala Ala Ala
  6320              6325              6330

Thr Gly Ala Gly Ala Gly Ala Ala Thr Thr Gly Cys Cys Cys Gly
  6335              6340              6345

Thr Ala Thr Thr Gly Gly Ala Thr Thr Cys Gly Gly Cys Gly Gly
  6350              6355              6360

-continued

Cys Cys Thr Thr Thr Ala Ala Thr Gly Thr Gly Gly Ala Ala Thr
    6365                6370                6375

Gly Cys Thr Thr Cys Ala Ala Gly Ala Ala Ala Thr Ala Thr Gly
    6380                6385                6390

Cys Gly Thr Gly Thr Ala Ala Thr Ala Ala Thr Gly Ala Ala Thr
    6395                6400                6405

Ala Thr Thr Gly Gly Gly Ala Ala Ala Cys Gly Thr Thr Thr Ala
    6410                6415                6420

Ala Ala Gly Ala Ala Ala Ala Cys Cys Cys Ala Thr Cys Ala
    6425                6430                6435

Gly Gly Cys Thr Thr Ala Cys Thr Gly Ala Ala Gly Ala Ala Ala
    6440                6445                6450

Ala Cys Gly Thr Gly Gly Thr Ala Ala Ala Thr Thr Ala Cys Ala
    6455                6460                6465

Thr Thr Ala Cys Cys Ala Ala Ala Thr Thr Ala Ala Ala Ala Gly
    6470                6475                6480

Gly Ala Cys Cys Ala Ala Ala Ala Gly Cys Thr Gly Cys Thr Gly
    6485                6490                6495

Cys Thr Cys Thr Thr Thr Thr Thr Gly Cys Gly Ala Ala Gly Ala
    6500                6505                6510

Cys Ala Cys Ala Thr Ala Ala Thr Thr Thr Gly Ala Ala Thr Ala
    6515                6520                6525

Thr Gly Thr Thr Gly Cys Ala Gly Gly Ala Cys Ala Thr Ala Cys
    6530                6535                6540

Cys Ala Ala Thr Gly Gly Ala Cys Ala Gly Gly Thr Thr Thr Gly
    6545                6550                6555

Thr Ala Ala Thr Gly Gly Ala Cys Thr Thr Ala Ala Ala Gly Ala
    6560                6565                6570

Gly Ala Gly Ala Cys Gly Thr Gly Ala Ala Ala Gly Thr Gly Ala
    6575                6580                6585

Cys Thr Cys Cys Ala Gly Gly Ala Ala Cys Ala Ala Ala Ala Cys
    6590                6595                6600

Ala Thr Ala Cys Thr Gly Ala Ala Gly Ala Ala Cys Gly Gly Cys
    6605                6610                6615

Cys Cys Ala Ala Gly Gly Thr Ala Cys Ala Gly Gly Thr Gly Ala
    6620                6625                6630

Thr Cys Cys Ala Gly Gly Cys Thr Gly Cys Cys Gly Ala Thr Cys
    6635                6640                6645

Cys Gly Cys Thr Ala Gly Cys Ala Ala Cys Ala Gly Cys Gly Thr
    6650                6655                6660

Ala Thr Cys Thr Gly Thr Gly Cys Gly Gly Ala Ala Thr Cys Cys
    6665                6670                6675

Ala Cys Cys Gly Ala Gly Ala Gly Cys Thr Gly Gly Thr Thr Ala
    6680                6685                6690

Gly Gly Ala Gly Ala Thr Thr Ala Ala Ala Thr Gly Cys Gly Gly
    6695                6700                6705

Thr Cys Cys Thr Gly Cys Thr Cys Cys Gly Ala Ala Cys Ala
    6710                6715                6720

Thr Thr Cys Ala Thr Ala Cys Ala Cys Thr Gly Thr Thr Thr Gly
    6725                6730                6735

Ala Thr Ala Thr Gly Thr Cys Gly Gly Cys Thr Gly Ala Ala Gly
    6740                6745                6750

Ala Cys Thr Thr Thr Gly Ala Cys Gly Cys Thr Ala Thr Thr Ala
6755 6760 6765

Thr Ala Gly Cys Cys Gly Ala Gly Cys Ala Cys Thr Thr Cys Cys
6770 6775 6780

Ala Gly Cys Cys Thr Gly Gly Gly Gly Ala Thr Thr Gly Thr Gly
6785 6790 6795

Thr Thr Cys Thr Gly Gly Ala Ala Ala Cys Thr Gly Ala Cys Ala
6800 6805 6810

Thr Cys Gly Cys Gly Thr Cys Gly Thr Thr Thr Gly Ala Thr Ala
6815 6820 6825

Ala Ala Ala Gly Thr Gly Ala Gly Gly Ala Cys Gly Ala Cys Gly
6830 6835 6840

Cys Cys Ala Thr Gly Gly Cys Thr Cys Thr Gly Ala Cys Cys Gly
6845 6850 6855

Cys Gly Thr Thr Ala Ala Thr Gly Ala Thr Thr Cys Thr Gly Gly
6860 6865 6870

Ala Ala Gly Ala Cys Thr Thr Ala Gly Gly Thr Gly Thr Gly Gly
6875 6880 6885

Ala Cys Gly Cys Ala Gly Ala Gly Cys Thr Gly Thr Thr Gly Ala
6890 6895 6900

Cys Gly Cys Thr Gly Ala Thr Thr Gly Ala Gly Gly Cys Gly Gly
6905 6910 6915

Cys Thr Thr Thr Cys Gly Gly Cys Gly Ala Ala Ala Thr Thr Thr
6920 6925 6930

Cys Ala Thr Cys Ala Ala Thr Ala Cys Ala Thr Thr Thr Gly Cys
6935 6940 6945

Cys Cys Ala Cys Thr Ala Ala Ala Ala Cys Thr Ala Ala Ala Thr
6950 6955 6960

Thr Thr Ala Ala Ala Thr Thr Cys Gly Gly Ala Gly Cys Cys Ala
6965 6970 6975

Thr Gly Ala Thr Gly Ala Ala Ala Thr Cys Thr Gly Gly Ala Ala
6980 6985 6990

Thr Gly Thr Thr Cys Cys Thr Cys Ala Cys Ala Cys Thr Gly Thr
6995 7000 7005

Thr Thr Gly Thr Gly Ala Ala Cys Ala Cys Ala Gly Thr Cys Ala
7010 7015 7020

Thr Thr Ala Ala Cys Ala Thr Thr Gly Thr Ala Ala Thr Cys Gly
7025 7030 7035

Cys Ala Ala Gly Cys Ala Gly Ala Gly Thr Gly Thr Thr Gly Ala
7040 7045 7050

Gly Ala Gly Ala Ala Cys Gly Gly Cys Thr Ala Ala Cys Cys Gly
7055 7060 7065

Gly Ala Thr Cys Ala Cys Cys Ala Thr Gly Thr Gly Cys Ala Gly
7070 7075 7080

Cys Ala Thr Thr Cys Ala Thr Thr Gly Gly Ala Gly Ala Thr Gly
7085 7090 7095

Ala Cys Ala Ala Thr Ala Thr Cys Gly Thr Gly Ala Ala Ala Gly
7100 7105 7110

Gly Ala Gly Thr Cys Ala Ala Ala Thr Cys Gly Gly Ala Cys Ala
7115 7120 7125

Ala Ala Thr Thr Ala Ala Thr Gly Gly Cys Ala Gly Ala Cys Ala
7130 7135 7140

Gly Gly Thr Gly Cys Gly Cys Cys Ala Cys Cys Thr Gly Gly Thr 7145 7150 7155

Thr Gly Ala Ala Thr Ala Thr Gly Gly Ala Ala Gly Thr Cys Ala
7160 7165 7170

Ala Gly Ala Thr Thr Ala Thr Ala Gly Ala Thr Gly Cys Thr Gly
7175 7180 7185

Thr Gly Gly Thr Gly Gly Gly Cys Gly Ala Gly Ala Ala Ala Gly
7190 7195 7200

Cys Gly Cys Cys Thr Thr Ala Thr Thr Thr Cys Thr Gly Thr Gly
7205 7210 7215

Gly Ala Gly Gly Gly Thr Thr Thr Ala Thr Thr Thr Thr Gly Thr
7220 7225 7230

Gly Thr Gly Ala Cys Thr Cys Cys Gly Thr Gly Ala Cys Cys Gly
7235 7240 7245

Gly Cys Ala Cys Ala Gly Cys Gly Thr Gly Cys Cys Gly Thr Gly
7250 7255 7260

Thr Gly Gly Cys Ala Gly Ala Cys Cys Cys Cys Cys Thr Ala Ala
7265 7270 7275

Ala Ala Ala Gly Gly Cys Thr Gly Thr Thr Thr Ala Ala Gly Cys
7280 7285 7290

Thr Thr Gly Gly Cys Ala Ala Ala Cys Cys Thr Cys Thr Gly Gly
7295 7300 7305

Cys Ala Gly Cys Ala Gly Ala Cys Gly Ala Thr Gly Ala Ala Cys
7310 7315 7320

Ala Thr Gly Ala Thr Gly Ala Thr Gly Ala Cys Ala Gly Gly Ala
7325 7330 7335

Gly Ala Ala Gly Gly Gly Cys Ala Thr Thr Gly Cys Ala Thr Gly
7340 7345 7350

Ala Ala Gly Ala Gly Thr Cys Ala Ala Cys Ala Cys Gly Cys Thr
7355 7360 7365

Gly Gly Ala Ala Cys Cys Gly Ala Gly Thr Gly Gly Gly Thr Ala
7370 7375 7380

Thr Thr Cys Thr Thr Thr Cys Ala Gly Ala Gly Cys Thr Gly Thr
7385 7390 7395

Gly Cys Ala Ala Gly Gly Cys Ala Gly Thr Ala Gly Ala Ala Thr
7400 7405 7410

Cys Ala Ala Gly Gly Thr Ala Thr Gly Ala Ala Ala Cys Cys Gly
7415 7420 7425

Thr Ala Gly Gly Ala Ala Cys Thr Thr Cys Cys Ala Thr Cys Ala
7430 7435 7440

Thr Ala Gly Thr Thr Ala Thr Gly Gly Cys Cys Ala Thr Gly Ala
7445 7450 7455

Cys Thr Ala Cys Thr Cys Thr Ala Gly Cys Thr Ala Gly Cys Ala
7460 7465 7470

Gly Thr Gly Thr Thr Ala Ala Ala Thr Cys Ala Thr Thr Cys Ala
7475 7480 7485

Gly Cys Thr Ala Cys Cys Thr Gly Ala Gly Ala Gly Gly Gly Gly
7490 7495 7500

Cys Cys Cys Cys Thr Ala Thr Ala Ala Cys Thr Cys Thr Cys Thr
7505 7510 7515

Ala Cys Gly Gly Cys Thr Ala Ala Cys Cys Thr Gly Ala Ala Thr
7520 7525 7530

Gly Gly Ala Cys Thr Ala Cys Gly Ala Cys Ala Thr Ala Gly Thr
7535 7540 7545

```
Cys Thr Ala Gly Thr Cys Cys Gly Cys Ala Gly Ala Thr
         7550              7555              7560

Gly Thr Thr Cys Cys Cys Gly Thr Thr Cys Ala Gly Cys Cys
         7565              7570              7575

Ala Ala Thr Gly Thr Ala Thr Cys Cys Gly Ala Thr Gly Cys Ala
         7580              7585              7590

Gly Cys Cys Ala Ala Thr Gly Cys Cys Cys Thr Ala Thr Cys Gly
         7595              7600              7605

Cys Ala Ala Cys Cys Cys Gly Thr Thr Cys Gly Cys Gly Gly Cys
         7610              7615              7620

Cys Cys Cys Gly Cys Gly Cys Ala Gly Gly Cys Cys Cys Thr Gly
         7625              7630              7635

Gly Thr Thr Cys Cys Cys Ala Gly Ala Ala Cys Cys Gly Ala
         7640              7645              7650

Cys Cys Cys Thr Thr Thr Cys Thr Gly Gly Cys Gly Ala Thr
         7655              7660              7665

Gly Cys Ala Gly Gly Thr Gly Cys Ala Gly Gly Ala Ala Thr Thr
         7670              7675              7680

Ala Ala Cys Cys Cys Gly Cys Thr Cys Gly Ala Thr Gly Gly Cys
         7685              7690              7695

Thr Ala Ala Cys Cys Thr Gly Ala Cys Gly Thr Thr Cys Ala Ala
         7700              7705              7710

Gly Cys Ala Ala Cys Gly Cys Cys Gly Gly Ala Cys Gly Cys
         7715              7720              7725

Gly Cys Cys Ala Cys Cys Thr Gly Ala Gly Gly Gly Gly Cys Cys
         7730              7735              7740

Ala Thr Cys Cys Gly Cys Thr Ala Ala Gly Ala Ala Ala Cys Cys
         7745              7750              7755

Gly Ala Ala Gly Ala Ala Gly Gly Ala Gly Gly Cys Cys Thr Cys
         7760              7765              7770

Gly Cys Ala Ala Ala Ala Ala Cys Ala Gly Ala Ala Ala Gly Gly
         7775              7780              7785

Gly Gly Gly Ala Gly Gly Cys Cys Ala Ala Gly Gly Ala Ala
         7790              7795              7800

Gly Ala Ala Gly Ala Ala Gly Ala Ala Gly Ala Ala Cys Cys Ala
         7805              7810              7815

Ala Gly Gly Gly Ala Ala Gly Ala Ala Gly Ala Ala Gly Gly Cys
         7820              7825              7830

Thr Ala Ala Gly Gly Cys Ala Gly Gly Gly Cys Cys Gly Cys Cys
         7835              7840              7845

Thr Ala Ala Thr Cys Cys Gly Ala Ala Gly Gly Cys Ala Cys Ala
         7850              7855              7860

Gly Ala Ala Thr Gly Gly Ala Ala Ala Cys Ala Ala Gly Ala Ala
         7865              7870              7875

Gly Ala Ala Gly Gly Cys Cys Ala Ala Cys Ala Ala Gly Ala Ala
         7880              7885              7890

Ala Cys Cys Ala Gly Gly Cys Ala Ala Gly Ala Gly Ala Cys Ala
         7895              7900              7905

Gly Cys Gly Cys Ala Thr Gly Gly Thr Cys Ala Thr Gly Ala Ala
         7910              7915              7920

Ala Thr Thr Gly Gly Ala Ala Gly Cys Thr Gly Ala Cys Ala Ala
         7925              7930              7935
```

Gly Gly Cys Gly Thr Thr Cys Cys Cys Ala Ala Thr Cys Ala Thr
7940 7945 7950

Gly Thr Thr Gly Gly Ala Ala Gly Gly Gly Ala Ala Gly Ala Thr
7955 7960 7965

Ala Ala Ala Cys Gly Gly Cys Thr Ala Cys Gly Cys Thr Thr Gly
7970 7975 7980

Thr Gly Thr Gly Gly Thr Cys Gly Gly Ala Gly Gly Gly Ala Ala
7985 7990 7995

Gly Thr Thr Ala Thr Thr Cys Ala Gly Gly Cys Cys Gly Ala Thr
8000 8005 8010

Gly Cys Ala Thr Gly Thr Gly Gly Ala Ala Gly Gly Cys Ala Ala
8015 8020 8025

Gly Ala Thr Ala Gly Ala Cys Ala Ala Cys Gly Ala Cys Gly Thr
8030 8035 8040

Thr Cys Thr Gly Gly Cys Cys Gly Cys Gly Cys Thr Thr Ala Ala
8045 8050 8055

Gly Ala Cys Gly Ala Ala Gly Ala Ala Ala Gly Cys Ala Thr Cys
8060 8065 8070

Cys Ala Ala Ala Thr Ala Cys Gly Ala Thr Cys Thr Thr Gly Ala
8075 8080 8085

Gly Thr Ala Thr Gly Cys Ala Gly Ala Thr Gly Thr Gly Cys Cys
8090 8095 8100

Ala Cys Ala Gly Ala Ala Cys Ala Thr Gly Cys Gly Gly Gly Cys
8105 8110 8115

Cys Gly Ala Thr Ala Cys Ala Thr Thr Cys Ala Ala Ala Thr Ala
8120 8125 8130

Cys Ala Cys Cys Cys Ala Thr Gly Ala Gly Ala Ala Ala Cys Cys
8135 8140 8145

Cys Cys Ala Ala Gly Gly Cys Thr Ala Thr Thr Ala Cys Ala Gly
8150 8155 8160

Cys Thr Gly Gly Cys Ala Thr Cys Ala Thr Gly Gly Ala Gly Cys
8165 8170 8175

Ala Gly Thr Cys Cys Ala Ala Thr Ala Thr Gly Ala Ala Ala Ala
8180 8185 8190

Thr Gly Gly Gly Cys Gly Thr Thr Thr Cys Ala Cys Gly Gly Thr
8195 8200 8205

Gly Cys Cys Gly Ala Ala Ala Gly Gly Ala Gly Thr Thr Gly Gly
8210 8215 8220

Gly Gly Cys Cys Ala Ala Gly Gly Gly Ala Gly Ala Cys Ala Gly
8225 8230 8235

Cys Gly Gly Ala Cys Gly Ala Cys Cys Cys Ala Thr Thr Cys Thr
8240 8245 8250

Gly Gly Ala Thr Ala Ala Cys Cys Ala Gly Gly Gly Ala Cys Gly
8255 8260 8265

Gly Gly Thr Gly Gly Thr Cys Gly Cys Thr Ala Thr Thr Gly Thr
8270 8275 8280

Gly Cys Thr Gly Gly Gly Ala Gly Gly Thr Gly Thr Gly Ala Ala
8285 8290 8295

Thr Gly Ala Ala Gly Gly Ala Thr Cys Thr Ala Gly Gly Ala Cys
8300 8305 8310

Ala Gly Cys Cys Cys Thr Thr Thr Cys Ala Gly Thr Cys Gly Thr
8315 8320 8325

Cys Ala Thr Gly Thr Gly Gly Ala Ala Cys Gly Ala Gly Ala Ala

```
    8330                8335                8340

Gly Gly  Gly Ala Gly Thr Thr  Ala Cys Cys Gly Thr  Gly Ala Ala
    8345                8350                8355

Gly Thr  Ala Thr Ala Cys Thr  Cys Cys Gly Gly Ala  Gly Ala Ala
    8360                8365                8370

Cys Thr  Gly Cys Gly Ala Gly  Cys Ala Ala Thr Gly  Gly Thr Cys
    8375                8380                8385

Ala Cys  Thr Ala Gly Thr Gly  Ala Cys Cys Ala Cys  Cys Ala Thr
    8390                8395                8400

Gly Thr  Gly Thr Cys Thr Gly  Cys Thr Cys Gly Cys  Cys Ala Ala
    8405                8410                8415

Thr Gly  Thr Gly Ala Cys Gly  Thr Thr Cys Cys Cys  Ala Thr Gly
    8420                8425                8430

Thr Gly  Cys Thr Cys Ala Ala  Cys Cys Ala Cys Cys  Ala Ala Thr
    8435                8440                8445

Thr Thr  Gly Cys Thr Ala Cys  Gly Ala Cys Ala Gly  Ala Ala Ala
    8450                8455                8460

Ala Cys  Cys Ala Gly Cys Ala  Gly Ala Gly Ala Cys  Thr Thr Thr
    8465                8470                8475

Gly Gly  Cys Cys Ala Thr Gly  Cys Thr Cys Ala Gly  Cys Gly Thr
    8480                8485                8490

Thr Ala  Ala Cys Gly Thr Thr  Gly Ala Cys Ala Ala  Cys Cys Cys
    8495                8500                8505

Gly Gly  Gly Cys Thr Ala Cys  Gly Ala Thr Gly Ala  Gly Cys Thr
    8510                8515                8520

Gly Cys  Thr Gly Gly Ala Ala  Gly Cys Ala Gly Cys  Thr Gly Thr
    8525                8530                8535

Thr Ala  Ala Gly Thr Gly Cys  Cys Cys Cys Gly Gly  Ala Ala Gly
    8540                8545                8550

Gly Ala  Ala Ala Ala Gly Gly  Ala Gly Ala Thr Cys  Cys Ala Cys
    8555                8560                8565

Cys Gly  Ala Gly Gly Ala Gly  Cys Thr Gly Thr Thr  Thr Ala Ala
    8570                8575                8580

Thr Gly  Ala Gly Thr Ala Thr  Ala Ala Gly Cys Thr  Ala Ala Cys
    8585                8590                8595

Gly Cys  Gly Cys Cys Cys Thr  Thr Ala Cys Ala Thr  Gly Gly Cys
    8600                8605                8610

Cys Ala  Gly Ala Thr Gly Cys  Ala Thr Cys Ala Gly  Ala Thr Gly
    8615                8620                8625

Thr Gly  Cys Ala Gly Thr Thr  Gly Gly Gly Ala Gly  Cys Thr Gly
    8630                8635                8640

Cys Cys  Ala Thr Ala Gly Thr  Cys Cys Ala Ala Thr  Ala Gly Cys
    8645                8650                8655

Ala Ala  Thr Cys Gly Ala Gly  Gly Cys Ala Gly Thr  Ala Ala Ala
    8660                8665                8670

Gly Ala  Gly Cys Gly Ala Cys  Gly Gly Gly Cys Ala  Cys Gly Ala
    8675                8680                8685

Cys Gly  Gly Thr Thr Ala Thr  Gly Thr Thr Ala Gly  Ala Cys Thr
    8690                8695                8700

Thr Cys  Ala Gly Ala Cys Thr  Thr Cys Cys Thr Cys  Gly Cys Ala
    8705                8710                8715

Gly Thr  Ala Thr Gly Gly Cys  Cys Thr Gly Gly Ala  Thr Thr Cys
    8720                8725                8730
```

```
Cys Thr Cys Cys Gly Gly Cys Ala Ala Cys Thr Thr Ala Ala Ala
    8735            8740                8745

Gly Gly Gly Cys Ala Gly Gly Ala Cys Cys Ala Thr Gly Cys Gly
    8750            8755                8760

Gly Thr Ala Thr Gly Ala Cys Ala Thr Gly Cys Ala Cys Gly Gly
    8765            8770                8775

Gly Ala Cys Cys Ala Thr Thr Ala Ala Gly Ala Gly Ala Thr
    8780            8785                8790

Ala Cys Cys Ala Cys Thr Ala Cys Ala Thr Cys Ala Ala Gly Thr
    8795            8800                8805

Gly Thr Cys Ala Cys Thr Cys Thr Ala Thr Ala Cys Ala Thr Cys
    8810            8815                8820

Thr Cys Gly Cys Cys Gly Thr Gly Thr Cys Ala Cys Ala Thr
    8825            8830                8835

Thr Gly Thr Gly Gly Ala Thr Gly Gly Gly Cys Ala Cys Gly Gly
    8840            8845                8850

Thr Thr Ala Thr Thr Thr Cys Cys Thr Gly Cys Thr Thr Gly Cys
    8855            8860                8865

Cys Ala Gly Gly Thr Gly Cys Cys Cys Gly Gly Cys Ala Gly Gly
    8870            8875                8880

Gly Gly Ala Cys Thr Cys Cys Ala Thr Cys Ala Cys Cys Ala Thr
    8885            8890                8895

Gly Gly Ala Ala Thr Thr Thr Ala Ala Gly Ala Ala Ala Gly Ala
    8900            8905                8910

Thr Thr Cys Cys Gly Thr Cys Ala Gly Ala Cys Ala Cys Thr Cys
    8915            8920                8925

Cys Thr Gly Cys Thr Cys Gly Gly Thr Gly Cys Cys Gly Thr Ala
    8930            8935                8940

Thr Gly Ala Ala Gly Thr Gly Ala Ala Ala Thr Thr Thr Ala Ala
    8945            8950                8955

Thr Cys Cys Thr Gly Thr Ala Gly Gly Cys Ala Gly Ala Gly Ala
    8960            8965                8970

Ala Cys Thr Cys Thr Ala Thr Ala Cys Thr Cys Ala Thr Cys Cys
    8975            8980                8985

Cys Cys Cys Ala Gly Ala Ala Cys Ala Cys Gly Gly Ala Gly Thr
    8990            8995                9000

Ala Gly Ala Gly Cys Ala Ala Gly Cys Gly Thr Gly Cys Cys Ala
    9005            9010                9015

Ala Gly Thr Cys Thr Ala Cys Gly Cys Ala Cys Ala Thr Gly Ala
    9020            9025                9030

Thr Gly Cys Ala Cys Ala Gly Ala Ala Cys Ala Gly Ala Gly Gly
    9035            9040                9045

Ala Gly Cys Thr Thr Ala Thr Gly Thr Cys Gly Ala Gly Ala Thr
    9050            9055                9060

Gly Cys Ala Cys Cys Thr Cys Cys Gly Gly Gly Cys Thr Cys
    9065            9070                9075

Ala Gly Ala Ala Gly Thr Gly Gly Ala Cys Ala Gly Cys Ala Gly
    9080            9085                9090

Thr Thr Thr Gly Gly Thr Thr Cys Cys Thr Thr Gly Ala Gly
    9095            9100                9105

Cys Gly Gly Cys Ala Gly Thr Thr Cys Ala Gly Thr Cys Ala Cys
    9110            9115                9120
```

```
Cys Gly Thr Gly Ala Cys Ala Cys Cys Thr Cys Cys Thr Gly Ala
    9125            9130               9135

Thr Gly Gly Gly Ala Cys Thr Ala Gly Cys Gly Cys Cys Cys Thr
    9140            9145               9150

Gly Gly Thr Gly Gly Ala Ala Thr Gly Thr Gly Ala Gly Thr Gly
    9155            9160               9165

Thr Gly Gly Cys Gly Gly Cys Ala Cys Ala Ala Ala Gly Ala Thr
    9170            9175               9180

Cys Thr Cys Cys Gly Ala Gly Ala Cys Cys Ala Thr Cys Ala Ala
    9185            9190               9195

Cys Ala Ala Gly Ala Cys Ala Ala Ala Cys Ala Gly Thr Thr
    9200            9205               9210

Cys Ala Gly Cys Cys Ala Gly Thr Gly Cys Ala Cys Ala Ala Ala
    9215            9220               9225

Gly Ala Ala Gly Gly Ala Gly Cys Ala Gly Thr Gly Cys Ala Gly
    9230            9235               9240

Ala Gly Cys Ala Thr Ala Thr Cys Gly Gly Cys Thr Gly Cys Ala
    9245            9250               9255

Gly Ala Ala Cys Gly Ala Thr Ala Ala Gly Thr Gly Gly Gly Thr
    9260            9265               9270

Gly Thr Ala Thr Ala Ala Thr Cys Thr Gly Ala Cys Ala Ala
    9275            9280               9285

Ala Cys Thr Gly Cys Cys Cys Ala Ala Gly Cys Ala Gly Cys
    9290            9295               9300

Gly Gly Gly Ala Gly Cys Cys Ala Cys Cys Thr Thr Ala Ala Ala
    9305            9310               9315

Ala Gly Gly Ala Ala Ala Cys Thr Gly Cys Ala Thr Gly Thr
    9320            9325               9330

Cys Cys Cys Ala Thr Thr Cys Thr Thr Gly Cys Thr Gly Gly Cys
    9335            9340               9345

Ala Gly Ala Cys Gly Gly Cys Ala Ala Ala Thr Gly Cys Ala Cys
    9350            9355               9360

Cys Gly Thr Gly Cys Cys Thr Cys Thr Ala Gly Cys Ala Cys Cys
    9365            9370               9375

Ala Gly Ala Ala Cys Cys Thr Ala Thr Gly Ala Thr Ala Ala Cys
    9380            9385               9390

Cys Thr Thr Cys Gly Gly Thr Thr Thr Cys Ala Gly Ala Thr Cys
    9395            9400               9405

Ala Gly Thr Gly Thr Cys Ala Cys Thr Gly Ala Ala Ala Cys Thr
    9410            9415               9420

Gly Cys Ala Cys Cys Thr Ala Ala Gly Ala Ala Thr Cys Cys
    9425            9430               9435

Cys Ala Cys Ala Thr Ala Thr Cys Thr Ala Ala Thr Cys Ala Cys
    9440            9445               9450

Cys Cys Gly Cys Cys Ala Ala Cys Thr Thr Gly Cys Thr Gly Ala
    9455            9460               9465

Thr Gly Ala Gly Cys Cys Thr Cys Ala Cys Thr Ala Cys Ala Cys
    9470            9475               9480

Gly Cys Ala Cys Gly Ala Gly Cys Thr Cys Ala Thr Ala Thr Cys
    9485            9490               9495

Thr Gly Ala Ala Cys Cys Ala Gly Cys Thr Gly Thr Thr Ala Gly
    9500            9505               9510

Gly Ala Ala Thr Thr Thr Thr Ala Cys Cys Gly Thr Cys Ala Cys
```

-continued

```
    9515                9520                9525

Cys Gly  Ala Ala Ala Ala Ala  Gly Gly Gly Thr Gly  Gly Gly Ala
    9530                9535                9540

Gly Thr  Thr Thr Gly Thr Ala  Thr Gly Gly Gly Gly  Ala Ala Ala
    9545                9550                9555

Cys Cys  Ala Cys Cys Cys Gly  Cys Cys Gly Ala Ala  Ala Ala Gly
    9560                9565                9570

Gly Thr  Thr Thr Thr Gly Gly  Gly Cys Ala Cys Ala  Gly Gly Ala
    9575                9580                9585

Ala Ala  Cys Ala Gly Cys Ala  Cys Cys Cys Gly Gly  Ala Ala Ala
    9590                9595                9600

Thr Cys  Cys Ala Cys Ala Thr  Gly Gly Gly Cys Thr  Ala Cys Cys
    9605                9610                9615

Gly Cys  Ala Cys Gly Ala Gly  Gly Thr Gly Ala Thr  Ala Ala Cys
    9620                9625                9630

Thr Cys  Ala Thr Thr Ala Thr  Thr Ala Cys Cys Ala  Cys Ala Gly
    9635                9640                9645

Ala Thr  Ala Cys Cys Cys Thr  Ala Thr Gly Thr Cys  Cys Ala Cys
    9650                9655                9660

Cys Ala  Thr Cys Cys Thr Gly  Gly Gly Thr Thr Thr  Gly Thr Cys
    9665                9670                9675

Ala Ala  Thr Thr Thr Gly Thr  Gly Cys Cys Gly Cys  Cys Ala Thr
    9680                9685                9690

Thr Gly  Cys Ala Ala Cys Cys  Gly Thr Thr Thr Cys  Cys Gly Thr
    9695                9700                9705

Thr Gly  Cys Ala Gly Cys Gly  Thr Cys Thr Ala Cys  Cys Thr Gly
    9710                9715                9720

Gly Cys  Thr Gly Thr Thr Thr  Thr Gly Cys Ala Gly  Ala Thr Cys
    9725                9730                9735

Thr Ala  Gly Ala Gly Thr Thr  Gly Cys Gly Thr Gly  Cys Cys Thr
    9740                9745                9750

Ala Ala  Cys Thr Cys Cys Thr  Thr Ala Cys Cys Gly  Gly Cys Thr
    9755                9760                9765

Ala Ala  Cys Ala Cys Cys Thr  Ala Ala Cys Gly Cys  Thr Ala Gly
    9770                9775                9780

Gly Ala  Thr Ala Cys Cys Ala  Thr Thr Thr Thr Gly  Thr Cys Thr
    9785                9790                9795

Gly Gly  Cys Thr Gly Thr Gly  Cys Thr Thr Thr Gly  Cys Thr Gly
    9800                9805                9810

Cys Gly  Cys Cys Cys Gly Cys  Ala Cys Thr Gly Cys  Cys Cys Gly
    9815                9820                9825

Gly Gly  Cys Cys Gly Ala Gly  Ala Cys Cys Ala Cys  Cys Thr Gly
    9830                9835                9840

Gly Gly  Ala Gly Thr Cys Cys  Thr Thr Gly Gly Ala  Thr Cys Ala
    9845                9850                9855

Cys Cys  Thr Ala Thr Gly Gly  Ala Ala Cys Ala Ala  Thr Ala Ala
    9860                9865                9870

Cys Cys  Ala Ala Cys Ala Gly  Ala Thr Gly Thr Thr  Cys Thr Gly
    9875                9880                9885

Gly Ala  Thr Thr Cys Ala Ala  Thr Thr Gly Cys Thr  Gly Ala Thr
    9890                9895                9900

Cys Cys  Cys Thr Cys Thr Gly  Gly Cys Cys Gly Cys  Cys Thr Thr
    9905                9910                9915
```

-continued

```
Gly Ala  Thr Cys Gly Thr Ala  Gly Thr Gly Ala Cys  Thr Cys Gly
    9920             9925                9930

Cys Cys  Thr Gly Cys Thr Cys  Ala Gly Gly Thr Gly  Cys Gly Thr
    9935             9940                9945

Gly Thr  Gly Cys Thr Gly Thr  Gly Thr Cys Gly Thr  Gly Cys Cys
    9950             9955                9960

Thr Thr  Thr Thr Thr Thr Ala  Gly Thr Cys Ala Thr  Gly Gly Cys
    9965             9970                9975

Cys Gly  Gly Cys Gly Cys Cys  Gly Cys Ala Gly Cys  Gly Cys
    9980             9985                9990

Cys Gly  Gly Cys Gly Cys Cys  Thr Ala Cys Gly Ala  Gly Cys Ala
    9995             10000               10005

Cys Gly  Cys Gly Ala Cys Cys  Ala Cys Gly Ala Thr  Gly Cys Cys
    10010            10015               10020

Gly Ala  Gly Cys Cys Ala Ala  Gly Cys Gly Gly Gly  Ala Ala Thr
    10025            10030               10035

Cys Thr  Cys Gly Thr Ala Thr  Ala Ala Cys Ala Cys  Thr Ala Thr
    10040            10045               10050

Ala Gly  Thr Cys Ala Ala Cys  Ala Gly Ala Gly Cys  Ala Gly Gly
    10055            10060               10065

Cys Thr  Ala Cys Gly Cys Ala  Cys Cys Ala Cys Thr  Cys Cys Cys
    10070            10075               10080

Thr Ala  Thr Cys Ala Gly Cys  Ala Thr Ala Ala Cys  Ala Cys Cys
    10085            10090               10095

Ala Ala  Cys Ala Ala Ala Gly  Ala Thr Cys Ala Ala  Gly Cys Thr
    10100            10105               10110

Gly Ala  Thr Ala Cys Cys Thr  Ala Cys Ala Gly Thr  Gly Ala Ala
    10115            10120               10125

Cys Thr  Thr Gly Gly Ala Gly  Thr Ala Cys Gly Thr  Cys Ala Cys
    10130            10135               10140

Cys Thr  Gly Cys Cys Ala Cys  Thr Ala Cys Ala Ala  Ala Ala Cys
    10145            10150               10155

Ala Gly  Gly Ala Ala Thr Gly  Gly Ala Thr Thr Cys  Ala Cys Cys
    10160            10165               10170

Ala Gly  Cys Cys Ala Thr Cys  Ala Ala Ala Thr Gly  Cys Thr Gly
    10175            10180               10185

Cys Gly  Gly Ala Thr Cys Thr  Cys Ala Gly Gly Ala  Ala Thr Gly
    10190            10195               10200

Cys Ala  Cys Thr Cys Cys Ala  Ala Cys Thr Thr Ala  Cys Ala Gly
    10205            10210               10215

Gly Cys  Cys Thr Gly Ala Thr  Gly Ala Ala Cys Ala  Gly Thr Gly
    10220            10225               10230

Cys Ala  Ala Ala Gly Thr Cys  Thr Thr Cys Ala Cys  Ala Gly Gly
    10235            10240               10245

Gly Gly  Thr Thr Thr Ala Cys  Cys Cys Gly Thr Thr  Cys Ala Thr
    10250            10255               10260

Gly Thr  Gly Gly Gly Gly Thr  Gly Gly Thr Gly Cys  Ala Thr Ala
    10265            10270               10275

Thr Thr  Gly Cys Thr Thr Thr  Thr Gly Cys Gly Ala  Cys Ala Cys
    10280            10285               10290

Thr Gly  Ala Gly Ala Ala Cys  Ala Cys Cys Cys Ala  Ala Gly Thr
    10295            10300               10305
```

```
Cys Ala  Gly Cys Ala Ala Gly  Gly Cys Cys Thr Ala  Cys Gly Thr
    10310                10315                10320

Ala Ala  Thr Gly Ala Ala Ala  Thr Cys Thr Gly Ala  Cys Gly Ala
    10325                10330                10335

Cys Thr  Gly Cys Cys Thr Thr  Gly Cys Gly Gly Ala  Thr Cys Ala
    10340                10345                10350

Thr Gly  Cys Thr Gly Ala Ala  Gly Cys Ala Thr Ala  Thr Ala Ala
    10355                10360                10365

Ala Gly  Cys Gly Cys Ala Cys  Ala Cys Ala Gly Cys  Cys Thr Cys
    10370                10375                10380

Ala Gly  Thr Gly Cys Ala Gly  Gly Cys Gly Thr Thr  Cys Cys Thr
    10385                10390                10395

Cys Ala  Ala Cys Ala Thr Cys  Ala Cys Ala Gly Thr  Gly Gly Gly
    10400                10405                10410

Ala Gly  Ala Ala Cys Ala Cys  Thr Cys Thr Ala Thr  Thr Gly Thr
    10415                10420                10425

Gly Ala  Cys Thr Ala Cys Cys  Gly Thr Gly Thr Ala  Thr Gly Thr
    10430                10435                10440

Gly Ala  Ala Thr Gly Gly Ala  Gly Ala Ala Ala Cys  Thr Cys Cys
    10445                10450                10455

Thr Gly  Thr Gly Ala Ala Thr  Thr Thr Cys Ala Ala  Thr Gly Gly
    10460                10465                10470

Gly Gly  Thr Cys Ala Ala Ala  Ala Thr Ala Ala Cys  Thr Gly Cys
    10475                10480                10485

Ala Gly  Gly Thr Cys Cys Gly  Cys Thr Thr Thr Cys  Cys Ala Cys
    10490                10495                10500

Ala Gly  Cys Thr Thr Gly Gly  Ala Cys Ala Cys Cys  Cys Thr Thr
    10505                10510                10515

Thr Gly  Ala Thr Cys Gly Cys  Ala Ala Ala Ala Thr  Cys Gly Thr
    10520                10525                10530

Gly Cys  Ala Gly Thr Ala Thr  Gly Cys Cys Gly Gly  Gly Gly Ala
    10535                10540                10545

Gly Ala  Thr Cys Thr Ala Thr  Ala Ala Thr Thr Ala  Thr Gly Ala
    10550                10555                10560

Thr Thr  Thr Thr Cys Cys Thr  Gly Ala Gly Thr Ala  Thr Gly Gly
    10565                10570                10575

Gly Gly  Cys Ala Gly Gly Ala  Cys Ala Ala Cys Cys  Ala Gly Gly
    10580                10585                10590

Ala Gly  Cys Ala Thr Thr Thr  Gly Gly Ala Gly Ala  Thr Ala Thr
    10595                10600                10605

Ala Cys  Ala Ala Thr Cys Cys  Ala Gly Ala Ala Cys  Ala Gly Thr
    10610                10615                10620

Cys Thr  Cys Ala Ala Gly Cys  Thr Cys Thr Gly Ala  Thr Cys Thr
    10625                10630                10635

Gly Thr  Ala Thr Gly Cys Cys  Ala Ala Thr Ala Cys  Cys Ala Ala
    10640                10645                10650

Cys Cys  Thr Ala Gly Thr Gly  Cys Thr Gly Cys Ala  Gly Ala Gly
    10655                10660                10665

Ala Cys  Cys Cys Ala Ala Ala  Gly Cys Ala Gly Gly  Ala Gly Cys
    10670                10675                10680

Gly Ala  Thr Cys Cys Ala Cys  Gly Thr Gly Cys Cys  Ala Thr Ala
    10685                10690                10695

Cys Ala  Cys Thr Cys Ala Gly  Gly Cys Ala Cys Cys  Thr Thr Cys
```

|   |   |   |   |   |   |   |   |   |   |
|---|---|---|---|---|---|---|---|---|---|
| 10700 | | | | | 10705 | | | 10710 | |
| Gly | Gly | Gly | Thr | Thr | Thr | Thr | Gly | Ala | Gly | Cys | Ala | Ala | Thr | Gly |

Gly Gly Gly Thr Thr Thr Thr Gly Ala Gly Cys Ala Ala Thr Gly
    10715               10720               10725

Gly Ala Ala Gly Ala Ala Ala Gly Ala Thr Ala Ala Ala Gly Cys
    10730               10735               10740

Thr Cys Cys Ala Thr Cys Ala Thr Thr Gly Ala Ala Ala Thr Thr
    10745               10750               10755

Thr Ala Cys Cys Gly Cys Cys Cys Thr Thr Cys Gly Gly
    10760               10765               10770

Ala Thr Gly Cys Gly Ala Ala Ala Thr Ala Thr Ala Thr Ala Cys
    10775               10780               10785

Ala Ala Ala Cys Cys Cys Ala Thr Thr Cys Gly Cys Gly Cys
    10790               10795               10800

Cys Gly Ala Ala Ala Ala Cys Thr Gly Thr Gly Cys Thr Gly Thr
    10805               10810               10815

Ala Gly Gly Gly Thr Cys Ala Thr Thr Cys Cys Ala Thr Thr
    10820               10825               10830

Ala Gly Cys Cys Thr Thr Thr Gly Ala Cys Ala Thr Cys Cys
    10835               10840               10845

Cys Gly Ala Cys Gly Cys Cys Thr Thr Gly Thr Thr Cys Ala Cys
    10850               10855               10860

Cys Ala Gly Gly Gly Thr Gly Thr Cys Ala Gly Ala Ala Ala Cys
    10865               10870               10875

Ala Cys Cys Gly Ala Cys Ala Cys Thr Thr Thr Cys Ala Gly Cys
    10880               10885               10890

Gly Gly Cys Cys Gly Ala Gly Thr Gly Cys Ala Cys Thr Cys Thr
    10895               10900               10905

Thr Ala Ala Cys Gly Ala Gly Thr Gly Cys Gly Thr Gly Thr Ala
    10910               10915               10920

Thr Thr Cys Thr Thr Cys Cys Gly Ala Cys Thr Thr Gly Gly
    10925               10930               10935

Thr Gly Gly Gly Ala Thr Cys Gly Cys Cys Ala Cys Gly Gly Thr
    10940               10945               10950

Cys Ala Ala Gly Thr Ala Cys Thr Cys Gly Gly Cys Cys Ala Gly
    10955               10960               10965

Cys Ala Ala Gly Thr Cys Ala Gly Gly Cys Ala Ala Gly Thr Gly
    10970               10975               10980

Cys Gly Cys Ala Gly Thr Cys Cys Ala Thr Gly Thr Gly Cys Cys
    10985               10990               10995

Ala Thr Cys Ala Gly Gly Gly Ala Cys Thr Gly Cys Thr Ala Cys
    11000               11005               11010

Cys Cys Thr Ala Ala Ala Ala Gly Ala Ala Gly Cys Ala Gly Cys
    11015               11020               11025

Ala Gly Thr Cys Gly Ala Gly Cys Thr Ala Ala Cys Cys Gly Ala
    11030               11035               11040

Gly Cys Ala Ala Gly Gly Gly Thr Cys Gly Gly Cys Gly Ala Cys
    11045               11050               11055

Thr Ala Thr Cys Cys Ala Thr Thr Cys Thr Cys Gly Ala Cys
    11060               11065               11070

Cys Gly Cys Ala Ala Ala Thr Ala Thr Cys Cys Ala Cys Cys Cys
    11075               11080               11085

Gly Gly Ala Gly Thr Thr Cys Ala Gly Gly Cys Thr Cys Cys Ala
    11090               11095               11100

```
Ala Ala  Thr Ala Thr Gly Cys  Ala Cys Ala Thr Cys  Ala Thr Ala
    11105            11110                11115

Thr Gly  Thr Thr Ala Cys Gly  Thr Gly Cys Ala Ala  Ala Gly Gly
    11120            11125                11130

Thr Gly  Ala Thr Thr Gly Thr  Cys Ala Cys Cys Cys  Cys Cys Cys
    11135            11140                11145

Gly Ala  Ala Ala Gly Ala Cys  Cys Ala Thr Ala Thr  Thr Gly Thr
    11150            11155                11160

Gly Ala  Cys Ala Cys Ala Cys  Cys Cys Thr Cys Ala  Gly Thr Ala
    11165            11170                11175

Thr Cys  Ala Cys Gly Cys Cys  Cys Ala Ala Ala Cys  Ala Thr Thr
    11180            11185                11190

Thr Ala  Cys Ala Gly Cys Cys  Gly Cys Gly Gly Thr  Gly Thr Cys
    11195            11200                11205

Ala Ala  Ala Ala Ala Cys Cys  Gly Cys Gly Thr Gly  Gly Ala Cys
    11210            11215                11220

Gly Thr  Gly Gly Thr Thr Ala  Ala Cys Ala Thr Cys  Cys Cys Thr
    11225            11230                11235

Gly Cys  Thr Gly Gly Gly Ala  Gly Gly Ala Thr Cys  Ala Gly Cys
    11240            11245                11250

Cys Gly  Thr Ala Ala Thr Thr  Ala Thr Thr Ala Thr  Ala Ala Thr
    11255            11260                11265

Thr Gly  Gly Cys Thr Thr Gly  Gly Thr Gly Cys Thr  Gly Gly Cys
    11270            11275                11280

Thr Ala  Cys Thr Ala Thr Thr  Gly Thr Gly Gly Cys  Cys Ala Thr
    11285            11290                11295

Gly Thr  Ala Cys Gly Thr Gly  Cys Thr Gly Ala Cys  Cys Ala Ala
    11300            11305                11310

Cys Cys  Ala Gly Ala Ala Ala  Cys Ala Thr Ala Ala  Thr Thr Gly
    11315            11320                11325

Ala Ala  Thr Ala Cys Ala Gly  Cys Ala Gly Cys Ala  Ala Thr Thr
    11330            11335                11340

Gly Gly  Cys Ala Ala Gly Cys  Thr Gly Cys Thr Thr  Ala Cys Ala
    11345            11350                11355

Thr Ala  Gly Ala Ala Cys Thr  Cys Gly Cys Gly Gly  Cys Gly Ala
    11360            11365                11370

Thr Thr  Gly Gly Cys Ala Thr  Gly Cys Cys Gly Cys  Cys Thr Thr
    11375            11380                11385

Ala Ala  Ala Ala Thr Thr Thr  Thr Thr Ala Thr Thr  Thr Thr Ala
    11390            11395                11400

Thr Thr  Thr Thr Thr Cys Thr  Thr Thr Thr Cys Thr  Thr Thr Thr
    11405            11410                11415

Cys Cys  Gly Ala Ala Thr Cys  Gly Gly Ala Thr Thr  Thr Thr Gly
    11420            11425                11430

Thr Thr  Thr Thr Thr Ala Ala  Thr Ala Thr Thr Thr  Cys
    11435            11440                11445

<210> SEQ ID NO 21
<211> LENGTH: 11446
<212> TYPE: DNA
<213> ORGANISM: Venezuelan equine encephalitis virus
<220> FEATURE:
<221> NAME/KEY: misc_feature
<223> OTHER INFORMATION: TC-38 sequence
```

<400> SEQUENCE: 21

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccaccccct tttatgttta    600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggcc cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaatgttta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaggcagacg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatgcgtg ccaggatcag     2220
gcaagtctgg catcattaaa agcgcagtca ccaaaaaaga tctagtggtg agcgccaaga    2280
aagaaaactg tgcagaaatt ataagggacg tcaagaaat gaaagggctg gacgtcaatg      2340
```

```
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg cttagtgcc ggtgctgaag accgctggca   3120
tagacatgac cactgaacaa tggaaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca gttttcccg ggtatgcaaa ccgaaatcct   3900
cacttgaaga gacggaagtt ctgttttat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg ccaccgaagg   4080
gagtgattat aaatgctgct aacagcaaag acaacctgg cggagggggtg tgcggagcgc   4140 tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaacttc tcatatttgg aagggaccaa gtttcaccag gcggccaagg   4680
```

```
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccaccccgc     5520 caggcgtgaa tagggtgatc actagagagg agctcgaggc gcttacccc tcacgcactc     5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa agaaattgc aatgtcacgc aaatgagaga attgcccgta ttggattcgg     6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
```

```
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg     7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgttcccg ttccagccaa tgtatccgat gcagccaatg ccctatcgca acccgttcgc    7620
ggccccgcgc aggccctggt tccccagaac cgacccttt ctggcgatgc aggtgcagga     7680
attaacccgc tcgatggcta acctgacgtt caagcaacgc cgggacgcgc cacctgaggg    7740
gccatccgct aagaaaccga agaaggaggc ctcgcaaaaa cagaaagggg gaggccaagg    7800
gaagaagaag aagaaccaag ggaagaagaa ggctaagaca gggccgccta atccgaaggc    7860
acagaatgga aacaagaaga agaccaacaa gaaaccaggc aagagacagc gcatggtcat    7920
gaaattggaa tctgacaaga cgttcccaat catgttggaa gggaagataa acggctacgc    7980
ttgtgtggtc ggagggaagt tattcaggcc gatgcatgtg gaaggcaaga tagacaacga    8040
cgttctggcc gcgcttaaga cgaagaaagc atccaaatac gatcttgagt atgcagatgt    8100
gccacagaac atgcgggccg atacattcaa atacacccat gagaaacccc aaggctatta    8160
cagctggcat catggagcag tccaatatga aaatgggcgt tcacggtgc cgaaaggagt     8220 tggggccaag ggagacagcg gacgacccat tctggataac cagggacggg tggtcgctat    8280
tgtgctggga ggtgtgaatg aaggatctag gacagcccct tcagtcgtca tgtggaacga    8340
gaagggagtt accgtgaagt atactccgga gaactgcgag caatggtcac tagtgaccac    8400
catgtgtctg ctcgccaatg tgacgttccc atgtgctcaa ccaccaattt gctacgacag    8460
aaaaccagca gagactttgg ccatgctcag cgttaacgtt gacaacccgg gctacgatga    8520
gctgctggaa gcagctgtta agtgccccgg aaggaaaagg agatccaccg aggagctgtt    8580
taatgagtat aagctaacgc gcccttacat ggccagatgc atcagatgtg cagttgggag    8640
ctgccatagt ccaatagcaa tcgaggcagt aaagagcgac gggcacgacg ttatgttag    8700 acttcagact cctcgcagt atggcctgga ttcctccggc aacttaaagg gcaggaccat     8760
gcggtatgac atgcacggga ccattaaaga gataccacta catcaagtgt cactctatac    8820
atctcgcccg tgtcacattg tggatgggca cggttatttc ctgcttgcca ggtgcccggc    8880
aggggactcc atcaccatgg aatttaagaa agattccgtc agacactcct gctcggtgcc    8940
gtatgaagtg aaatttaatc ctgtaggcag agaactctat actcatcccc agaacacgg     9000 agtagagcaa gcgtgccaag tctacgcaca tgatgcacag aacagaggag cttatgtcga    9060
gatgcacctc ccgggctcag aagtggacag cagtttggtt tccttgagcg gcagttcagt    9120
caccgtgaca cctcctgatg ggactagcgc cctggtggaa tgtgagtgtg gcggcacaaa    9180
gatctccgag accatcaaca gacaaaaca gttcagccag tgcacaaaga aggagcagtg    9240
cagagcatat cggctgcaga acgataagtg ggtgtataat tctgacaaac tgcccaaagc    9300
agcgggagcc accttaaaag gaaaactgca tgtcccattc ttgctggcag acggcaaatg    9360
caccgtgcct ctagcaccag aacctatgat aaccttcggt ttcagatcag tgtcactgaa    9420
```

| | |
|---|---|
| actgcaccct aagaatccca catatctaat cacccgccaa cttgctgatg agcctcacta | 9480 |
| cacgcacgag ctcatatctg aaccagctgt taggaatttt accgtcaccg aaaaagggtg | 9540 |
| ggagtttgta tggggaaacc acccgccgaa aaggttttgg gcacaggaaa cagcacccgg | 9600 |
| aaatccacat gggctaccgc acgaggtgat aactcattat taccacagat accctatgtc | 9660 |
| caccatcctg ggtttgtcaa tttgtgccgc cattgcaacc gtttccgttg cagcgtctac | 9720 |
| ctggctgttt tgcagatcta gagttgcgtg cctaactcct taccggctaa cacctaacgc | 9780 |
| taggatacca tttttgtctgg ctgtgctttg ctgcgcccgc actgcccggg ccgagaccac | 9840 |
| ctgggagtcc ttggatcacc tatggaacaa taaccaacag atgttctgga ttcaattgct | 9900 |
| gatccctctg gccgccttga tcgtagtgac tcgcctgctc aggtgcgtgt gctgtgtcgt | 9960 |
| gcctttttta gtcatggccg cgccgcagg cgccggcgcc tacgagcacg cgaccacgat | 10020 |
| gccgagccaa gcgggaatct cgtataacac tatagtcaac agagcaggct acgcaccact | 10080 |
| ccctatcagc ataacaccaa caaagatcaa gctgatacct acagtgaact tggagtacgt | 10140 |
| cacctgccac tacaaaacag gaatggattc accagccatc aaatgctgcg gatctcagga | 10200 |
| atgcactcca acttacaggc ctgatgaaca gtgcaaagtc ttcacagggg tttacccgtt | 10260 |
| catgtggggt ggtgcatatt gcttttgcga cactgagaac acccaagtca gcaaggccta | 10320 |
| cgtaatgaaa tctgacgact gccttgcgga tcatgctgaa gcatataaag cgcacacagc | 10380 |
| ctcagtgcag gcgttcctca acatcacagt gggagaacac tctattgtga ctaccgtgta | 10440 |
| tgtgaatgga gaaactcctg tgaatttcaa tgggggtcaaa ataactgcag gtccgctttc | 10500 |
| cacagcttgg acacccttg atcgcaaaat cgtgcagtat gccggggaga tctataatta | 10560 |
| tgattttcct gagtatgggg caggacaacc aggagcattt ggagatatac aatccagaac | 10620 |
| agtctcaagc tctgatctgt atgccaatac caacctagtg ctgcagagac ccaaagcagg | 10680 |
| agcgatccac gtgccataca ctcaggcacc ttcgggtttt gagcaatgga gaaagataa | 10740 |
| agctccatca ttgaaattta ccgccccttt cggatgcgaa atatatacaa accccattcg | 10800 |
| cgccgaaaac tgtgctgtag ggtcaattcc attagccttt gacattcccg acgccttgtt | 10860 |
| caccagggtg tcagaaacac cgacactttc agcggccgag tgcactctta cgagtgcgt | 10920 |
| gtattcttcc gactttggtg gatcgccac ggtcaagtac tcggccagca agtcaggcaa | 10980 |
| gtgcgcagtc catgtgccat cagggactgc taccctaaaa gaagcagcag tcgagctaac | 11040 |
| cgagcaaggg tcggcgacta ccatttctc gaccgcaaat atccaccgg agttcaggct | 11100 |
| ccaaatatgc acatcatatg ttacgtgcaa aggtgattgt caccccccga agaccatat | 11160 |
| tgtgacacac cctcagtatc acgcccaaac atttacagcc gcggtgtcaa aaaccgcgtg | 11220 |
| gacgtggtta acatccctgc tgggaggatc agccgtaatt attataattg cttggtgct | 11280 |
| ggctactatt gtggccatgt acgtgctgac caaccagaaa cataattgaa tacagcagca | 11340 |
| attggcaagc tgcttacata gaactcgcgg cgattggcat gccgccttaa aatttttatt | 11400 |
| ttatttttct tttcttttcc gaatcggatt tgttttttaa tatttc | 11446 |

<210> SEQ ID NO 22
<211> LENGTH: 1255
<212> TYPE: PRT
<213> ORGANISM: Venezuelan equine encephalitis virus
<220> FEATURE:
<221> NAME/KEY: MISC_FEATURE
<223> OTHER INFORMATION: TC-38 structural polyprotein precursor sequence

<400> SEQUENCE: 22

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
            35                  40                  45

Thr Phe Lys Gln Arg Arg Asp Ala Pro Pro Glu Gly Pro Ser Ala Lys
        50                  55                  60

Lys Pro Lys Lys Glu Ala Ser Gln Lys Gln Gly Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
        130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
        290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
        370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
            405                 410                 415

Ser Leu Tyr Thr Ser Arg Pro Cys His Ile Val Asp Gly His Gly Tyr
```

```
                420             425             430
Phe Leu Leu Ala Arg Cys Pro Ala Gly Asp Ser Ile Thr Met Glu Phe
            435             440             445
Lys Lys Asp Ser Val Arg His Ser Cys Ser Val Pro Tyr Glu Val Lys
            450             455             460
Phe Asn Pro Val Gly Arg Glu Leu Tyr Thr His Pro Pro Glu His Gly
465             470             475             480
Val Glu Gln Ala Cys Gln Val Tyr Ala His Asp Ala Gln Asn Arg Gly
            485             490             495
Ala Tyr Val Glu Met His Leu Pro Gly Ser Glu Val Asp Ser Ser Leu
            500             505             510
Val Ser Leu Ser Gly Ser Ser Val Thr Val Thr Pro Pro Asp Gly Thr
            515             520             525
Ser Ala Leu Val Glu Cys Glu Cys Gly Gly Thr Lys Ile Ser Glu Thr
            530             535             540
Ile Asn Lys Thr Lys Gln Phe Ser Gln Cys Thr Lys Lys Glu Gln Cys
545             550             555             560
Arg Ala Tyr Arg Leu Gln Asn Asp Lys Trp Val Tyr Asn Ser Asp Lys
            565             570             575
Leu Pro Lys Ala Ala Gly Ala Thr Leu Lys Gly Lys Leu His Val Pro
            580             585             590
Phe Leu Leu Ala Asp Gly Lys Cys Thr Val Pro Leu Ala Pro Glu Pro
            595             600             605
Met Ile Thr Phe Gly Phe Arg Ser Val Ser Leu Lys Leu His Pro Lys
            610             615             620
Asn Pro Thr Tyr Leu Ile Thr Arg Gln Leu Ala Asp Glu Pro His Tyr
625             630             635             640
Thr His Glu Leu Ile Ser Glu Pro Ala Val Arg Asn Phe Thr Val Thr
            645             650             655
Glu Lys Gly Trp Glu Phe Val Trp Gly Asn His Pro Pro Lys Arg Phe
            660             665             670
Trp Ala Gln Glu Thr Ala Pro Gly Asn Pro His Gly Leu Pro His Glu
            675             680             685
Val Ile Thr His Tyr Tyr His Arg Tyr Pro Met Ser Thr Ile Leu Gly
            690             695             700
Leu Ser Ile Cys Ala Ala Ile Ala Thr Val Ser Val Ala Ala Ser Thr
705             710             715             720
Trp Leu Phe Cys Arg Ser Arg Val Ala Cys Leu Thr Pro Tyr Arg Leu
            725             730             735
Thr Pro Asn Ala Arg Ile Pro Phe Cys Leu Ala Val Leu Cys Cys Ala
            740             745             750
Arg Thr Ala Arg Ala Glu Thr Thr Trp Glu Ser Leu Asp His Leu Trp
            755             760             765
Asn Asn Asn Gln Gln Met Phe Trp Ile Gln Leu Leu Ile Pro Leu Ala
            770             775             780
Ala Leu Ile Val Val Thr Arg Leu Leu Arg Cys Val Cys Cys Val Val
785             790             795             800
Pro Phe Leu Val Met Ala Gly Ala Ala Gly Ala Gly Ala Tyr Glu His
            805             810             815
Ala Thr Thr Met Pro Ser Gln Ala Gly Ile Ser Tyr Asn Thr Ile Val
            820             825             830
Asn Arg Ala Gly Tyr Ala Pro Leu Pro Ile Ser Ile Thr Pro Thr Lys
            835             840             845
```

-continued

Ile Lys Leu Ile Pro Thr Val Asn Leu Glu Tyr Val Thr Cys His Tyr
850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
                915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr Asp Phe Pro Glu Tyr Gly Ala Gly
        995                 1000                1005

Gln Pro Gly Ala Phe Gly Asp Ile Gln Ser Arg Thr Val Ser Ser
    1010                1015                1020

Ser Asp Leu Tyr Ala Asn Thr Asn Leu Val Leu Gln Arg Pro Lys
    1025                1030                1035

Ala Gly Ala Ile His Val Pro Tyr Thr Gln Ala Pro Ser Gly Phe
    1040                1045                1050

Glu Gln Trp Lys Lys Asp Lys Ala Pro Ser Leu Lys Phe Thr Ala
    1055                1060                1065

Pro Phe Gly Cys Glu Ile Tyr Thr Asn Pro Ile Arg Ala Glu Asn
    1070                1075                1080

Cys Ala Val Gly Ser Ile Pro Leu Ala Phe Asp Ile Pro Asp Ala
    1085                1090                1095

Leu Phe Thr Arg Val Ser Glu Thr Pro Thr Leu Ser Ala Ala Glu
    1100                1105                1110

Cys Thr Leu Asn Glu Cys Val Tyr Ser Ser Asp Phe Gly Gly Ile
    1115                1120                1125

Ala Thr Val Lys Tyr Ser Ala Ser Lys Ser Gly Lys Cys Ala Val
    1130                1135                1140

His Val Pro Ser Gly Thr Ala Thr Leu Lys Glu Ala Ala Val Glu
    1145                1150                1155

Leu Thr Glu Gln Gly Ser Ala Thr Ile His Phe Ser Thr Ala Asn
    1160                1165                1170

Ile His Pro Glu Phe Arg Leu Gln Ile Cys Thr Ser Tyr Val Thr
    1175                1180                1185

Cys Lys Gly Asp Cys His Pro Pro Lys Asp His Ile Val Thr His
    1190                1195                1200

Pro Gln Tyr His Ala Gln Thr Phe Thr Ala Ala Val Ser Lys Thr
    1205                1210                1215

-continued

```
Ala Trp Thr Trp Leu Thr Ser Leu Leu Gly Gly Ser Ala Val Ile
1220                1225            1230

Ile Ile Ile Gly Leu Val Leu Ala Thr Ile Val Ala Met Tyr Val
1235                1240            1245

Leu Thr Asn Gln Lys His Asn
1250                1255
```